United States Patent [19]
Kume et al.

[11] Patent Number: 5,025,767
[45] Date of Patent: Jun. 25, 1991

[54] AIR/FUEL RATIO CONTROL SYSTEM FOR INTERNAL COMBUSTION ENGINE AND AIR/FUEL RATIO CONTROLLING OXYGEN DENSITY SENSOR

[75] Inventors: Tateo Kume, Kyoto; Reijiro Komagome, Joyo; Kazuhiro Shiraishi, Kyoto, all of Japan

[73] Assignee: Mitsubishi Jidosha Kogyo Kabushiki Kaisha, Tokyo, Japan

[21] Appl. No.: 335,212

[22] Filed: Apr. 7, 1989

[30] Foreign Application Priority Data

Apr. 9, 1988 [JP] Japan .................................. 63-87600

[51] Int. Cl.$^5$ ............................................. F02D 41/14
[52] U.S. Cl. ......................................... 123/489; 60/276
[58] Field of Search ....................... 123/440, 489, 589; 60/276

[56] References Cited

U.S. PATENT DOCUMENTS

| | | | |
|---|---|---|---|
| 4,117,815 | 10/1978 | Ikeura .................................. | 123/489 |
| 4,145,272 | 3/1979 | Nakamura et al. ................... | 60/276 |
| 4,264,425 | 4/1981 | Kimura et al. ....................... | 123/489 |
| 4,337,746 | 7/1982 | Masaki ................................. | 123/489 |

FOREIGN PATENT DOCUMENTS 3744206 8/1988 Fed. Rep. of Germany ...... 123/489
61-83466 4/1986 Japan .................................. 123/489

*Primary Examiner*—Andrew M. Dolinar
*Attorney, Agent, or Firm*—Wegner, Cantor, Mueller & Player

[57] ABSTRACT

Disclosed herein is an air/fuel ratio control system for an internal combustion engine. The system includes a first oxygen density sensor element, a second oxygen density sensor element having a slower detection response speed than the first sensor element, an air/fuel ratio control unit for controlling the air/fuel ratio of the engine on the basis of results of a comparison between a detection value from the first sensor element and a standard value, and an air/fuel ratio control correction means for effecting a correction to the air/fuel ratio control by the air/fuel ratio control unit on the basis of results of comparison between a detection value from the second sensor element and a second standard value. An air/fuel ratio controlling oxygen density sensor is also disclosed. The sensor is constructed of a first oxygen density sensor element and a second oxygen density sensor element for detecting the density of oxygen in exhaust gas at a slower detection response speed compared to the first sensor element. The first and second oxygen density sensor elements are both provided on a common base member.

6 Claims, 59 Drawing Sheets

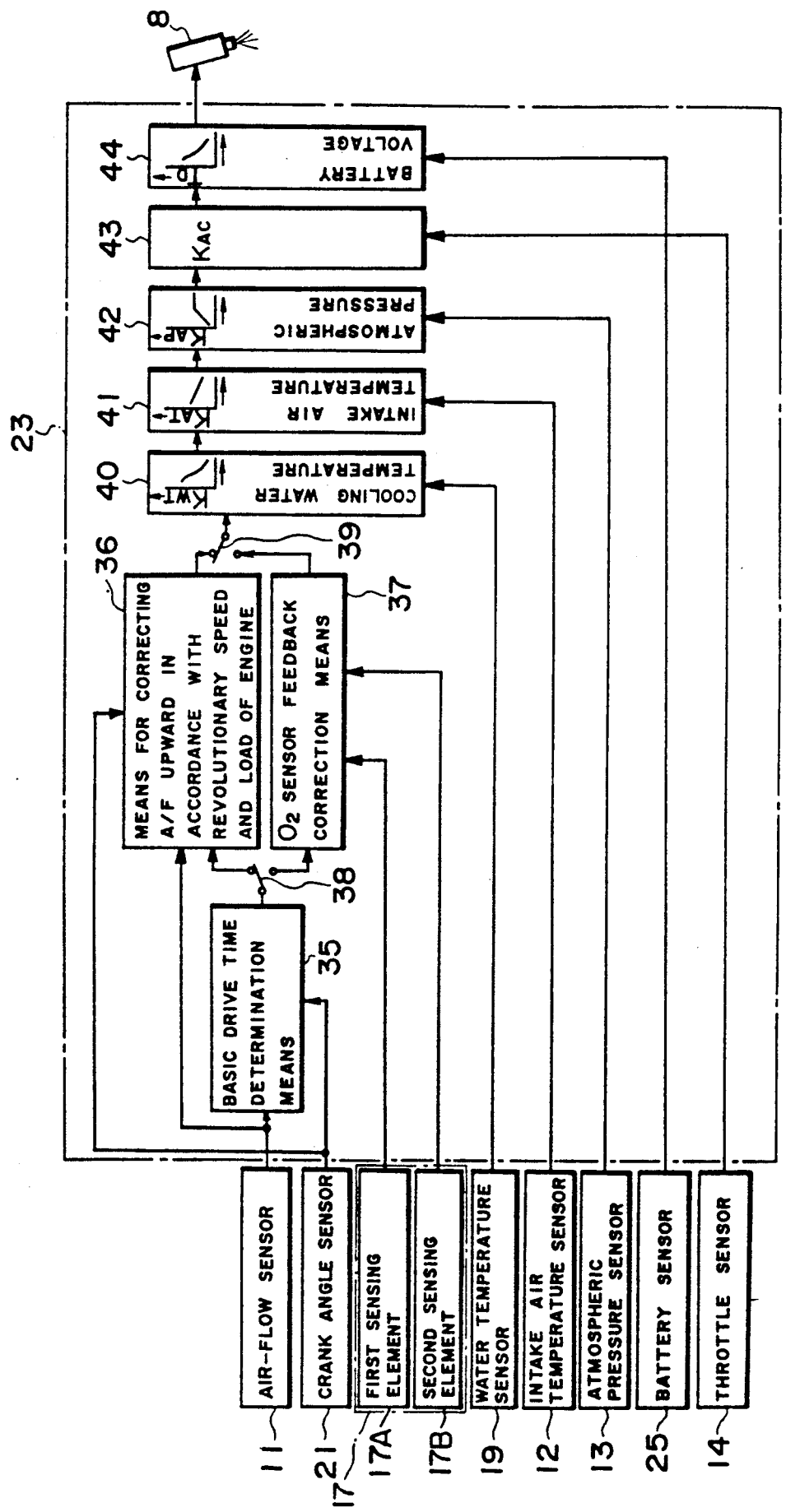

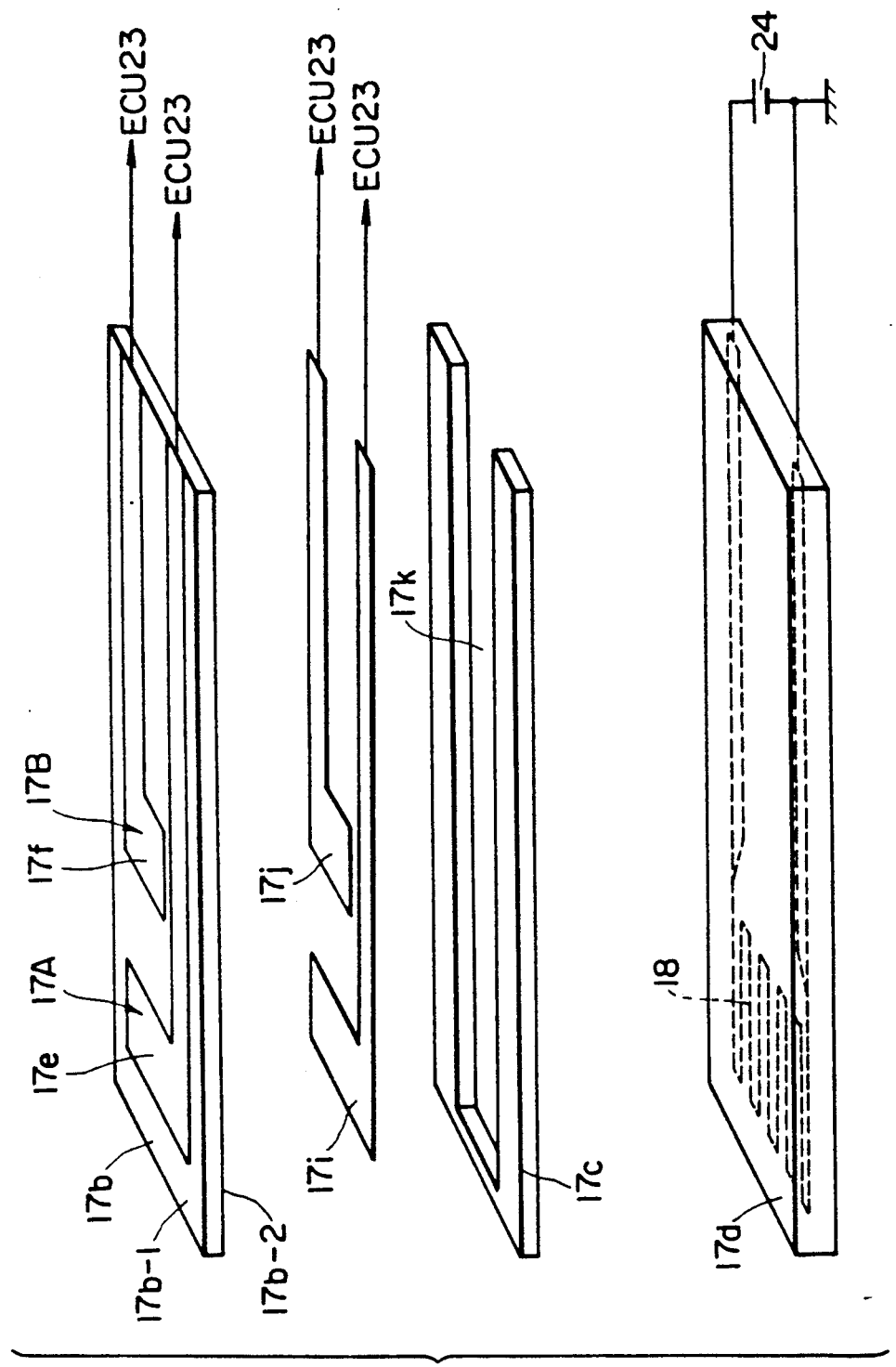

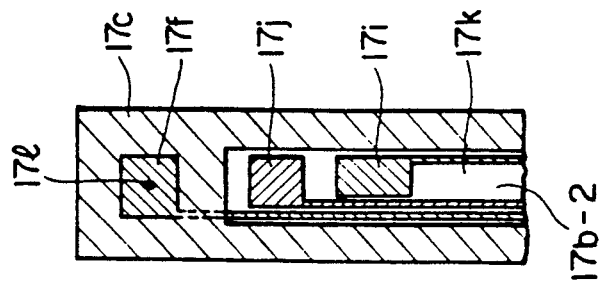
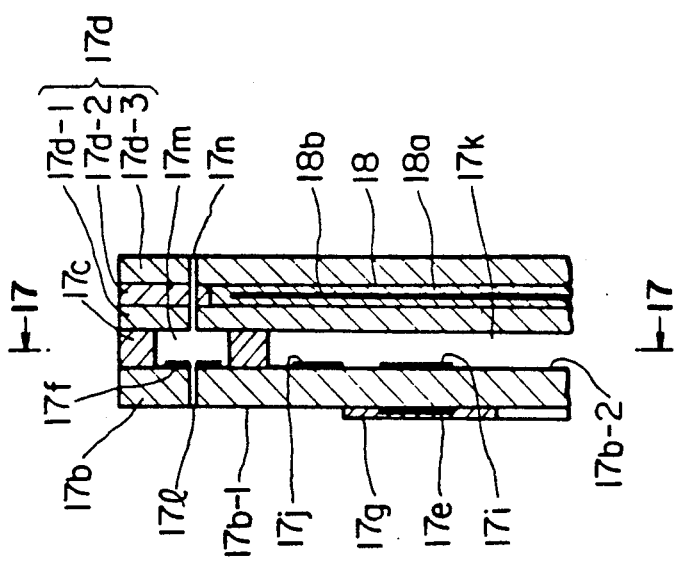
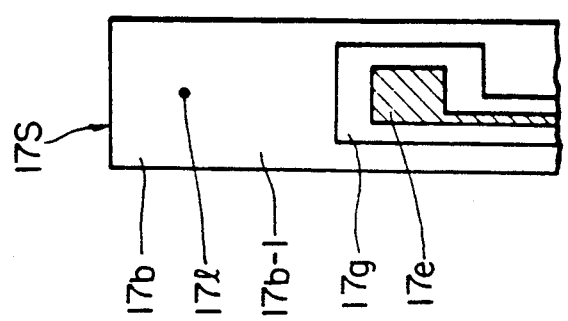

FIG.27(a)
FIG.27(b)
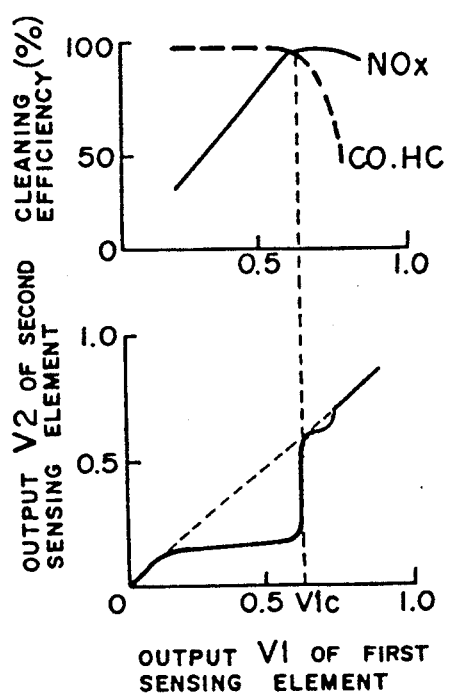
FIG.27(c)
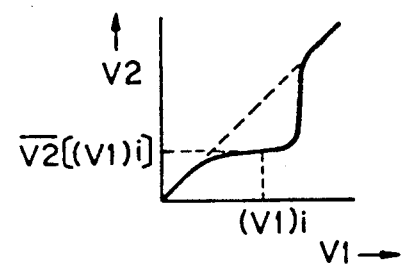

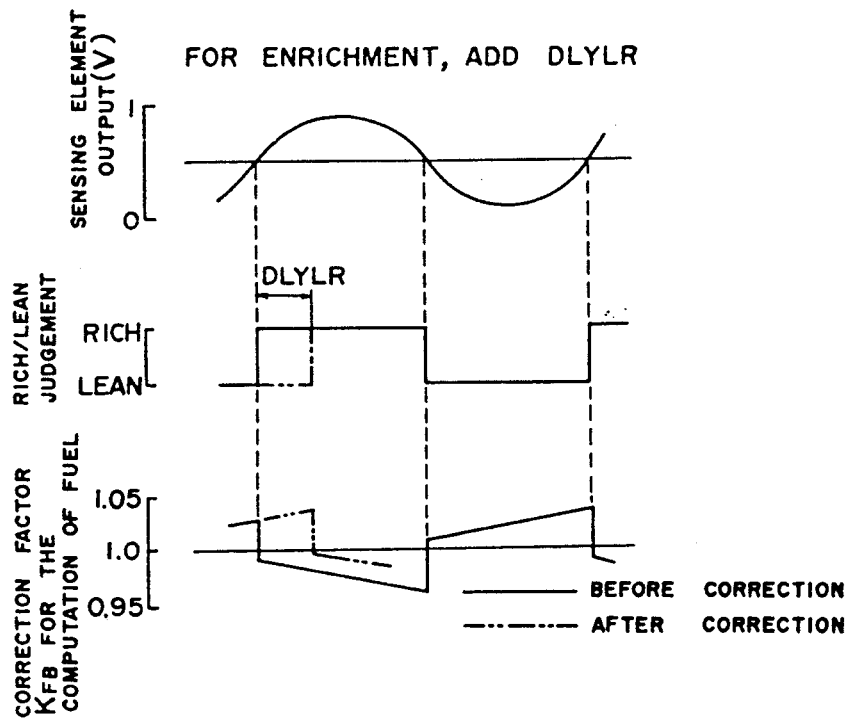
FIG.35(a)
FIG.35(b)
FIG.35(c)
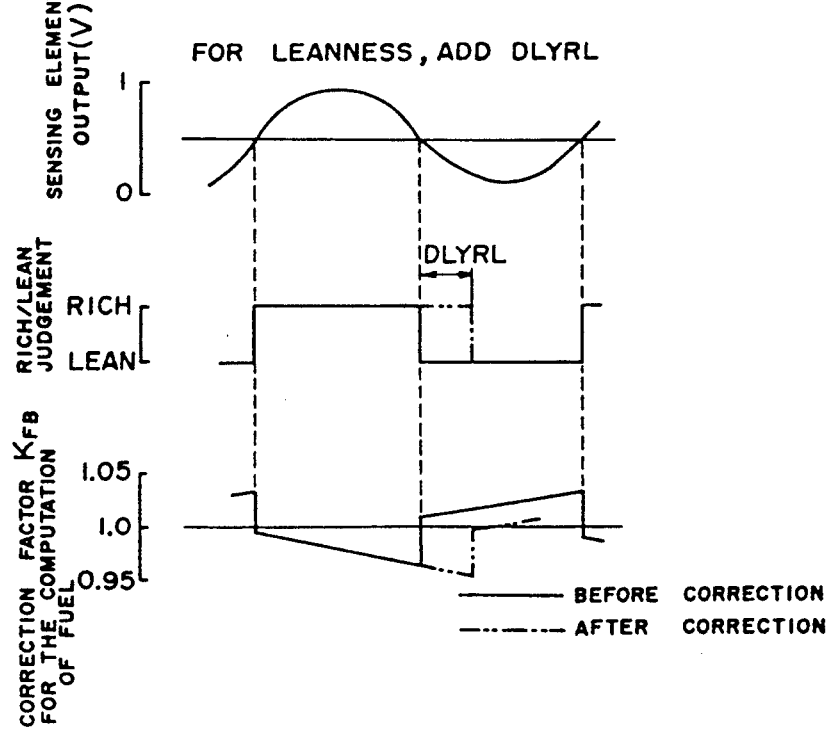
FIG.36(a)
FIG.36(b)
FIG.36(c)

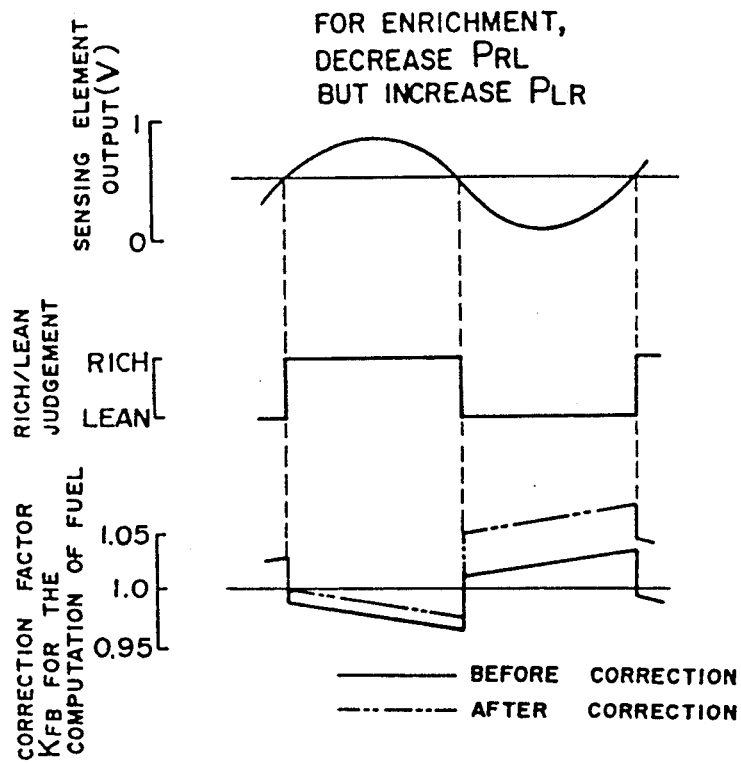
FIG.39(a)
FIG.39(b)
FIG.39(c)
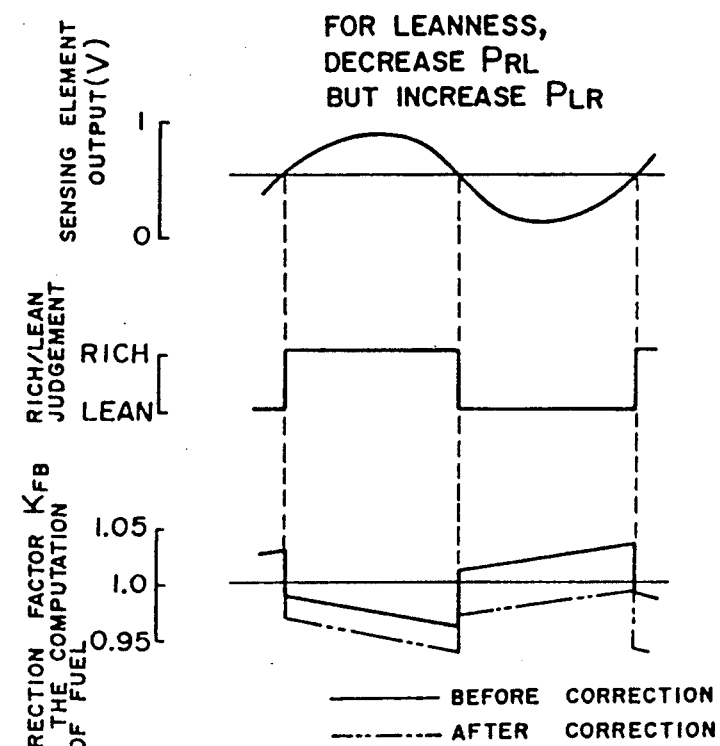
FIG.40(a)
FIG.40(b)
FIG.40(c)

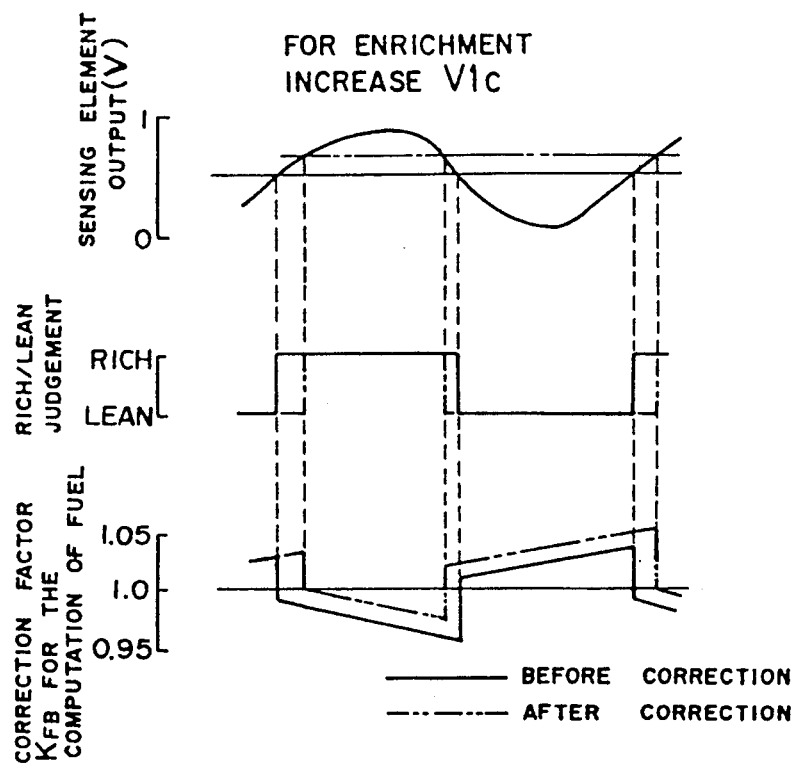
FIG.41(a)
FIG.41(b)
FIG.41(c)
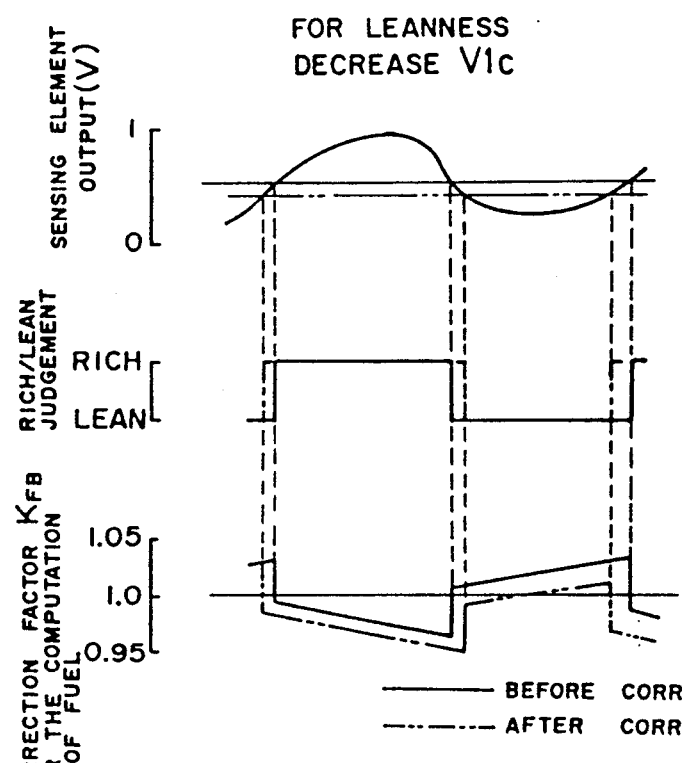
FIG.42(a)
FIG.42(b)
FIG.42(c)

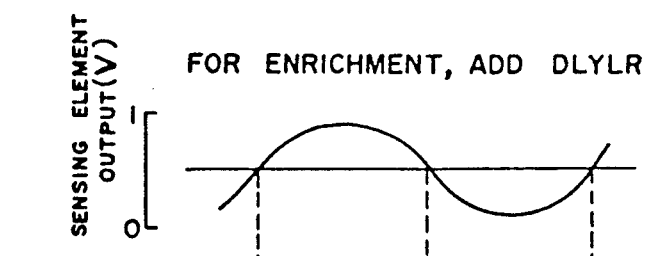
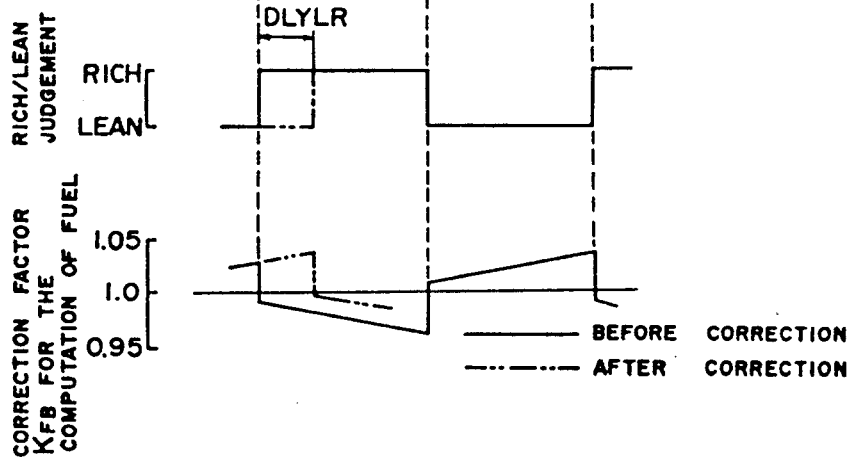

FIG.59(a)
FIG.59(b)
FIG.59(c)
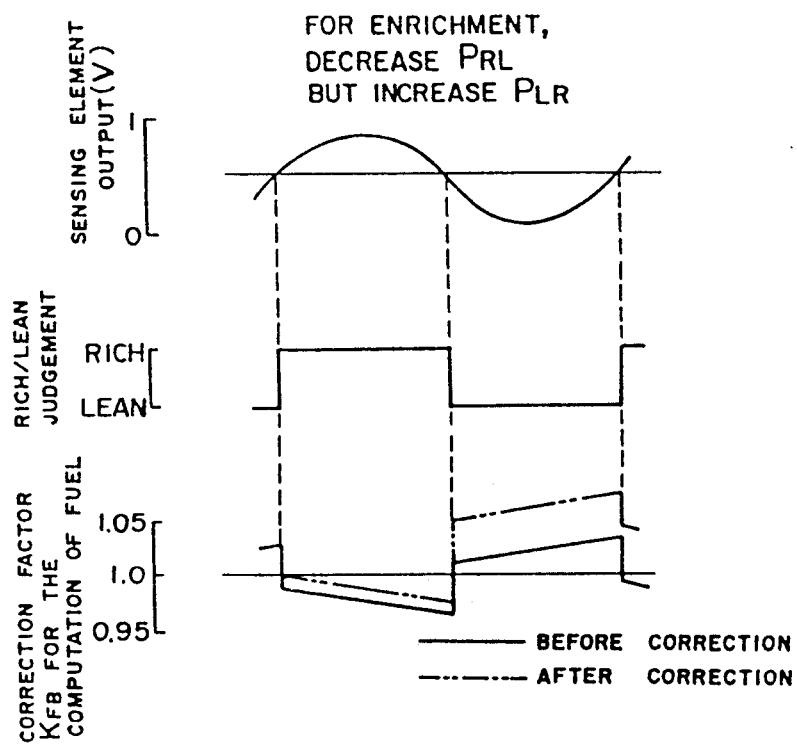
FIG.60(a)
FIG.60(b)
FIG.60(c)
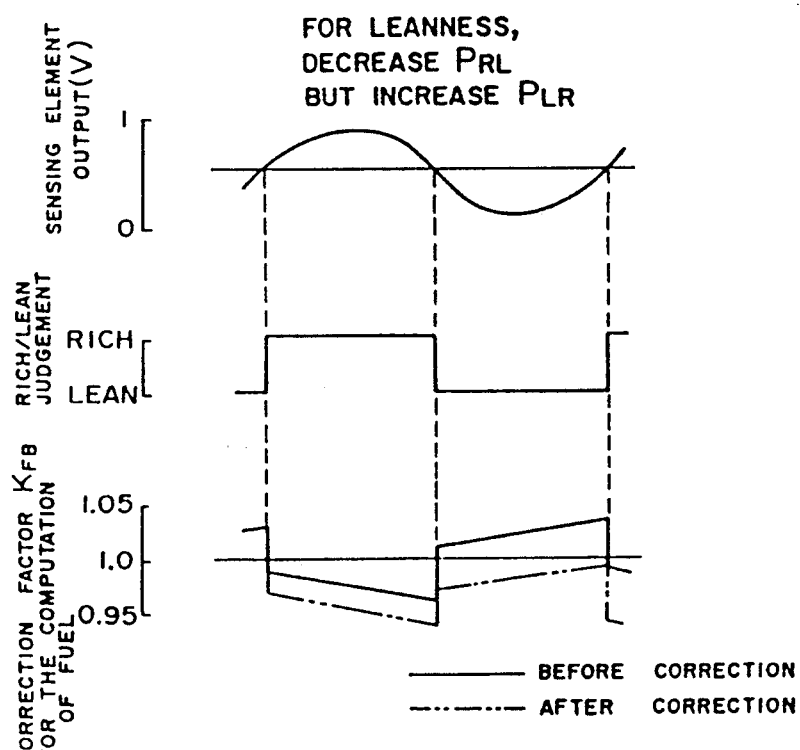

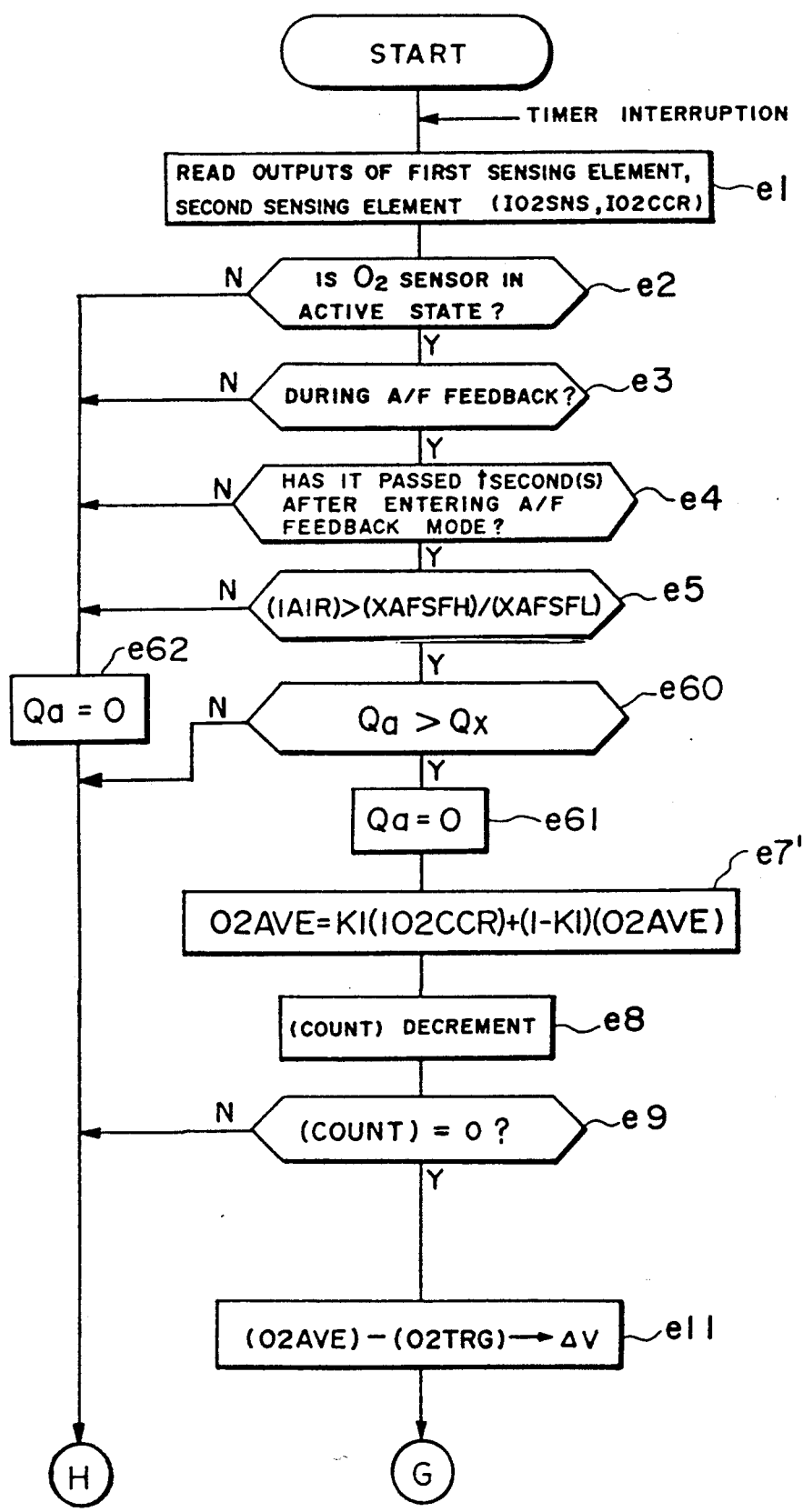

AIR/FUEL RATIO CONTROL SYSTEM FOR INTERNAL COMBUSTION ENGINE AND AIR/FUEL RATIO CONTROLLING OXYGEN DENSITY SENSOR

BACKGROUND OF THE INVENTION

1) Field of the Invention

This invention relates to an air/fuel ratio control system for an internal combustion engine, which controls the air/fuel ratio of the internal combustion engine by using, as feedback signals, detection signals from an oxygen density sensor (hereinafter called "$O_2$ sensor") arranged in the exhaust system of the internal combustion engine which may hereinafter be called "engine" as needed. This invention also relates to an improvement in an $O_2$ sensor employed in such an air/fuel ratio control.

2) Description of the Related Art

A variety of air/fuel ratio control systems making use of $O_2$ sensors have heretofore been proposed for internal combustion engines. In air/fuel ratio control systems of the above sort for internal combustion engines, an $O_2$ sensor which has been designed to change its output value abruptly near the stoichiometric fuel ratio by using the principle of oxygen concentration cells of a solid electrolyte, is arranged in an engine exhaust system at an upstream side relative to the point of arrangement of a catalytic converter (three-way catalyst) in the engine exhaust system. The air/fuel ratio of the internal combustion engine is controlled by comparing an output from the $O_2$ sensor with a predetermined standard value (Which is given as an intermediate value of values between which the abrupt change takes place, and this value is useful as a value for the judgement of either a rich air-fuel mixture or a lean air-fuel mixture) and then controlling the quantity of the fuel to be injected from each electromagnetic fuel injection valve (injector) in such a way that the air-fuel mixture is rendered lean when the output of the $O_2$ sensor is greater than the standard value but is rendered rich when the output of the $O_2$ sensor becomes smaller on the contrary.

It has recently been proposed to provide an additional $O_2$ sensor on the downstream side of the catalytic converter provided in the engine exhaust system (This $O_2$ sensor will hereinafter be called "rearward $O_2$ sensor" while an $O_2$ sensor provided on the upstream side of the catalytic converter like the above-described $O_2$ sensor will be called a forward $O_2$ sensor as opposed to the rearward $O_2$ sensor") and to use an output from the rearward $O_2$ sensor as auxiliary information for the control of the air/fuel ratio (so-called dual $O_2$ sensor system or double $O_2$ sensor system).

Among such conventional $O_2$-sensor dependent air/fuel ratio control systems for internal combustion engines, the former systems perform the feedback control of the air/fuel ratio only by the output of a single $O_2$ sensor and there is hence a room for improvements to the accuracy of the control, and regarding the $O_2$ sensor employed therein, there are the following additional problems. Since a measuring electrode (platinum or the like) arranged on the side of exhaust gas has lower catalytic ability, the arrival of a non-equlibrated component (for example, CO or HC when the air/fuel ratio is lean) at the measuring electrode causes a reaction such as $CO + O^{2-} \rightarrow CO_2 + e^-$. The conventional $O_2$ sensors therefore generates an output indicating a rich air/fuel ratio so that the static $\lambda$ point is usually shifted to the lean side. One of causes for such variations of $O_2$ sensors is considered to be attributable to variations in the catalytic ability of measuring electrodes, resulting in the proposal of $O_2$ sensors with improved catalytic ability around their $O_2$ sensor electrodes in recent years. These $O_2$ sensors are however accompanied with the potential problems that the responsibility of the sensor output may be lowered and greater variations may take place in the deterioration of their performance.

In the latter systems, namely, the dual $O_2$ sensor systems using a forward $O_2$ sensor and a rearward $O_2$ sensor, the temperature on a downstream side of the catalytic converter tends to become lower without exception so that the output of the rearward $O_2$ sensor does not become stable. Even when the output from the rearward $O_2$ sensor is used as auxiliary information for the control of the air/fuel ratio, the air/fuel ratio feedback control based on the output of the forward $O_2$ sensor may not be successfully performed in some instances. Here again, there is a room for improvements. Further, the catalytic converter has a large $O_2$ storage capacity. This $O_2$ storage capacity however changes along with durability deterioration of its catalyst. As a result, the responsibility of the air/fuel ratio control system also varies along with deterioration of the catalyst. A complex correction means therefore becomes indispensable if one wants to always maintain at an optimum value the control factor for the air/fuel ratio control.

SUMMARY OF THE INVENTION

It is the object of this invention to solve such a problem.

More specifically, an object of this invention is to provide an air/fuel ratio control system for an internal combustion engine by providing two $O_2$ sensor elements on an upstream side of a catalytic converter and also exercising ingenious improvements on one of the $O_2$ sensor elements to allow it to have equivalent function to the rearward $O_2$ sensor, whereby the accuracy of the control is not changed by variations in characteristics of each $O_2$ sensor and changes of its characteristics along the passage of time and the efficiency of cleaning of exhaust gas by the catalytic converter can also be maintained high, thereby making it possible to obtain high reliability in regard to the control.

Another object of this invention is to provide an $O_2$ sensor for arrangement in an exhaust system of an internal combustion engine to control the air/fuel ratio of the internal combustion engine, which permits compact arrangement and housing of the two $O_2$ sensor elements described above.

In a first aspect of this invention, there is thus provided an air/fuel ratio control system for an internal combustion engine, comprising:
- a first oxygen density sensor element for arrangement on the upstream side of a catalytic converter so as to detect the density of oxygen in exhaust gas, said catalytic converter being provided in an exhaust system of the internal combustion engine and adapted to clean the exhaust gas;
- a second oxygen density sensor element for arrangement on the upstream side of the catalytic converter said second oxygen density having a slower detection response speed in comparison with the first oxygen density sensor element;

an air/fuel ratio control means for controlling the air/fuel ratio of the internal combustion engine on the basis of results of a comparison between a detection value from the first oxygen density sensor element and a predetermined standard value; and an air/fuel ratio control correction means for effecting a correction to the air/fuel ratio control by the air/fuel ratio control means on the basis of results of comparison between a detection value from the second oxygen density sensor element and a second standard value for the second oxygen density sensor element.

In a second aspect of this invention, there is also provided an air/fuel ratio control system for an internal combustion engine, comprising:

an oxygen density sensor equipped integrally with a first oxygen density sensor element and a second oxygen density sensor element adapted to detect at different detection response speeds the density of oxygen in exhaust gas on the upstream side of a catalytic converter, said catalytic converter being provided in an exhaust system of the internal combustion engine and adapted to clean the exhaust gas;

an air/fuel ratio control means for controlling the air/fuel ratio of the internal combustion engine on the basis of results of a comparison between a detection value from the first oxygen density sensor element having a faster detection response speed in the oxygen density sensor and a predetermined standard value; and an air/fuel ratio control correction means for effecting a correction to the air/fuel control by the air/fuel ratio control means on the basis of results of a comparison between a detection value from the second oxygen density sensor element having a slower detection response speed in the oxygen density sensor and a second standard value for the second oxygen density sensor element.

In a third aspect of this invention, there is also provided an air/fuel ratio controlling oxygen density sensor for arrangement in an exhaust system of an internal combustion engine. The oxygen density sensor comprises a first oxygen density sensor element for detecting the density of oxygen in exhaust gas and a second oxygen density sensor element for detecting the density of oxygen in the exhaust gas at a slower detection response speed compared to the first oxygen density sensor element, said first and second oxygen density sensor elements being both provided on a common base member.

In a fourth aspect of this invention, there is also provided an air/fuel ratio controlling oxygen density sensor for arrangement in an exhaust system of an internal combustion engine. The oxygen density sensor comprises a base member composed of a solid electrolyte, a first measuring electrode provided on a side wall of the base member, said side wall being to be positioned on the side of the exhaust gas, a second measuring electrode covered with a catalytic component and provided on the side wall of the base member, and at least one reference electrode arranged on another side wall of the base member in an opposed relation to each of the first and second measuring electrodes, said another side wall being to be exposed to reference conditions.

In a fifth aspect of this invention, there is also provided an air/fuel ratio controlling oxygen density sensor for arrangement in an exhaust system of an internal combustion engine. The oxygen density sensor comprises a base member composed of a solid electrolyte, a first measuring electrode provided on a side wall of the base member, said side wall being to be positioned on the side of the exhaust gas, a diffusion chamber formed in the base member to receive the exhaust gas through a small-diameter passage, a second measuring electrode arranged within the diffusion chamber, a catalyst provided in the diffusion chamber to cover the second measuring electrode and at least one reference electrode arranged on another side wall of the base member in an opposed relation to each of the first and second measuring electrodes, said another side wall being to be exposed to reference conditions.

In a sixth aspect of this invention, there is also provided an air/fuel ratio controlling oxygen density sensor for arrangement in an exhaust system of an internal combustion engine. The oxygen density sensor comprises a base member composed of a solid electrolyte, a first measuring electrode provided on a side wall of the base member, said side wall being to be positioned on the side of the exhaust gas, a diffusion chamber formed in the base member to the exhaust gas through a small-diameter passage, a second measuring electrode having catalytic ability and arranged within the diffusion chamber, and at least one reference electrode arranged on another side wall of the base member in an opposed relation to each of the first and second measuring electrodes, said another side wall being to be exposed to reference conditions.

In the air/fuel ratio control system according to the first aspect of this invention which is suited for use with an internal combustion engine, the air/fuel ratio of the internal combustion engine is controlled by the air/fuel ratio control means on the basis of results of a comparison between a detection value from the first oxygen density sensor element and a predetermined standard value, and the air/fuel ratio control correction means effects a correction to the air/fuel ratio control by the air/fuel ratio control means on the basis of results of a comparison between a detection value from the second oxygen density sensor element and a second standard value for the second oxygen density sensor element. It is thus possible to provide two oxygen density sensor elements on the upstream side of a catalytic converter and to exercise ingenious improvements on one of the oxygen density sensor elements to allow it to have equivalent function to the rearward $O_2$ sensor, whereby the accuracy of the control is not changed by variations in characteristics of each oxygen sensor and changes of its characteristics along the passage of time and the efficiency of cleaning of exhaust gas by the catalytic converter can also be maintained high, thereby making it possible to obtain high reliability in regard to the control.

In a preferred modification of the air/fuel ratio control system according to the first aspect of this invention, the second standard value is set as a predetermined fixed value. This preferred modification can bring about similar effects or advantages as the system according to the first aspect of this invention.

In another preferred modification o the air/fuel ratio control system according to the first aspect of this invention, the second standard value is changed on the basis of outputs from the first and second oxygen density sensor elements. An air/fuel ratio control having still higher accuracy can therefore be realized.

In the air/fuel ratio control system according to the second aspect of this invention which is also suited for used with an internal combustion engine, the air/fuel ratio control means controls the air/fuel ratio of the internal combustion engine on the basis of results of a comparison between a detection value from the oxygen density sensor element (the first oxygen density sensor) having the faster detection response speed in the oxygen density sensor equipped integrally with the first oxygen density sensor element and second oxygen density sensor element, and the air/fuel ratio control correction means effects a correction to the air/fuel control by the air/fuel ratio control means on the basis of results of a comparison between a detection value from the oxygen density sensor element (the second oxygen density sensor) having the slower detection response speed in the oxygen density sensor and a second standard value for the second oxygen density sensor element. The system according to the second aspect of this invention therefore has the advantage that the use of the oxygen sensor, which can be easily arranged and housed, permits a highly-reliable air/fuel ratio control while minimizing the cost increase of the overall system.

The air/fuel ratio controlling oxygen density sensor according to the third aspect of this invention is arranged on the upstream side of a catalytic converter, which is provided in an exhaust system of an internal combustion engine and is adapted to clean exhaust gas. Since the first oxygen density sensor element and the second oxygen density sensor element are provided on the common base member, it is possible to arrange and house these two oxygen density sensor elements in a compact manner. It is thus possible to provide a sophisticated sensor with ease. Since both the oxygen density sensor elements are arranged under substantially the same temperature conditions, a further advantage has been brought about that the sensor does not develop such inconvenience as experienced with conventional dual $O_2$ sensor systems.

In the air/fuel ratio controlling oxygen density sensor according to the fourth aspect of this invention, the first measuring electrode is provided on the side wall of the base member, said side wall being to be positioned on the side of the exhaust gas, and the second measuring electrode covered with a catalytic component is also provided on the side wall of the base member. At least one reference electrode is arranged on another side wall of the base member in an opposed relation to each of the first and second measuring electrodes, said another side wall being to be positioned on the side of the reference conditions. These electrodes can therefore be arranged and housed in a more compact manner as a single sensor. It is thus possible to provide a sophisticated sensor with ease. Since both the oxygen density sensor elements are arranged under substantially the same temperature conditions, a further advantage has been brought about that the sensor does not develop such inconvenience as experienced with conventional dual $O_2$ sensor systems.

The air/fuel ratio controlling oxygen density sensor according to the fifth aspect of this invention is composed of the first measuring electrode provided on a side wall of the base member, said side wall being to be positioned on the side of the exhaust gas, the diffusion chamber formed in the base member to receive the exhaust gas through the small-diameter passage, the second measuring electrode arranged within the diffusion chamber, the catalyst provided in the diffusion chamber to cover the second measuring electrode and at least one reference electrode arranged on another side wall of the base member in an opposed relation to each of the first and second measuring electrodes, said another side wall being to be positioned on the side of the atmosphere. These electrodes can also be arranged and housed in a more compact manner as a single sensor. It is thus possible to provide a sophisticated sensor with ease. Since both the oxygen density sensor elements are arranged under substantially the same temperature conditions, a further advantage has been brought about that the sensor does not develop such inconvenience as experienced with conventional dual $O_2$ sensor systems.

The air/fuel ratio controlling oxygen density sensor according to the sixth aspect of this invention is composed of the first measuring electrode provided on a side wall of the base member, said side wall being to be positioned on the side of the exhaust gas, the diffusion chamber formed in the base member to the exhaust gas through the small-diameter passage, the second measuring electrode having catalytic ability and arranged within the diffusion chamber, and at least one reference electrode arranged on another side wall of the base member in an opposed relation to each of the first and second measuring electrodes, said another side wall being to be positioned on the side of the atmosphere. These electrodes can also be arranged and housed in a more compact manner as a single sensor. It is thus possible to provide a sophisticated sensor with ease. Since both the oxygen density sensor elements are arranged under substantially the same temperature conditions, a further advantage has been brought about that the sensor does not develop such inconvenience as experienced with conventional dual $O_2$ sensor systems.

BRIEF DESCRIPTION OF THE DRAWINGS

FIGS. 1 through 42 illustrate an air/fuel ratio control system according to a first embodiment of this invention, which is suitable for use with an internal combustion engine, in which:

FIG. 1(a) is a block diagram of the control system;

FIG. 2 is a block diagram of the control system, which depicts its hardware primarily;

FIG. 3 is a schematic illustration showing an overall engine system;

FIGS. 4 through 10 show respectively an $O_2$ sensor which can be employed in the control system, in which:

FIG. 4 is a perspective view of the $O_2$ sensor;

FIG. 5 is a fragmentary perspective view of the $O_2$ sensor, a part of which has been broken away to show an essential part thereof;

FIG. 6 is a fragmentary front view of the $O_2$ sensor;

FIG. 7 is a fragmentary cross-sectional view of the $O_2$ sensor;

FIG. 8 is an exploded perspective view of the $O_2$ sensor;

FIGS. 11 through 14 show another $O_2$ sensor suitable for use in the system of this invention, in which:

FIG. 11 is a fragmentary front view of the $O_2$ sensor;

FIG. 12 is a fragmentary cross sectional view of the $O_2$ sensor;

FIG. 13 is a cross-sectional view taken in the direction of arrows 13—13 of FIG. 12.

FIGS. 15 through 17 depict a further O₂ sensor suitable for use in the system of this invention, in which:

FIG. 15 is a fragmentary front view of the O₂ sensor;

FIG. 16 is a fragmentary cross sectional view of the O₂ sensor; and

FIG. 17 is a cross-sectional view taken in the direction of arrows 17—17 of FIG. 16;

FIG. 19 is a flow chart for describing an electromagnetic valve drive routine for the control system;

FIG. 21 is a flow chart for determining a deviation between an output from a second sensing element and a target value (a second standard value);

FIG. 22 is a flow chart for correcting response delay time on the basis of the deviation determined in FIG. 21;

FIG. 23 is a flow chart for correcting, based on the deviation determined in FIG. 21, an integral gain for the air/fuel ratio feedback control;

FIG. 24 is a flow chart for correcting, based on the deviation determined in FIG. 21, a proportional gain for the air/fuel ratio feedback control;

FIG. 25 is a flow chart for correcting, based on the deviation determined in FIG. 21, a standard value for rich/lean judgement to be compared with an output from a first sensing element;

FIG. 26 is a graph for illustrating a correction factor which is for the air/fuel ratio feedback control;

FIGS. 27(a) through 27(d) are respectively graphs for describing the operation of the control system;

FIGS. 35 and 36 are respectively graphs for describing a correction method which relies upon the response delay time;

FIGS. 37 and 38 are respectively graphs for describing a correction method which relies upon the integral gain for the air/fuel ratio feedback control;

FIGS. 39 and 40 are respectively graphs for describing a correction method which relies upon the proportional gain for the air/fuel ratio feedback control; and FIGS. 41 and 42 are respectively graphs for describing a correction method which relies upon the standard value for rich/lean judgement to be compared with the output from the forward O₂ sensor; and FIGS. 43 through 60 depict an air/fuel ratio control system according to a second embodiment of this invention, which is suitable for use with an internal combustion engine, in which:

FIG. 43 is a fragmentary block diagram of the control system;

FIG. 45 is a flow chart for determining a deviation between an output from a second sensing element in the control system and a target value;

FIG. 46 is a flow chart for correcting response delay time on the basis of the deviation determined in FIG. 45;

FIG. 47 is a flow chart for correcting, based on the deviation determined in FIG. 45, an integral gain for the air/fuel ratio feedback control;

FIG. 48 is a flow chart for correcting, based on the deviation determined in FIG. 45, a proportional gain for the air/fuel ratio feedback control;

FIGS. 55 and 56 are respectively graphs for describing a correction method which relies upon the response delay time;

FIGS. 57 and 58 are respectively graphs for describing a correction method which relies upon the integral gain for the air/fuel ratio feedback control;

FIGS. 59 and 60 are respectively graphs for describing a correction method which relies upon the proportional grain for the air/fuel ratio feedback control; and FIGS. 61 and 62 are flow charts showing modifications of the first and second embodiments, respectively;

FIGS. 63 and 64 depict an air/fuel ratio control system according to a third embodiment of this invention, which is suitable for use with an internal combustion engine, in which:

FIG. 64 is a flow chart for determining a correction factor on the basis of any one of the deviations determined in FIGS. 21, 45 and 62 respectively.

FIGS. 65 and 66 show an air/fuel ratio system according to a fourth embodiment of this invention, which is suitable for use with an internal combustion engine, in which:

FIG. 65 is a fragmentary block diagram of the control system; and

FIG. 66 is a flow chart for describing a main routine of the control system.

DETAILED DESCRIPTION OF THE INVENTION AND PREFERRED EMBODIMENTS

The embodiments of this invention will hereinafter be described with reference to the accompanying drawings.

Figure 3:
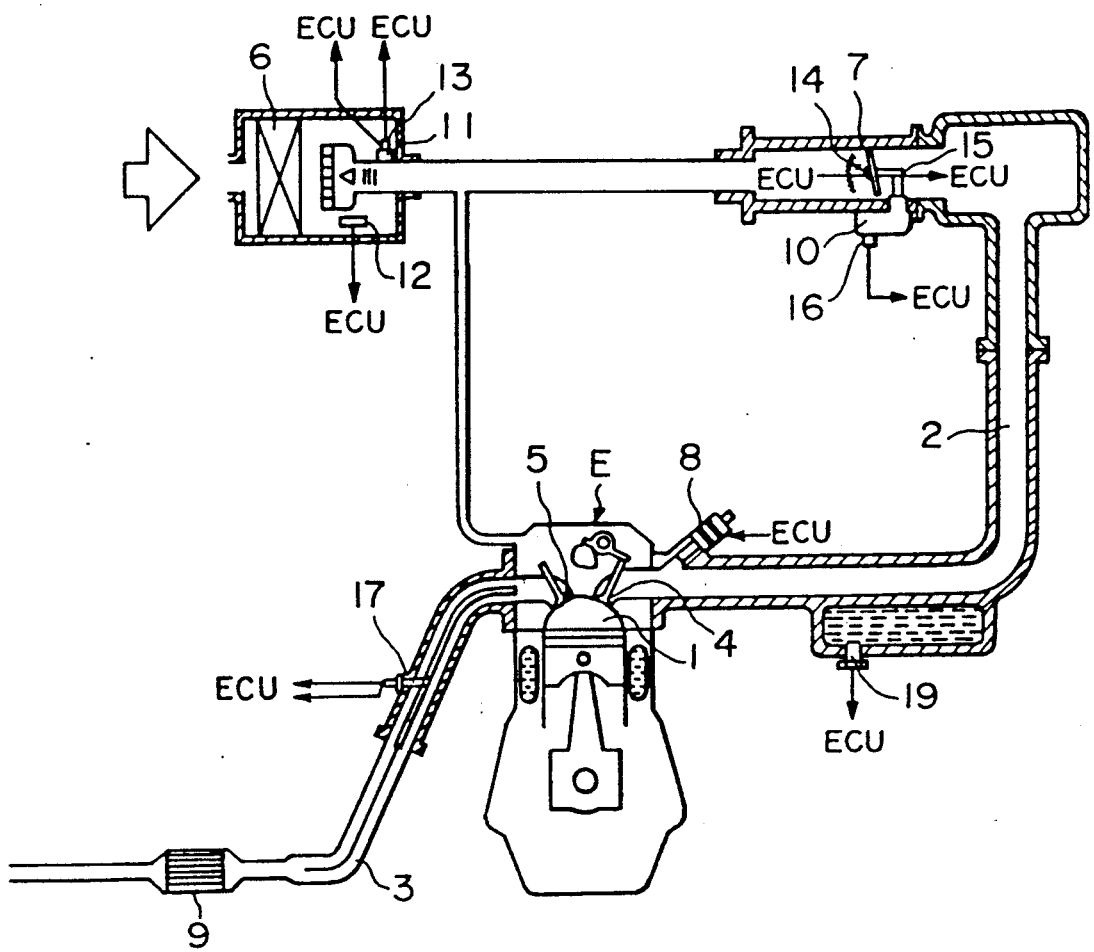

An engine system controlled by the system of this invention may be illustrated as shown in FIG. 3, in which an engine E has an intake passage 2 and an exhaust passage 3, both, communicated to a combustion chamber 1. The communication between the intake passage 2 and combustion chamber 1 is controlled by an intake valve 4, while that of the discharge passage 3 with the combustion chamber 1 is controlled by an exhaust valve 5.

In addition, the intake passage 2 is provided with an air cleaner 6, a throttle valve 7 and an electromagnetic fuel injection valve (solenoid valve) 8 in order from the upstream side thereof. The exhaust passage 3 is provided with a catalytic converter (three-way catalyst) 9 for cleaning exhaust gas and an unillustrated muffler in order from the upstream side thereof.

Incidentally, solenoid valves of the same type as the solenoid valve 8 are provided as many as the number of cylinders in an intake manifold portion. Let's now assume that the engine E is an in-line 4-cylinder engine in the present embodiment. Four solenoid valves 8 are hence provided. In other words, the engine E can be said to be an engine of the so-called multi-point fuel injection (MPI) system.

The throttle valve 7 is connected via an unillustrated wire cable to an accelerator pedal (not shown) so that the opening rate of the throttle valve 7 changes in accordance with the degree of depression of the accelerator pedal. In addition, the throttle valve 7 is also driven by an idling speed control motor (ISC motor), whereby the opening rate of the throttle valve 7 can be varied without need for depression of the accelerator pedal upon idling.

Owing to the above-described construction, air which has been drawn in accordance with the opening rate of the throttle valve 7 through the air cleaner 6 is mixed with a fuel from the solenoid valve 8 in the intake manifold portion so as to give a suitable air/fuel ratio. The resulting air-fuel mixture is ignited at suitable timing by an unillustrated spark plug in the combustion chamber 1, so that the air-fuel mixture is caused to burn. After producing an engine torque, the air-fuel mixture is discharged as exhaust gas into the exhaust passage 3 and subsequent to cleaning of three noxious components CO, HC, $NO_x$ in the exhaust gas by the catalytic converter 9, the exhaust gas is reduced in noise by an unillustrated muffler and then released into the surrounding atmosphere.

A variety of sensors is provided in order to control the engine E. On the side of the intake passage 2 first of all, there are provided an airflow sensor 11 for detecting the quantity of intake air from Karman vortex information, an intake air temperature sensor 12 for detecting the temperature of the air drawn and a barometric pressure sensor 13, all, in the portion where the air cleaner is provided. In a portion where the throttle valve is installed, there are provided a throttle sensor 14 of the potentiometer type, said throttle sensor 14 being adapted to detect the opening rate of the throttle valve 7, an idle switch 15 for detecting the state of idling, and a motor position sensor 16 for detecting the position of the ISC motor 10.

Further, on the side of the exhaust passage 3, an oxygen density sensor ($O_2$ sensor) 17 for detecting the oxygen ($O_2$) density in the exhaust gas is provided at a position upstream of the catalytic converter 9. Here, the $O_2$ sensor 17 makes use of the principle of oxygen concentration cells of a solid electrolyte. It has such a characteristic that its output voltage changes abruptly near the stoichiometric air/fuel ratio. Its voltage is low on the side leaner than the stoichiometric air/fuel ratio but high on the side richer than the stoichiometric air/fuel ratio.

Figure 4:
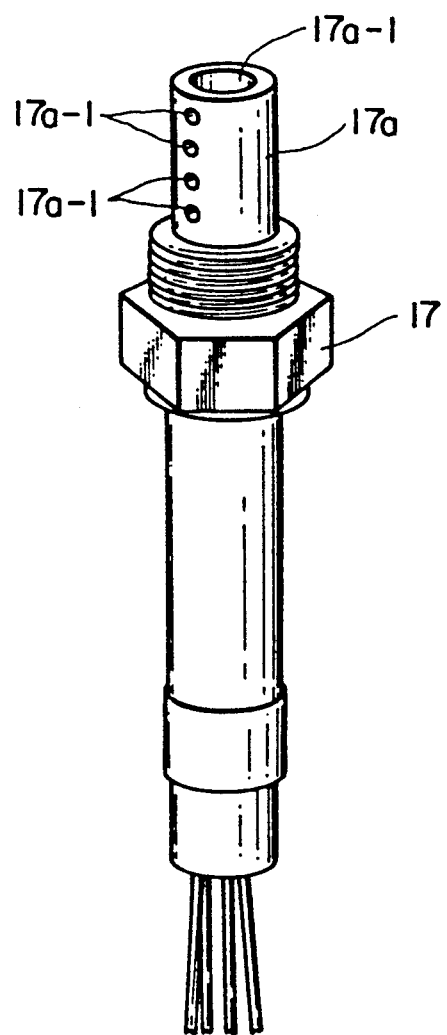
Figure 5:
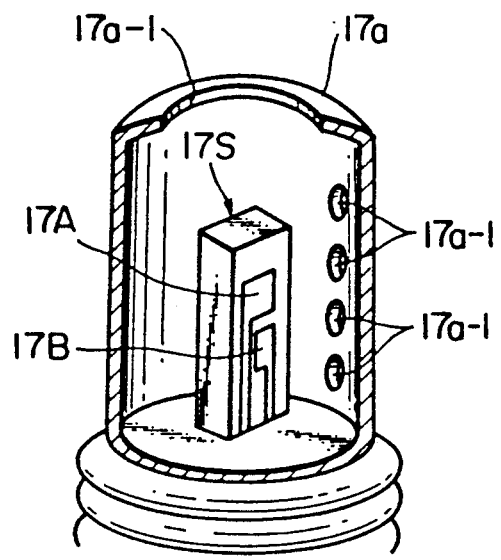
Figure 6:
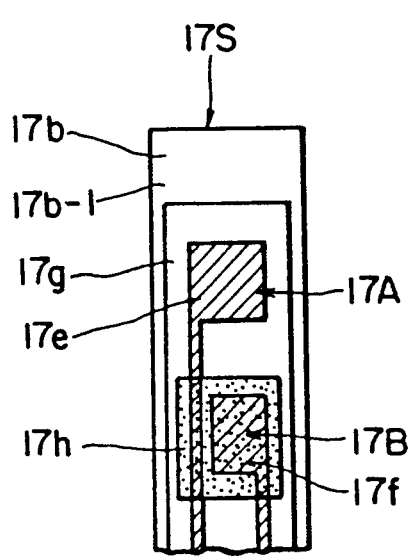

The $O_2$ sensor 17 has an external appearance as shown in FIG. 4. As depicted in FIG. 5, the $O_2$ sensor 17 has the structure that a sensor element portion 17S, which is to be arranged within the exhaust passage 3, is located at a tip portion of the $O_2$ sensor and is covered by a protective cover 17a. Plural communication holes 17a-1 are formed through the protective cover 17a to communicate the exhaust passage 3 with a space in which the sensor element portion is arranged.

As shown in FIGS. 5 through 8, the $O_2$ sensor 17 is equipped with a first sensing element 17A as a first $O_2$ sensor element for detecting the density of oxygen in exhaust gas and a second sensing element 17B as a second $O_2$ sensor element having a slower oxygen density detection response speed compared to the first sensing element 17A. These first sensing element 17A and second sensing element 17B are provided on a common base member 17b.

Namely, the $O_2$ sensor 17 has the base member 17b made of a solid electrolyte such as $ZrO_2$. On an exhaust-gas-side wall 17b-1 of the base member 17b, there are provided a first measuring electrode 17e, and a second measuring electrode 17f covered with a catalyst layer 17h which contains Pt and/or Rh. Reference electrodes 17i,17j are provided on an atmosphere-side wall (wall on the side of reference conditions) 17b-2 of the base member 17b in an opposed relation with these measuring electrodes 17e,17f, respectively. The surface of each of the measuring electrodes 17e,17f is covered with a coating layer 17g made of alumina or the like. The catalyst layer 17h covers the second measuring electrode 17f with the coating layer 17g interposed therebetween. Incidentally, the first and second measuring electrode 17e,17f and the reference electrodes 17i,17j are all formed of Pt which is suitable for the formation of electrodes for an oxygen concentration cell.

The first sensing element 17A is constructed of the first measuring electrode 17e, the reference electrode 17i and the solid electrolyte (a portion of the base member 17b) located between these electrodes. The second sensing element 17B is constructed of the second measuring electrode 17f having the catalyst layer 17h, the reference electrode 17j and the solid electrolyte (another portion of the base member 17b) located between these electrodes.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the catalyst layer 17h while its responsibility is slower relative to the first sensing element. It is hence possible to exclude non-equilibrated components which are contained in exhaust gas and would otherwise reach the electrode, thereby making it possible to shift the static λ point toward the stoichiometric point, in other words, to reduce variations of the static λ point and dynamic λ point. Namely, the second sensing element 17B can show exactly the same function as the conventional rearward $O_2$ sensor although it is located on the upstream side of the catalytic converter 9.

Figure 7:
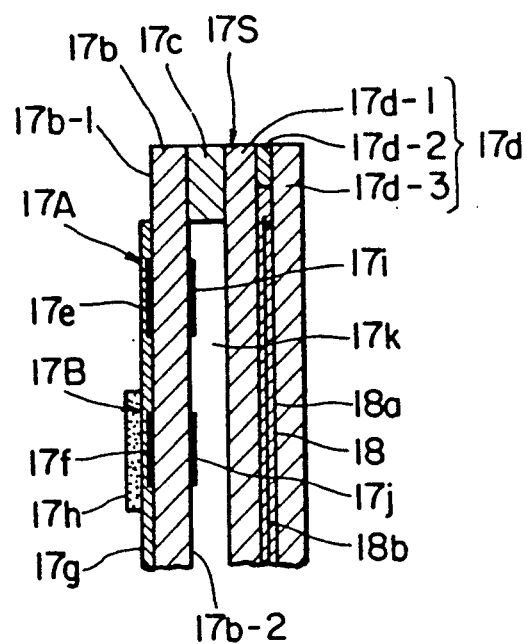

The $O_2$ sensor 17 is constructed as an $O_2$ sensor of the stacked type. Namely, the $O_2$ sensor 17 has been formed by stacking five plate-like members 17b,17c,17d-1,17d-2,17d-3 *which are each made of a solid electrolyte such as $ZrO_2$*. Of these plate-like members, the one arranged on the most left-hand side as viewed in FIG. 7 is formed as the base member 17b. As has been described above, the measuring electrodes 17e,17f and reference electrodes 17i,17j are provided on the base member 17b.

Among these plate-like members, the three plate-like members 17d-1,17d-2,17d-3 *arranged on the opposite side are formed as a heater base member assembly 17d*. This heater base member assembly 17d is provided with a heater 18. Describing this heater base member assembly 17d further, it has been assembled by printing the heater 18 on one of the plate-like members, for example, the plate-like member 17d-1, *fitting the heater 18 in a punched-out portion of the central plate-like member 17d-2 and then superposing the remaining plate-like member 17d-3 thereon.*

The heater 18 has a heater element 18b coated with an insulating layer 18a formed of $Al_2O_3$. The insulating layer 18a and heater element 18b are both formed by a printing technique. For the fabrication of the heater, a part of the insulating layer 18 is printed first, the heater element 18b is printed over the part of the insulating layer, and the remaining part of the insulating layer 18a is thereafter printed over the heater element.

On the other hand, the intermediately-arranged plate-like member out of the plate-like members, namely, the intermediate member 17c has the punched-out portion. By superposing these five plate-like members 17b,17c,17d-1,17d-2,17d-3, the punched-out portion forms a reference air introducing chamber 17k which is in communication with the atmosphere. In this superposed state, the reference electrodes 17i,17j are located facing the reference air introducing chamber 17k.

The first sensing element 17A and second sensing element 17B independently form voltage detection circuits.

The heater 18 is connected to a battery 24 via an unillustrated switch.

In the manner described above, it is possible to arrange and house in a compact manner the first sensing element 17A and second sensing element 17B within the single sensor element portion 17S. The above fabrication method has made it possible to provide sophisticated sensors with ease.

Since the sensing elements are both arranged under substantially the same temperature conditions, the sensor does not develop such inconvenience as experienced with the conventional dual $O_2$ sensor systems described above.

The fabrication process of the $O_2$ sensor of the stacked type, namely, the fabrication process of the thin film will next be described with reference to FIGS. 9(a)-9(e) and FIGS. 10(a)-10(e).

Figure 9A:
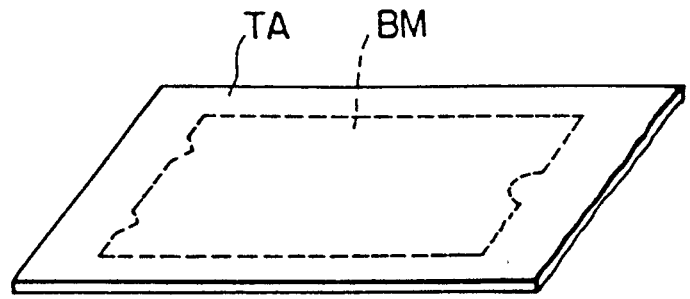
FIGS. 9(a) through 9(e) depicts the $O_2$ sensor in various steps of its fabrication process.
Figure 10A:
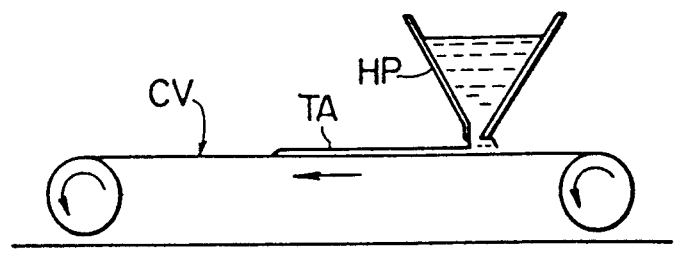
FIGS. 10(a) through 10(e) illustrate the various steps of the fabrication process by making them correspond to FIGS. 9(a) through 9(e)

First of all, a board BM as a stock material for the plate-like members 17b,17c,17d-1,17d-2,17d-3 is formed from a tape TA [see FIG. 9(a)]. FIG. 10(a) is a schematic illustration showing the manner for forming the tape TA. A mixture of powder of a solid electrolyte (ceramic powder), an organic binder and a solvent is charged in a hopper HP and is then fed onto a conveyor CV through a slit formed at a lower extremity of the hopper HP, whereby the tape TA is formed.

Figure 9B:
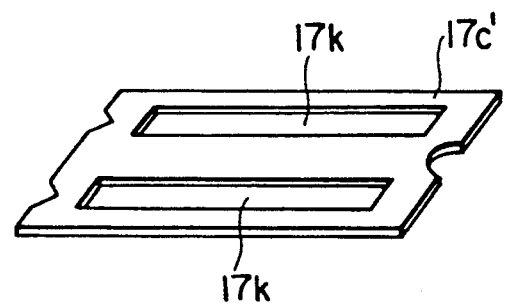
Figure 10B:
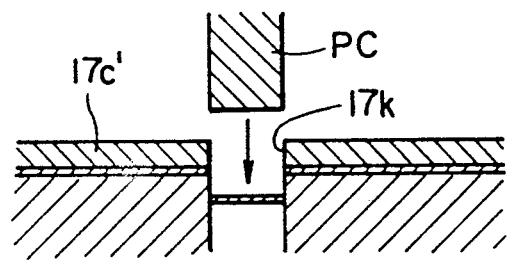

A portion of the board, which becomes the reference air introducing chamber 17k, is punched out by a punch PC, thereby forming a board 17c' for the intermediate member [see FIG. 9(b) and FIG. 10(b)].

Figure 9C:
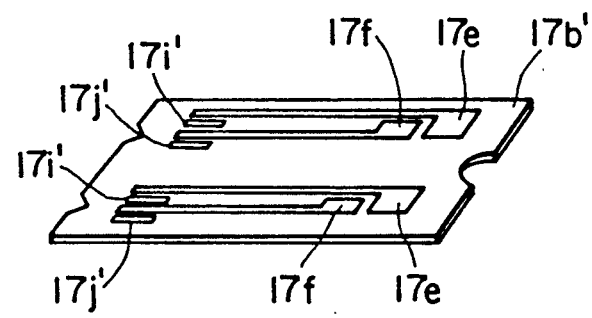
Figure 10C:
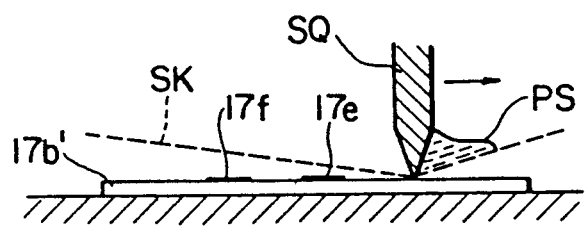

Along with this step, as shown in FIG. 9(c) and FIG. 10(c), a screen SK defining a desired printing pattern cut out therethrough is applied to one side of another board and a squeegee SQ is moved to coat the surface of the board with a paste PS. The first and second measuring electrodes 17e,17f are printed on the surface of the board, and the reference electrodes 17i, 17j are also printed on the opposite side of the board in the same manner. Regarding this board, the coating layer 17g is then printed over the measuring electrodes in the same manner. Likewise, the catalyst layer 17h is also printed to cover the second measuring electrode 17f. A board 17b' for the base member has now been formed. Incidentally, conductor portions 17i',17j' which should be electrically connected to the reference electrodes 17i,17j respectively are printed similarly on the surface of the board 17b', said surface being on the side of the measuring electrodes. Holes are then formed through the board 17b' to electrically connect the conductor portions 17i',17j' to lead portions of the corresponding reference electrodes 17i,17j, respectively.

Along with the step in which a board 17c' for the intermediate member and another board 17b' for the base member, three boards for the heater base or a board assembly 17d' for the heater base member constructed of three boards for the heater base member is also formed. Although not illustrated in the drawings, the insulating layer 18a and heater element 18b are printed in a similar manner as in the formation of the electrodes by using the screen SK and squeegee SQ. Namely, a part of the insulating layer 18a is printed on the board, the heater element 18b is printed over the part of the insulating layer, and the remaining part of the insulating layer 18a is thereafter printed over the heater element. By the printing of the insulating layer 18a and heater element 18b, the heater 18 is fabricated by the printing technique. Thereafter, the heater is fitted in the punched-out portion of the board for the intermediate heater base member and the other board for the heater base member is superposed to form the board assembly for the heater base member. As will be described subsequently, the board assembly 17d' for the heater base member is produced at the same time as it is stacked with the board 17c' for the intermediate member and the board 17b' for the base member. In addition, an overcoat layer is also printed.

Figure 9D:
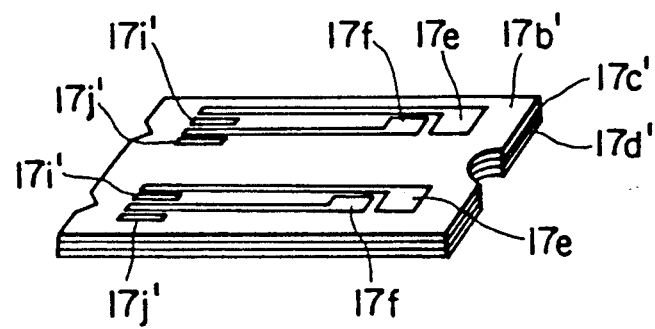
Figure 10D:
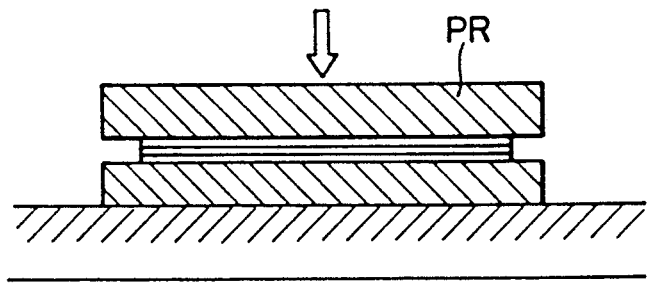

Thereafter, these boards are superposed and pressed by a press PR as shown in FIG. 10(d). By this step, the boards 17b',17c',17d' are bonded and stacked together under pressure as illustrated in FIG. 9(d).

Figure 9E:
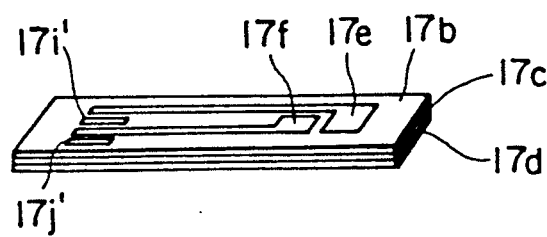
Figure 10E:
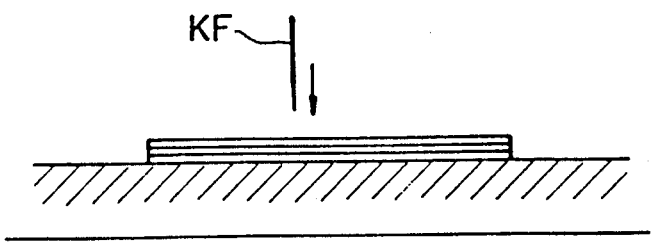

After then, as depicted in FIG. 10(e), the stacked boards shown in FIG. 9(d) are cut suitably by a knife KF. The product thus formed [see FIG. 9(e)]is then co-fired, thereby forming the sensor element portion 17S which constitutes the heart of the $O_2$ sensor.

Incidentally, the board assembly 17d' for the heater base member is illustrated as if it in the form of a single sheet in FIGS. 9(d) and 9(e). In fact, it has a three-layer structure as mentioned above.

Suitable wirings are thereafter applied to the sensor element portion 17S, followed by its packaging in a case or housing to complete the $O_2$ sensor.

Paying attention to the fabrication process of the $O_2$ sensor, the $O_2$ sensor 17 can be fabricated by only adding the printing step of the catalyst layer 17h. The $O_2$ sensor is therefore advantageous in fabrication cost compared to the conventional dual $O_2$ sensor system.

Figure 13:
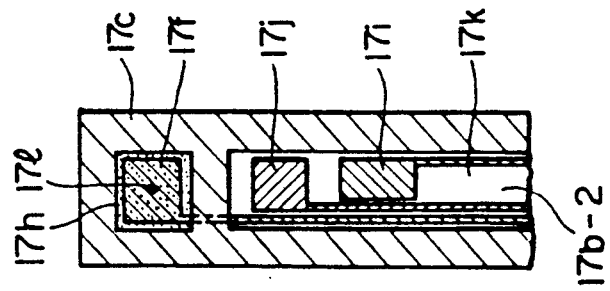
Figure 12:
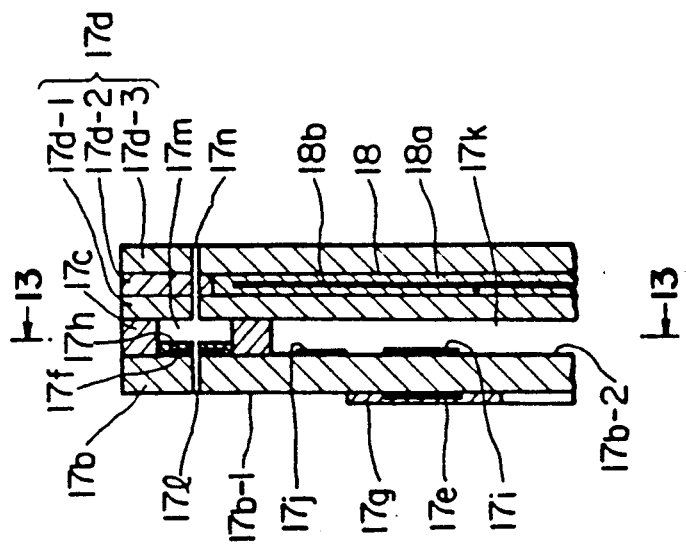
Figure 11:
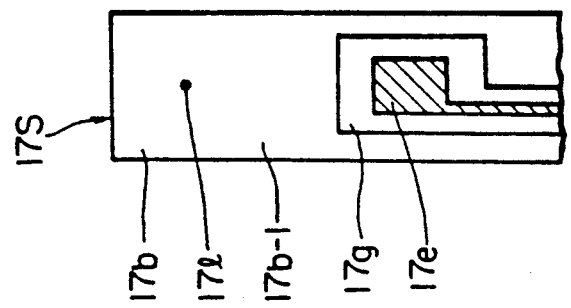

As the $O_2$ sensor 17, it is possible to use an $O_2$ sensor of a structure as shown in FIGS. 11-13 instead of using an $O_2$ sensor having such a sensor element portion as described above.

As illustrated in FIGS. 11-13, the $O_2$ sensor 17 is constructed of the base member 17b made of a solid electrolyte, the first measuring electrode 17e provided on the side wall 17b-1 of the base member 17b, said side wall 17b-1 being to be positioned on the side of exhaust gas, a diffusion chamber 17m formed in the base member 17b and adapted to receive the exhaust gas through small-diameter passages 17l,17n, the second measuring electrode 17f disposed in the diffusion chamber 17m, the catalyst 17h arranged in the diffusion chamber 17m and covering the second measuring electrode 17f, and the reference electrodes 17i,17j provided corresponding to the respective measuring electrodes 17e,17f on the wall portion 17b-2 of the base member, said wall portion 17b-2 being to be exposed to reference conditions, for example, being to be positioned on the side of the atmosphere.

The first sensing element 17A is constructed of the first measuring electrode 17e, the reference electrode 17i and the solid electrolyte (a portion of the base member 17b) located between these electrodes. The second sensing element 17B is constructed of the second measuring electrode 17f having the catalyst layer 17h, the reference electrode 17j and the solid electrolyte (another portion of the base member 17b) located substantially between these electrodes.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the catalyst layer 17h while its responsibility is slower relative to the first sensing element. Therefore, it is also possible to exclude non-equilibrated components which are contained in exhaust gas and would otherwise reach the electrode, thereby making it possible to shift the static $\lambda$ point toward the stoichiometric point, in other words, to reduce variations of the static $\lambda$ point and dynamic $\lambda$ point. Namely, the second sensing element 17B can also show exactly the same function as the conventional rearward $O_2$ sensor although it is located on the upstream side of the catalytic converter 9.

The $O_2$ sensor 17 is also constructed as an $O_2$ sensor of the stacked type. Namely, the $O_2$ sensor 17 has been formed by stacking five plate-like members 17b,17c,17d-1,17d-2,17d-3 which are each made of a solid electrolyte such as $ZrO_2$. Of these plate-like members, the one arranged on the most left-hand side as viewed in FIG. 12 is formed as the base member 17b. As has been described above, the measuring electrodes 17e,17f and reference electrodes 17i,17j are provided on the base member 17b.

Among these plate-like members, the three plate-like members 17d-1,17d-2,17d-3 arranged on the opposite side are formed as the heater base member assembly 17d. This heater base member assembly 17d is provided with the heater 18. Describing this heater base member assembly 17d further, it has been assembled by printing the heater 18 on one of the plate-like members, for example, the plate-like member 17d-1, fitting the heater 18 in the punched-out portion of the central plate-like member 17d-2 and then superposing the remaining plate-like member 17d-3 thereon.

The heater 18 has the heater element 18b coated with the insulating layer 18a formed of $Al_2O_3$. The insulating layer 18a and heater element 18b are both formed by a printing technique. For the fabrication of the heater, a part of the insulating layer 18 is printed first, the heater element 18b is printed over the part of the insulating layer, and the remaining part of the insulating layer 18a is thereafter printed over the heater element.

On the other hand, the intermediately-arranged plate-like member out of the plate-like members, namely, the intermediate member 17c has two punched-out portions. By superposing these five plate-like members 17b,17c,17d-1,17d-2,17d-3, one of the punched-out portions forms the reference air introducing chamber 17k communicated to the atmosphere and the other punched-out portion forms the diffusion chamber 17m. In this superposed state, the reference electrodes 17i,17j are located facing the reference air introducing chamber 17k and the second measuring electrode 17f is positioned facing the diffusion chamber 17m.

Here again, the first sensing element 17A and second sensing element 17B independently form voltage detection circuits. The heater 18 is connected to the battery 24 via the unillustrated switch.

In the manner described above, it is possible to arrange and house in a compact manner the first sensing element 17A and second sensing element 17B within the single sensor element portion 17S. The above fabrication method has also made it possible to provide a sophisticated sensor with ease.

Since the sensing elements are both arranged under substantially the same temperature conditions, the sensor does not develop such inconvenience as experienced with the conventional dual $O_2$ sensor systems described above.

The fabrication process of the $O_2$ sensor 17, namely, the fabrication process of the thin film will next be described with reference to FIGS. 14(a)-14(e).

Figure 14A:
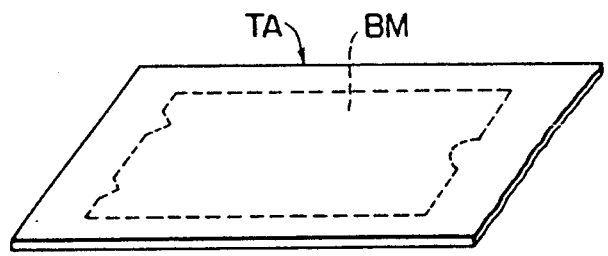
FIGS. 14(a) through 14(f) illustrate the O₂ sensor in various steps of its fabrication process.

First of all, the board BM as the stock material for the plate-like members 17b,17c,17d-1,17d-2,17d-3 is formed from the tape TA [see FIG. 14(a)].

Figure 14B:
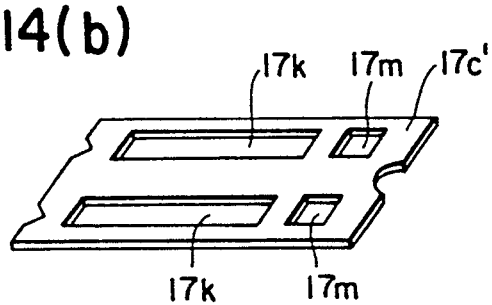

The portions of the board, which become the reference air introducing chamber 17k and diffusion chamber 17m respectively, are punched out by the punch PC, thereby forming a board 17c' for the intermediate member [see FIG. 14(b)].

Figure 14C:
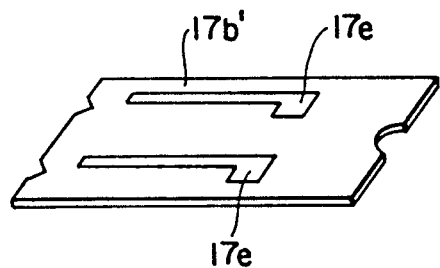

Along with this step, as shown in FIG. 14(c), a screen SK defining a desired printing pattern cut out therethrough is applied to one side of another board and the squeegee SQ is moved to coat the surface of the board with the paste PS [this procedure is the same as that shown in FIG. 10(a)]. As illustrated in FIG. 14(d), the first measuring electrode 17e is printed on the surface of the board, and the second measuring electrode 17f and reference electrodes 17i,17j are also printed on the opposite side of the board in the same manner. Regarding this board, the coating layer 17g is then printed over the first measuring electrode 17e in the same manner. Likewise, the catalyst layer 17h is also printed to cover the second measuring electrode 17f. The board 17b' for the base member has now been formed.

Along with the step in which the board 17c' for the intermediate member and the board 17b' for the base member, three boards for the heater base or the board assembly 17d' for the heater base member constructed of three boards for the heater base member is also formed. Although not illustrated in the drawing, these steps are similar to the above-described embodiment and their description is omitted herein.

Figure 14E:
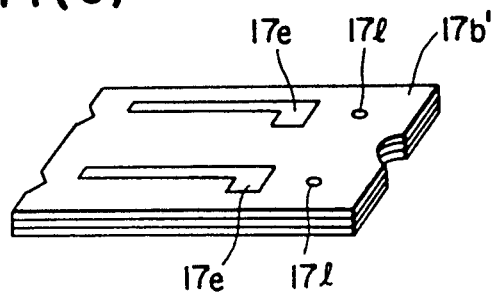

Thereafter, these boards are superposed and pressed By this step, the boards 17b',17c',17d' are bonded and stacked together under pressure as illustrated in FIG. 14(e).

After then, the stacked boards shown in FIG. 14(e) are cut suitably by a knife. The product thus formed [see FIG. 14(f)]is then co-fired, thereby forming the sensor element portion 17S which constitutes the heart of the $O_2$ sensor 17.

Figure 14F:
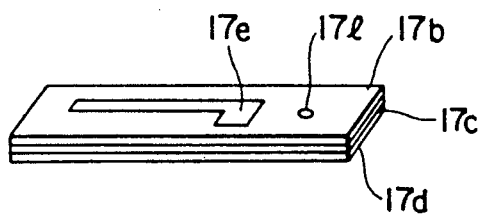
Figure 14D:
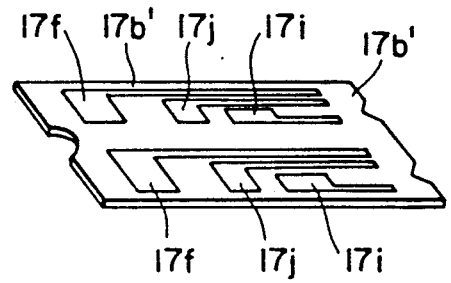

By the way, FIGS. 14(e) and 14(f) illustrate the board assembly 17d' for the heater base member as if it a single sheet. However, the board assembly 17d' actually has the three-layer structure as described above.

Suitable wirings are then applied to the sensor element portion 17S, followed by package of the sensor element portion 17S in a casing or housing to complete the $O_2$ sensor 17.

Paying attention to the fabrication process of the $O_2$ sensor, the punching of the diffusion chamber 17m is conducted at the same time as the punching of the reference air introducing chamber 17k. No additional step is therefore needed practically. Correctly speaking, the $O_2$ sensor 17 can be fabricated by only adding the printing step of the catalyst layer 17h. The $O_2$ sensor is therefore advantageous in fabrication cost compared to the conventional dual $O_2$ sensor system.

As the $O_2$ sensor 17, it is possible to use an $O_2$ sensor of a still different structure as shown in FIGS. 15-17 instead of using an $O_2$ sensor having such a sensor element portion as described above.

As illustrated in FIGS. 15-17, the $O_2$ sensor 17 of the still different structure is constructed of the base member 17b made of the solid electrolyte, the first measuring electrode 17e provided on the side wall 17b-1 of the base member 17b, said side wall 17b-1 being to be positioned on the side of exhaust gas, the diffusion chamber 17m formed in the base member 17b and adapted to receive the exhaust gas through small-diameter passages 17l,17n, the second measuring electrode 17f disposed in the diffusion chamber 17m and having catalytic ability, and the reference electrodes 17i,17j provided corresponding to the respective measuring electrodes 17e,17f on the wall portion 17b-2 of the base member 17b, said wall portion 17b-2 being to be exposed to reference conditions, for example, being to be positioned on the side of the atmosphere.

The first sensing element 17A is constructed of the first measuring electrode 17e, the reference electrode 17i and the solid electrolyte (a portion of the base member 17b) located between these electrodes. The second sensing element 17B is constructed of the second measuring electrode 17f having the catalytic ability, the reference electrode 17j and the solid electrolyte portion (another portion of the base member 17b) located substantially between these electrodes.

As also envisaged from FIG. 15 through FIG. 17, the $O_2$ sensor is different only at the portion of the second measuring electrode 17f compared to the $O_2$ sensor 17 shown in FIGS. 11-14. Namely, in the $O_2$ sensor 17 depicted in FIGS. 11-14, the second measuring electrode 17f is covered by the catalyst 17h. In the $O_2$ sensor 17 shown in FIGS. 15-17, the second measuring electrode 17f is not covered by any catalyst but the electrode itself has catalytic ability.

Accordingly, the first sensing element 17A is constructed as a sensing element concentrating the importance on the responsibility, in other words, having small catalytic ability like the conventional art. On the other hand, the second sensing element 17B has catalytic ability improved over the first sensing element owing to the provision of the measuring electrode 17f having large catalytic ability while its responsibility is slower relative to the first sensing element.

Therefore, it is also possible to exclude by the second sensing element 17B non-equilibrated components which are contained in exhaust gas and would otherwise reach the electrode, thereby making it possible to shift the static λ point toward the stoichiometric point, in other words, to reduce variations of the static λ point and dynamic λ point. Namely, the second sensing element 17B can also show exactly the same function as the conventional rearward $O_2$ sensor although it is located on the upstream side of the catalytic converter 9.

The manner of fabrication of the $O_2$ sensor 17 shown in FIGS. 15-17 is similar to that illustrated in FIGS. 14(a)-14(f). The merits of the fabrication process shown in FIGS. 14(a)-14(f) can also be obtained similarly.

Incidentally, hatching is applied to each electrode in FIGS. 6, 11, 13, 15 and 17. This hatching however does not indicate a cross-section but has been applied to show the existence of the electrode.

Instead of providing the reference electrodes 17i,17j separately corresponding to the first and second measuring electrodes 17e,17f, a single reference electrode may be provided commonly to the measuring electrodes.

Figure 1B:
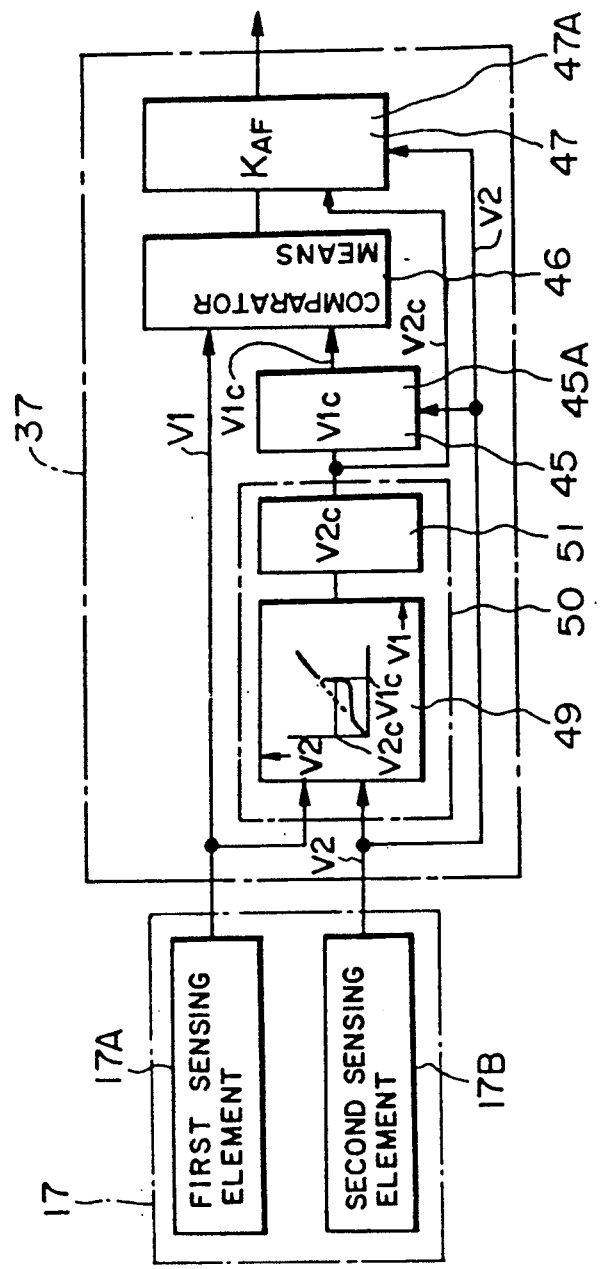
FIG. 1(b) is a fragmentary block diagram of the control system.
Figure 2:
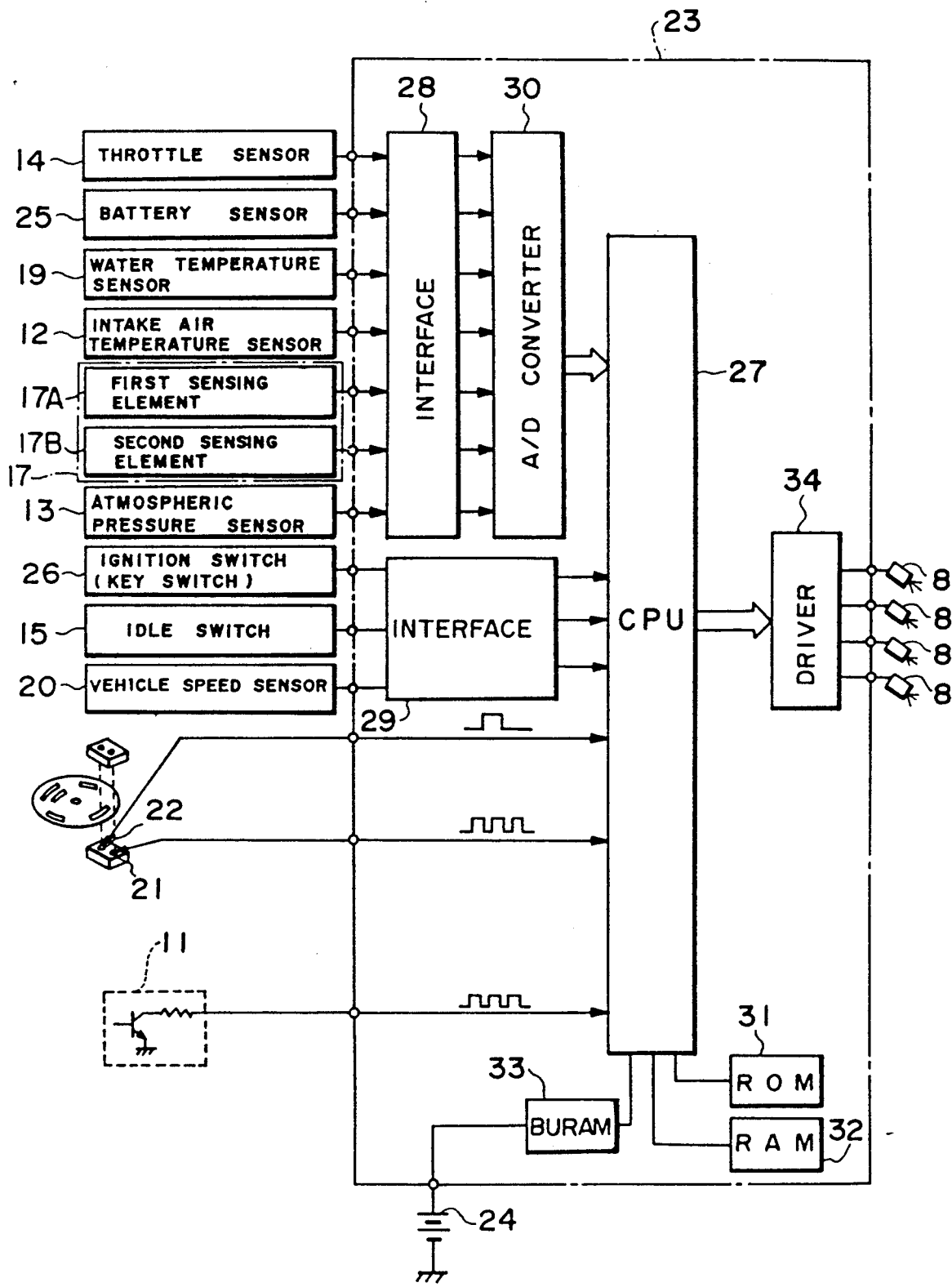

As shown in FIGS. 1(a), 2 and 3, a water temperature sensor 19 for detecting the temperature of the cooling water for the engine and a vehicle speed sensor 20 for detecting the vehicle speed are provided as other sensors. In addition, a crank angle sensor 21 for detecting the crank angle (which also serves as a revolutionary speed sensor for detecting the revolutionary speed of the engine) and a TDC sensor 22 for detecting the top dead center of a first cylinder (base cylinder) are both provided with the distributor.

Detection signals from these sensors 11-22 are inputted to an electronic control unit (ECU) 23.

Also inputted to the ECU 23 are a voltage signal from a battery sensor 25 for detecting the voltage of a battery 24 and a signal from an ignition switch (key switch) 26.

The hardware construction of the ECU 23 may be illustrated as shown in FIG. 2. The ECU 23 is equipped with a CPU 27 as its main element. The CPU 27 is fed with detection signals from the intake air temperature sensor 12, barometric sensor 13, throttle sensor 14, $O_2$ sensor 17 (first sensing element 17A and second sensing element 17B), water temperature sensor 19 and battery sensor 25 by way of an input interface 28 and/or an A/D converter 30. Detection signals from the idle sensor 15, vehicle speed sensor 20 and ignition switch 26 are also inputted through an input interface 29, while detection signals from the air flow sensor 11, crank angle sensor 21 and TDC sensor 22 are inputted directly to the input port.

Via bus lines, the CPU 27 performs transfer of data with an ROM 31 which serves to store program data and fixed-value data, an RAM 32 which is renewed and rewritten sequentially, and a battery backed-up RAM (BURAM) 33 which is backed up by the battery 24 to maintain its contents while the battery 24 is connected.

Incidentally, the RAM 32 is designed in such a way that data stored therein are erased and reset when the ignition switch 26 is turned off.

Let's now pay attention only to the control of fuel injection (air/fuel ratio control). A fuel injection control signal which has been computed in a manner to be described subsequently is outputted via a driver 34, whereby the 4 solenoid valves 8 by way of example are successively actuated.

A function block diagram of such a fuel injection control (the control of the drive time of each solenoid valve) may be illustrated as shown in FIG. 1(a). Let's now make a discussion on the ECU 23 from the standpoint of its software. First of all, the ECU 23 is equipped with a basic energization time determination means 35 for determining the basic drive time $T_B$ for the solenoid valves 8. The basic energization time determination means 35 determines information on the intake air volume per revolution of the engine (Q/Ne) on the basis of information on an intake air quantity Q from the airflow sensor 11 and information on engine revolutionary speed Ne from the crank angle sensor 21 and then determines a basic drive time $T_B$ on the basis of the information.

There are also provided an air/fuel ratio upward correction means 36 for performing an upward correction of the air/fuel ratio in accordance with the revolutionary speed of the engine and the engine load (the above Q/Ne information contains engine load information) and an $O_2$ sensor feedback correction means 37 for conducting corrections of the $O_2$ sensor by setting a correction factor $K_{AF}$ upon performing the feedback control of the $O_2$ sensor. Either one of the air/fuel ratio upward correction means 36 and $O_2$ sensor feedback correction means 37 is selected by switching means 38,39 which are changed over in a mutually-interlocked manner.

Also provided are a water-temperature-dependent correction means 40 for setting a correction factor $K_{WT}$ in accordance with the temperature of the cooling water for the engine, an intake-air-temperature-dependent correction means 41 for setting a correction factor $K_{AT}$ in accordance with the temperature of the air drawn, a barometric-pressure-dependent correction means 42 for setting a correction factor $K_{AP}$ in accordance with the barometric pressure, an accelerating-fuel-increment correction means 43 for setting a correction factor $K_{AC}$ for the increment of fuel quantity for acceleration, and a dead time correction means 44 for setting a dead time (ineffective time) $T_D$ for correcting the drive time in accordance with the voltage of the battery. During $O_2$ feedback control, the drive time $T_{INJ}$ of the solenoid valve 8 is eventually expressed by $T_B \times K_{WT} \times K_{AT} \times K_{AP} \times K_{AC} \times K_{AF} + T_D$ and the solenoid valve 8 is actuated for the drive time $T_{INJ}$.

Figure 19:
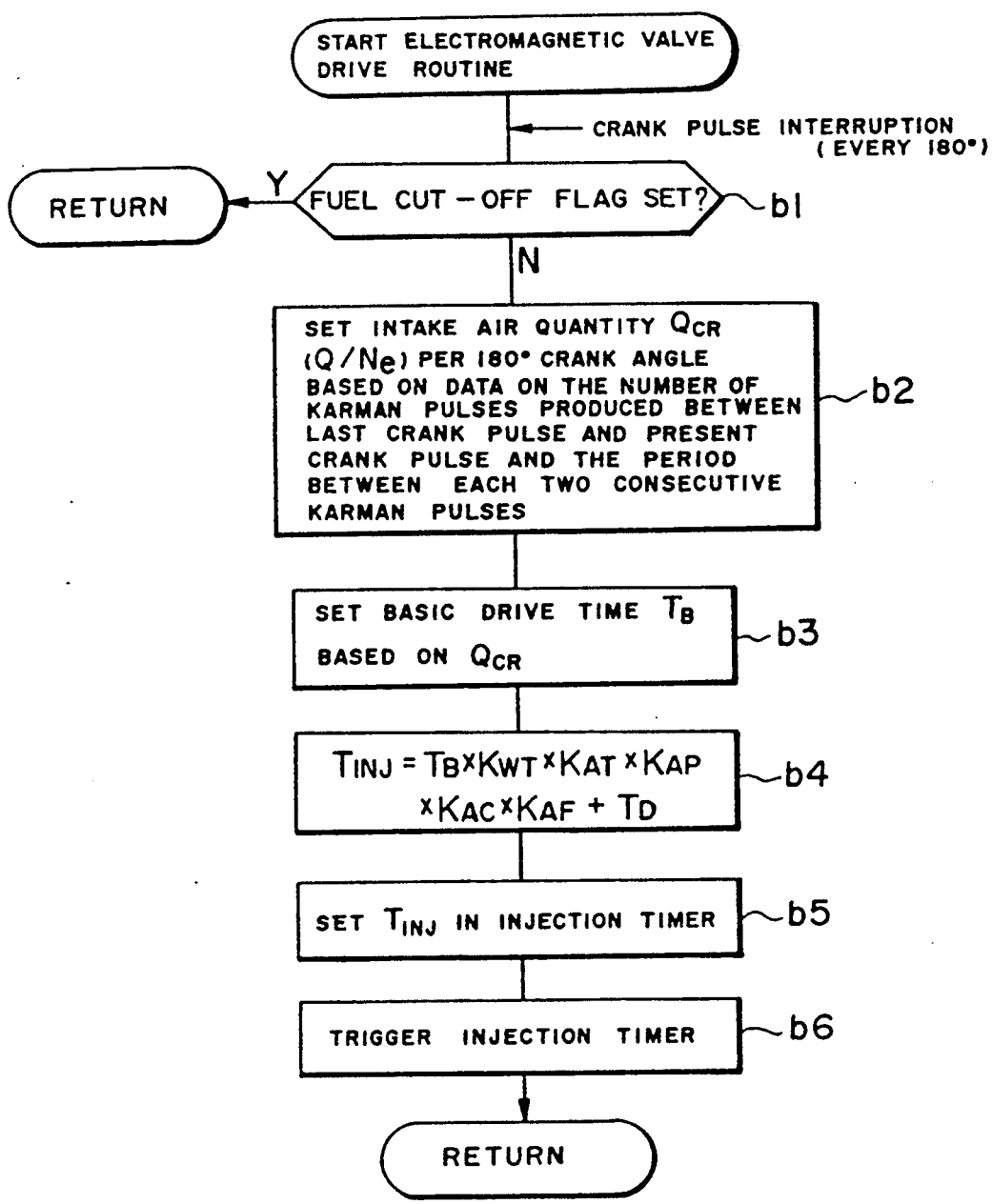

The procedure of such a control of the actuation of the solenoid valve may be illustrated like the flowchart of FIG. 19. The routine of the flow chart shown in FIG. 19 is performed by a crank pulse interruption which takes place every 180°. First of all, it is judged in Step b1 whether a fuel cut-off flag has been set up or not. Where the fuel cut-off flag has been set up, no fuel injection is required and the routine returns. Otherwise, an intake air quantity $Q_{CR}(Q/Ne)$ per 180° crank angle is set up in Step b2 on the basis of data on the number of Karman pulses produced between the last crank pulse and the present crank pulse and the period between the Karman pulses.

The routine then advances to Step b3, where the basic drive time $T_B$ is set up in accordance with the $Q_{CR}$. The solenoid valve drive time $T_{INJ}$ is then determined in Step b4 by computing it in accordance with $T_B \times K_{WT} \times K_{AT} \times K_{AP} \times K_{AC} \times K_{AF} + T_D$. The $T_{INJ}$ is set in an injection timer in Step b5 and is then triggered in Step b6. By this trigger, the fuel is injected only for the time $T_{INJ}$.

During the air/fuel ratio feedback control making use of the $O_2$ sensor, an output V1 from the first sensing element 17A of the $O_2$ sensor 17 is compared with a predetermined standard value $V1_c$, which is selected at an intermediate level between a high-level output and a low-level output of the first sensing element 17A and functions as a so-called rich/lean judgement voltage. The air-fuel mixture is rendered richer when $V1_c > V1$ but is rendered leaner when $V1_c \leq V1$.

Accordingly, the $O_2$ sensor feedback correction means 37 has, as depicted in FIG. 1(b), a rich/lean judgement voltage setting means 45 for setting the standard value $V1_c$, a comparator means 46 for comparing the output V1 from the first sensing element 17A with the standard value $V1_c$ from the rich/lean judgement voltage setting means 45, and a correction factor determination means 47 for determining the air/fuel ratio correction factor $K_{AF}$ in accordance with comparison results from the comparator means 46. The present air/fuel ratio control system is equipped with a standard value changing means 50 for allowing to change the standard value $V1_c$ for the first sensing element and the standard value $V2_c$ for the second sensing element (a second standard value for the second sensing element) on the basis of the outputs V1 and V2 from the first sensing element 17A and second sensing element 17B, for example, for every predetermined drive distance.

A description will next be made of reasons for which the standard value can be changed and corrected to a more reasonable rich/lean judgement voltage $V1_c$ on the basis of both the outputs V1 and V2 from the first sensing element 17A and second sensing element 17B.

Let's now plot outputs V1 of the first sensing element 17A along the axis of abscissas and outputs V2 of the second sensing element 17B along the axis of ordinates so as to determine the relation between both the outputs V1 and V2. They are found to have such characteristics as shown by a solid curve in FIG. 27(b). When such characteristics is compared with the characteristics of $NO_x$ cleaning efficiency [see FIG. 27(a), solid curve] and the characteristics of CO·HC cleaning efficiency [see FIG. 27(a), broken curve], it is appreciated that an output value $V1_c$ of the first sensing element 17A giving the maximum cleaning efficiencies shown in FIG. 27(a) (i.e., at the stoichiometric air/fuel ratio) coincides with an output value $V1_c$ of the first sensing element 17A at which the characteristics depicted in FIG. 27(b) change abruptly.

An air/fuel ratio at which V2 changes extremely great relative to a change of the output V1 has been found to be an air/fuel ratio capable of giving high cleaning efficiencies for the three components of HC, CO and $NO_x$ (i.e., the stoichiometric air/fuel ratio), irrespective of variations in characteristics from one $O_2$ sensor to another, changes of the characteristics of each $O_2$ sensor along the passage of time, and the like.

The output characteristics of the first sensing element 17A and second sensing element 17B are illustrated as shown in FIG. 27(b) for the following reasons. When unburnt components such as CO are contained in an exhaust gas, the level of the O₂ sensor increases. Even when the air/fuel ratio is lean, the output of the first sensing element 17A increases for the same reasons because unburnt gases such as HC, CO and H₂ exist on the upstream side of the catalytic converter 9. On the other hand, the output of the second sensing element 17B does not increase since such unburnt gases have been cleaned by the catalytic converter 9. Since these relationship becomes very clear in the vicinity of the stoichiometric air/fuel ratio, characteristics such as those depicted in FIG. 27($b$) are obtained.

For the reasons mentioned above, the standard value changing means 50 is equipped with a characteristics computing means 49 which is adapted to compute the characteristics in relationship between the output of the first sensing element 17A and that of the second sensing element 17B as depicted in FIG. 27($b$). A standard value $V1_c$ of the first sensing element 17A, which has been determined by the characteristic computing means 49, is stored as a new standard value $V1_c$ and at the same time, a standard value of the second sensing element 17B is stored as a new standard value $V2_c$. The function of renewal of the standard value $V1_c$ for the first sensing element 17A is provided with the rich/lean judgement voltage setting means 45, while the function of renewal of the standard value $V2_c$ for the second sensing element 17B is provided with the standard value setting means 51.

Further, a standard value $V2_c$ signal from the standard value setting means 51 is inputted to the rich/lean judgement voltage setting means 45 and correction factor determination means 47. These rich/lean judgement voltage setting 45 and correction factor determination means 47 also function respectively as air/fuel ratio control correction means 45A,47A for effecting a correction to the air/fuel ratio control which is performed by the air/fuel control means on the basis of the results of a comparison between the standard value $V2_c$ for the second sensing element and the output V2 from the second sensing element 17B. Namely, the air/fuel ratio control correction means 45A in the rich/lean judgement voltage setting means 45 can correct the rich/lean judging standard value $V1_c$ on the basis of the deviation $\Delta V$ between the standard value $V2_c$ for the second sensing element and an output V2 of the second sensing element 17B measured during the air/fuel feedback control. On the other hand, the air/fuel ratio control correction means 47A of the correction factor determination means 47 can correct any of the response delay times DLYRL,DLYLR, proportional gains $P_{RL},P_{LR}$ and integral gains $I_{RL},I_{LR}$ on the basis of the deviation $\Delta V$ between the standard value $V2_c$ for the second sensing element and an output V2 of the second sensing element 17B measured during the air/fuel feedback control.

Incidentally, the V2-V1 characteristics, the rich/lean judgement voltage $V1_c$ which has been corrected based on the standard values $V1_c,V2_c$ or the output V2 from the second sensing element 17B, the response delay times DLYRL,DLYLR, the proportional gains $P_{RL},P_{LR}$ and the integral gains $I_{RL},I_{LR}$ are stored in the BURAM 33.

The main routine of the air/fuel ratio control system, which includes the above-described changing of the standard value, the determination of the correction factor and the like, will next be described with reference to FIGS. 18($a$) through 18($e$). Although these FIGS. 18($a$) through 18($e$) illustrate a single flow chart, the flow chart is very long and for the sake of convenience, has hence been divided at the appropriate parts into the four figures.

In the main flow, the routine is started firstly as depicted in FIG. 18($a$) when a key switch (ignition switch) is turned on. First of all, the RAM 32 and interfaces are initialized in Step a1. It is next judged in Step a2 whether the battery 24 has been disconnected or not. Since the battery 24 is kept connected generally, the NO route is followed and a drive distance datum OD is inputted in Step a3.

The routine then advances to Step a4, where the OD datum is compared with a standard-value-rewriting distance ODX which is backed up by the battery. When not OD>ODX, namely, the drive distance has not yet reached the standard-value-rewriting distance, operational state information is inputted in Step a5. In the next Step a6, it is judged whether the operational state is in a fuel cut-off zone or not. When it is not in the fuel cut-off zone, a fuel cut-off flag is reset in Step a7, followed by setting of the correction factors $K_{WT}$, $K_{AT}$, $K_{AP}$ and $K_{AC}$ in Step a8. The dead time $T_D$ is then set in Step a9. These factors are set by the cooling-water-temperature-dependent correction means 40, intake-air-temperature-dependent correction means 41, barometric-pressure-dependent correction means 42, accelerating fuel-increment correction means 43 and dead time correction means 44, respectively.

In Step a10, it is next judged from the output voltage value of the first sensing element 17A whether the first sensing element is in an active state or not.

If the first sensing element 17A is active, the routine advances to the next Step a12 [see FIG. 18($b$)] in which a judgement is made to determine whether it is in the air/fuel ratio (A/F) feedback mode or not.

In the case of the A/F feedback mode, it is judged in Step a13 whether a completion flag for the checking of the O₂ sensor correction has been set or not. Since the completion flag has been set usually, the routine therefore advances along the YES route, and in Step a14, the output V1 of the first sensing element 17A and the rich/lean judgement voltage $V1_c$ are compared with each other. When $V1_c>V1$, it is judged in Step a15 whether a without feedback flag (hereinafter called "WOFB flag") has been set or not. Since WOFB flag is in a set state at the time point immediately after the A/F feedback zone has been entered, the routine takes the YES route, the proportional gain P is changed to 0 in Step a16-1, WOFB flag is reset in Step a16-2, and Flag L is changed to 1 in Step a16-3. Here, Flag L indicates enrichment by 1 and leanness by 2.

After Step a16-3, the feedback correction factor $K_{FB}$ is determined as $1+P+I$ in Step a17 and this value $K_{FB}$ is inputted to an address $K_{AF}$ in Step a21. At the beginning, the proportional gain P=0 and the integral factor I=0. The routine therefore starts with $K_{FB}=1$.

Therefore, it is judged in Step a23-2 whether a completion flag for the checking of O₂ sensor correction has been set or not. Since the completion flag is in a set state, the routine takes the YES route and returns to Step a5.

When the routine has returned again to Step a15, the NO route is taken this time since WOFB flag has been reset in Step a16-2. In Step a16-4, it is judged whether Flag L is 1 or not. When L is judged to be 1 in Step a16-3, the YES route is taken to perform the processing of Step a17.

Figure 20B:
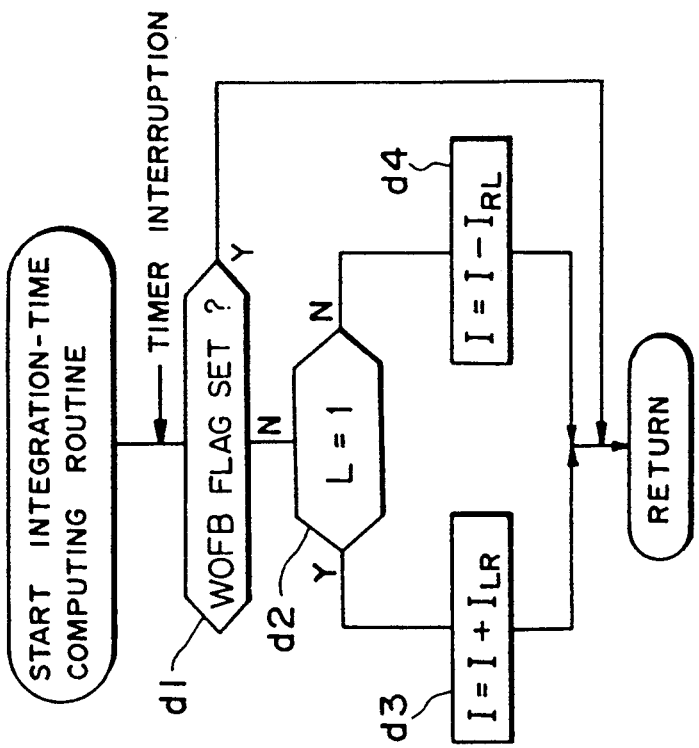
FIG. 20(b) is a flow chart for illustrating an integration time computing routine for the control system.

Incidentally, the integration-time computing routine for the integral factor I can be illustrated like the flow chart of FIG. 20(b). In this routine, at every interruption of the timer, it is judged in Step d1 whether WOFB flag has been set or not. When WOFB flag has been found to be reset (when the operation is in the A/F feedback mode), it is judged in Step d2 whether Flag L is 1 or not. If L=1, the sum of I and $I_{LR}$ (an integral factor for enrichment) is obtained newly as I in Step d3. Unless L=1, the difference obtained by subtracting $I_{RL}$ (an integral factor for leanness) is obtained newly as I in Step d4. $I_{LR}$ is therefore added at every timer interruption while L=1. While L is not 1 (i.e., L=2), $I_{RL}$ is subtracted at every time interruption. Accordingly, the feedback correction factor $K_{FB}$ becomes greater while $I_{LR}s$ are added successively, so that the enrichment is promoted further. While $I_{RL}s$ are subtracted successively, the feedback correction factor $K_{FB}$ becomes smaller so as to promote the leanness.

Since L=1 in this case, $I_{LR}$ is added at every time interruption and the feedback correction factor $K_{FB}$ becomes greater. The enrichment is therefore promoted.

When $V1_c$ becomes equal to or smaller than V1 ($V1_c \leq V1$) as a result of enrichment in the abovedescribed manner, the NO route is taken in Step a14, and it is judged in Step a18 whether WOFB flag has been set or not. When the operation is still in the A/F feedback mode, WOFB flag is still in the reset state. The NO route is therefore followed in Step a18, and in Step a19-1, a judgement is made to determine whether Flag L is 2 or not. Since L=1 immediately after the switching, the NO route is taken in Step a19-1. In Step a19-1' subsequent to the attainment of ($V1_c \leq V1$), it is judged whether the delay time DLYLR has lapsed or not. While the delay time DLYLR has not lapsed, the NO route is taken to perform the processing of Step a17. After the delay time DLYLR has lapsed, the YES route is then taken and the proportional gain $P_{RL}$ for leanness is subtracted from the proportional gain P in Step a19-2. The difference is then set as P. After changing L to 2 (L=2) in Step a19-3, the feedback correction factor $K_{FB}$ is determined as 1+P+I in Step a17. This value $K_{FB}$ is inputted to the address $K_{AF}$ in Step a21. As a result, the feedback correction factor $K_{FB}$ is decreased by the proportional gain $P_{RL}$ for leanness from its maximum value.

Thereafter, the routine returns to Step a5 in the same manner as described above.

When the routine has returned again to Step a19-1 via Step a18, the YES route is taken this time because L has been changed to 2 in Step a19-3. The processing of Step a17 is therefore applied.

Since L=2 in this case, at every timer interruption, the NO route is taken in Step d2 of FIG. 20(b) and $I_{RL}$ is subtracted in Step d4 of the same figure, and the feedback correction factor $K_{FB}$ becomes smaller. The leanness is therefore promoted.

When $V1_c$ becomes greater than V1 ($V1_c > V1$) as a result of leanness in the above-described manner, the YES route is taken in Step a14, and it is judged in Step a15 whether WOFB flag has been set or not. When the operation is still in the A/F feedback mode, WOFB flag is still in the reset state. The NO route is therefore followed in Step a15, and in Step a16-4, a judgement is made to determine whether Flag L is 1 or not. Since L=2 immediately after the switching, the NO route is taken in Step a16-4. After attainment of ($V1_c \leq V1$) in Step a16-4', it is judged whether the delay time DLYRL has lapsed or not. While the delay time DLYRL has not lapsed, the NO route is taken to perform the processing of Step a17. After the delay time DLYRL has lapsed, the YES route is taken and the proportional gain $P_{LR}$ for enrichment is added to the proportional gain P in Step a16-5 so as to use the sum as P. After changing L to 1 (L=1) in Step a16-3, the feedback correction factor $K_{FB}$ is determined as 1+P+I in Step a17. This value $K_{FB}$ is then inputted to the address $K_{AF}$ in Step a21. As a consequence, the feedback correction factor $K_{FB}$ is increased by the proportional gain $P_{LR}$ for enrichment from its maximum value.

Figure 26A:
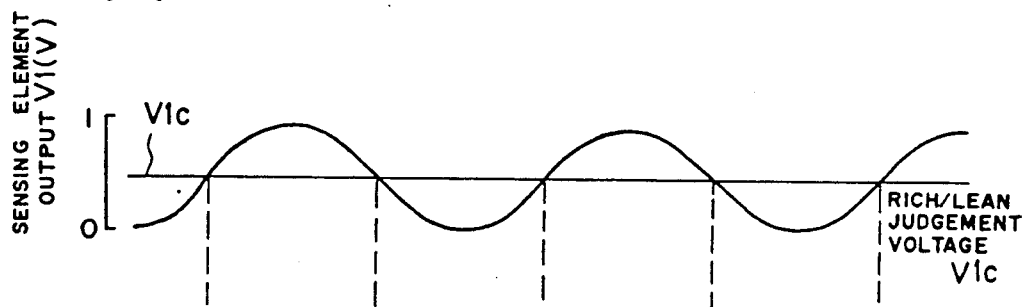
Figure 26B:
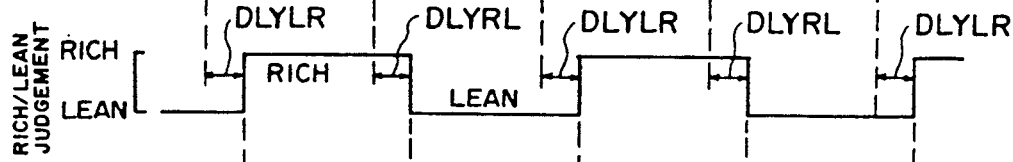
Figure 26C:
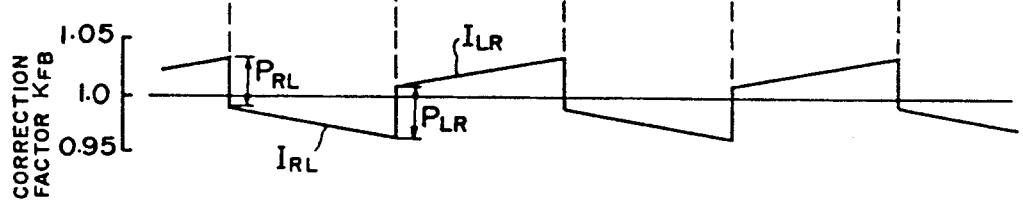

By repeating the above processing thereafter, the feedback correction factor $K_{FB}$ is varied as shown in FIG. 26(c) so that the desired air/fuel ratio control is performed in the A/F feedback mode.

Incidentally, FIG. 26(a) is a waveform diagram of the output of the first sensing element, while FIG. 26(b) is a waveform diagram for the rich/lean judgement. The delay times DLYRL,DLYLR are, as illustrated in FIG. 26(b), times corresponding to the delays until a rich/lean judgement is performed when the output of the $O_2$ sensor has crossed the rich/lean judgement voltage $V1_c$ upwardly or downwardly as illustrated in FIG. 26(a).

When $V1_c \leq V1$ immediately after entering the A/F feedback zone, the YES route is followed in Step a18 since WOFB flag is in a set state at the time point immediately after the entering. The proportional gain P is changed to 0 in Step a19-4, WOFB flag is reset in Step a19-5, and Flag L is changed to 2 in Step a19-3. After step a19-3, the feedback correction factor $K_{FB}$ is determined as 1+P+I in Step a17 and this value $K_{FB}$ is inputted to the address $K_{AF}$ in Step a21. Here again, the proportional gain P and integral factor I are both 0 (P=0, I=0) at the beginning, and the routine also starts from $K_{FB}=1$.

As has been described above, it is the comparator means 46 and correction factor determination means 47 in the $O_2$ sensor feedback correction means 37 that perform the comparison between $V1_c$ and V1 and determine the correction factor $K_{AF}$ on the basis of results of the comparison.

In the present embodiment, the delay times DLYRL,DLYLR, proportional gains $P_{RL}$,$P_{LR}$ and integral gains $I_{RL}$,$I_{LR}$ are variable as will be described subsequently.

When the operation is found to be in the fuel cut-off zone in Step a6 subsequent to Step a5 and a fuel cut-off flag is set in Step a27, the integral factor I is changed to 0 in Step a28, an initial value (for example, 10 seconds or so) is inputted to the timer $T_{KC}$ in Step a29, and a mapped A/F correction factor $K_{AFM}$ is set in accordance with the load and revolutionary speed of the engine in Step a30. The mapped A/F correction factor $K_{AFM}$ is inputted to the address $K_{AF}$ in Step a31, and after setting WOFB flag in Step a31-2, the routine returns to Step a5 via Step a23-2.

When the answer is "NO" in Step a10 or a12, it is impossible to perform the A/F feedback control. The routine therefore returns to Step a5 via Steps a28–a31, a31-2 and a23-2.

During usual driving, the above routine is performed repeatedly so as to set the factors $K_{WT}$, $K_{AT}$,$K_{AP}$,$K_{AC}$, $K_{AF}$ and the time $T_D$ in accordance with the state of the engine. By performing the solenoid valve drive routine depicted in FIG. 19 by using these values, each solenoid valve 8 is actuated to inject a desired quantity of the fuel. In this manner, the desired air/fuel ratio control is effected.

When the drive distance OD reaches the standard value rewriting distance ODX, the YES route is taken in Step a4 and the completion flag for the checking of correction of the $O_2$ sensor is reset in Step a71.

Thereafter, the routine advances through Step a5 and performs the processing of Step a6. When the operation is found to be outside the fuel cut-off zone in Step a6, the routine advances through Steps a7–a9 and the processings of Steps a10,a12 are performed. When the answer is "YES" in each of Steps a10,a12, it is judged in Step a13 whether the flag for the completion of checking of the $O_2$ sensor has been set or not. Since it has been reset in Step a71 in this case, the routine advances through the NO route and then moves to Steps a11,a32-,a33 illustrated in FIG. 18(c).

In Step a11, a judgement is made to determine whether the second sensing element 17B is in an active state or not. In Steps a32,a33, it is judged whether the revolutionary speed Ne of the engine is 3,000 rpm or lower and whether it is 1,500 rpm or higher. When both answers are "YES", it is judged in Step a34 whether the engine fluctuation $|dNe/dt|$ is smaller than a preset value $DN_x$. When it is smaller, it is judged in Steps a35,a36 whether the intake air quantity Q is greater than a preset value $Q_x$ and whether the intake air fluctuation $|dQ/dt|$ is smaller than a preset value $DQ_x$. When both answers are "YES", it is judged in Step a37 whether the fluctuation $|d\theta/dt|$ of the throttle opening rate $\theta$ is smaller than a preset value $DTH_x$. When the answer is also "YES" in Step a37, a further judgement is made in Step a39 to determine whether the timer $T_{KC}$ is 0 or not.

Figure 20A:
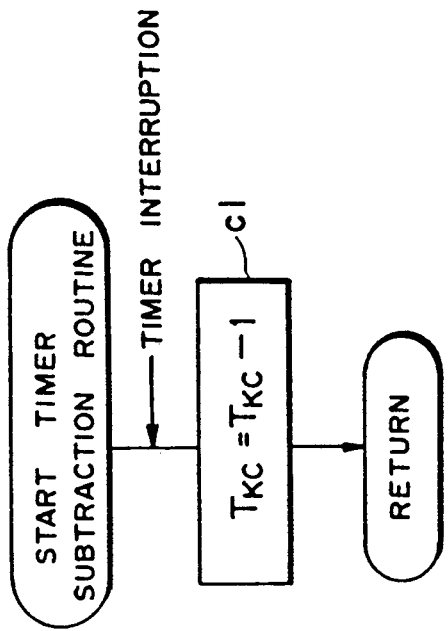
FIG. 20(a) is a flow chart for describing a timer subtraction routine for the control system.

Incidentally, the timer $T_{KC}$ is designed to operate at every timer interruption in accordance with the timer subtraction routine shown in FIG. 20(a). In Step c1, the timer subtracts 1 from the contents of $T_{KC}$ to give new contents $T_{KC}$, in other words, performs a downcount.

Figure 18A:
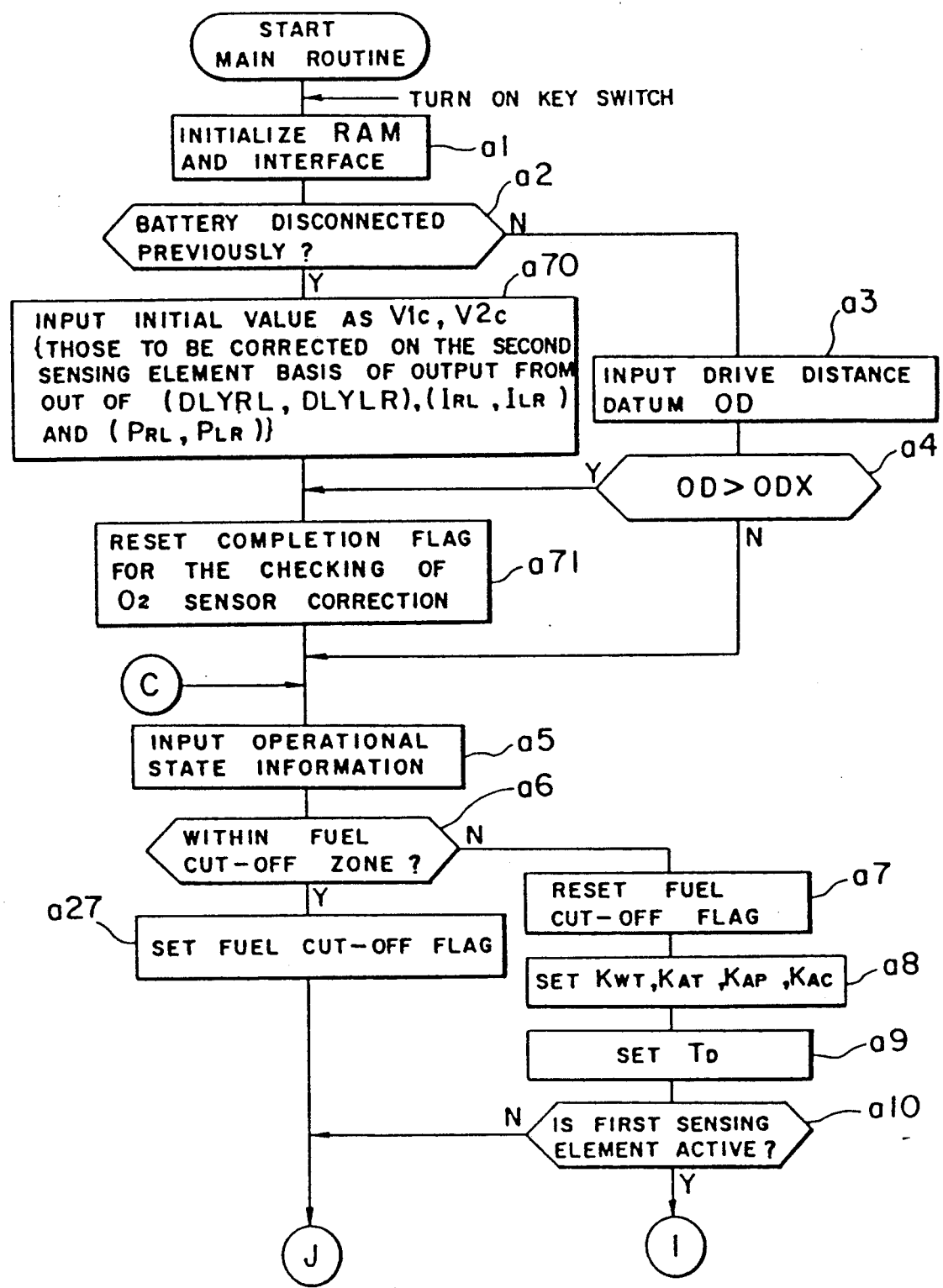
FIGS. 18(a) through 18(e) are respectively flow charts for illustrating a main routine of the control system.
Figure 18B:
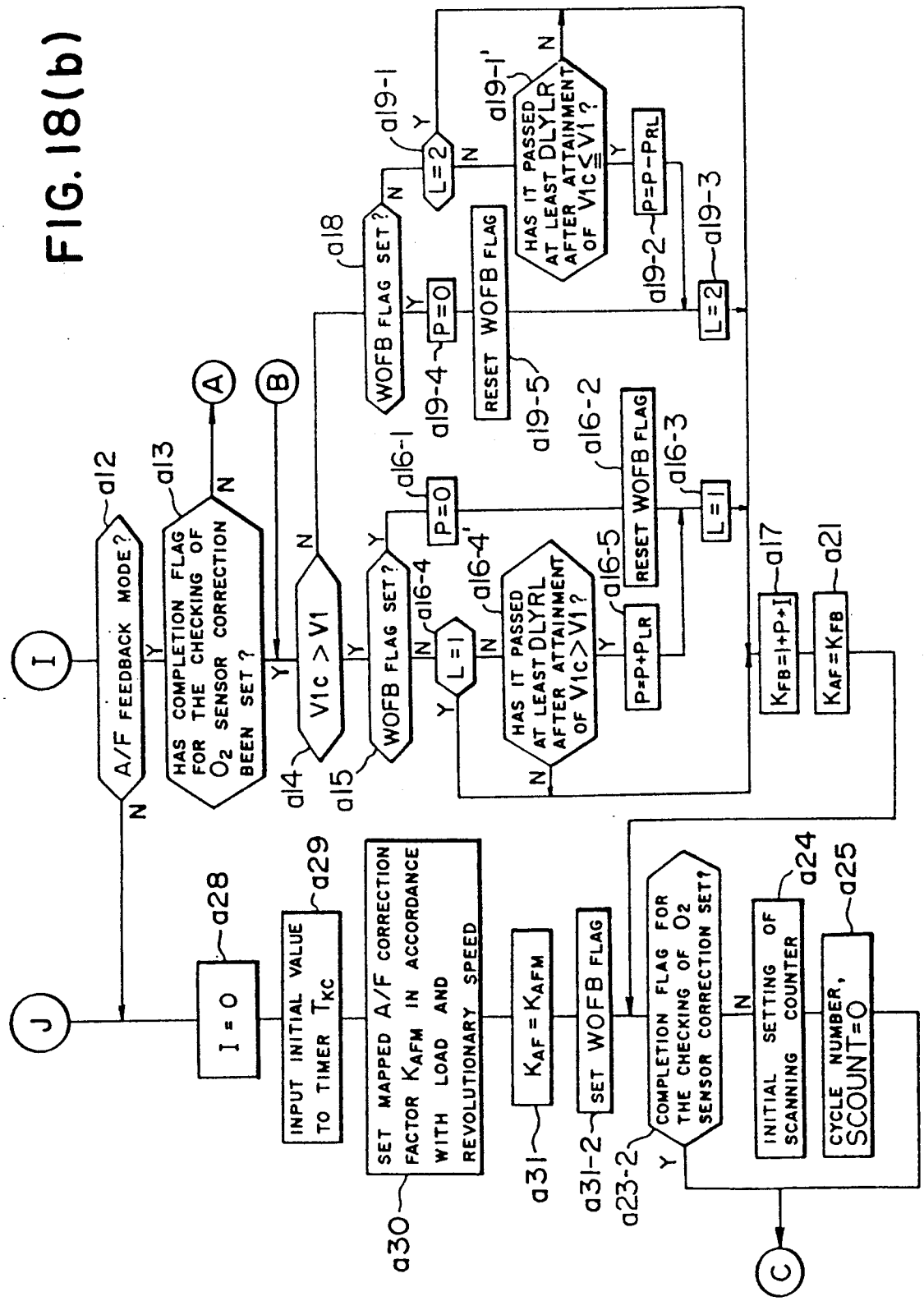
Figure 18C:
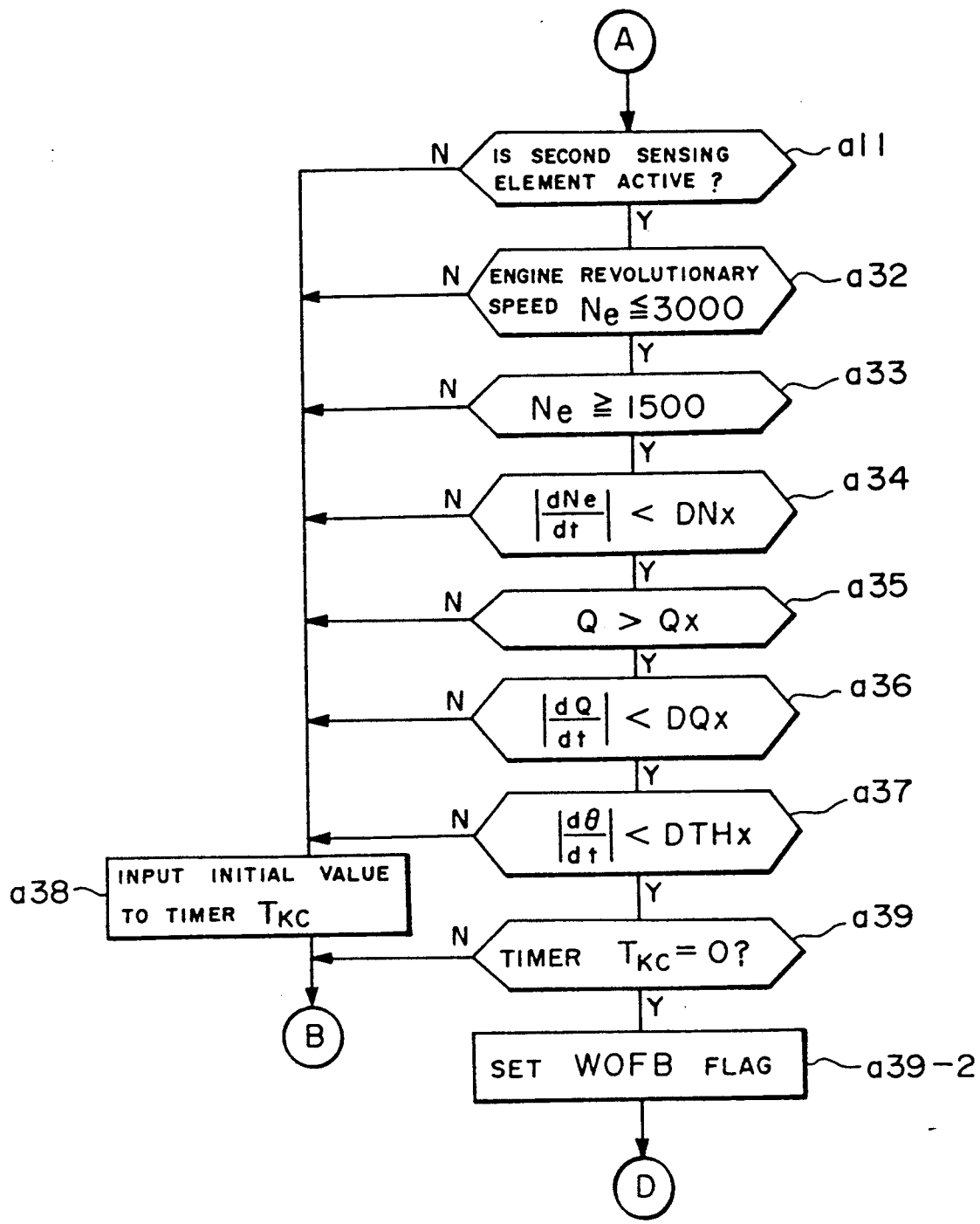

When the timer $T_{KC}$ is not 0, the routine returns to the processings of Step a14 and its subsequent steps depicted in FIG. 18(b).

The routine then advances through Steps a14–a21 in FIG. 18(b). When the routine reaches Step a23-2, the routine advances through the NO route because the completion flag for the checking of correction of the $O_2$ sensor has been reset in Step a71. Initial setting of the scan counter is then performed in Step a24. Here, a suitable number other than 0 is selected as the initial value. The scan counter is used upon changing and renewing the standard value. The n sets of V1 counters, which are employed at this time, are also reset in Step a24.

Further, the cycle number SCOUNT which is also used upon changing and renewing the standard value is set at 0 in Step a25. The routine thereafter returns to Step a5.

When the answers of Steps a32-a37 are both "NO", an initial value (the same value as that inputted in Step a29) is inputted to the timer $T_{KC}$ and the routine returns to the processings of Step a14 and its subsequent steps shown in FIG. 18(b).

Even when the drive distance datum OD has reached the standard value rewriting distance ODX, the routine does not therefore advance to the standard value rewriting processing and is caused to return to the side of the routine work for normal driving so long as both sensing elements 17A,17B are not in an active state, the operation is not in the A/F feedback mode (in which the operation range is set in a relatively stable operation range), the revolutionary speed Ne of the engine does not fall between 1,500 and 3,000 (inclusive, i.e., $1,500 \leq Ne \leq 3,000$), the engine fluctuation is large, the intake air quantity is little, or the intake air fluctuation or throttle opening rate fluctuation is great.

Even when all the above conditions are met, the routine does not advance either to the standard value rewriting processing and is caused to return to the side of the routine work for normal driving until the lapse of prescribed period of time (a time period corresponding to the initial value of the timer $T_{KC}$) after the full satisfaction of the conditions.

Figure 18D:
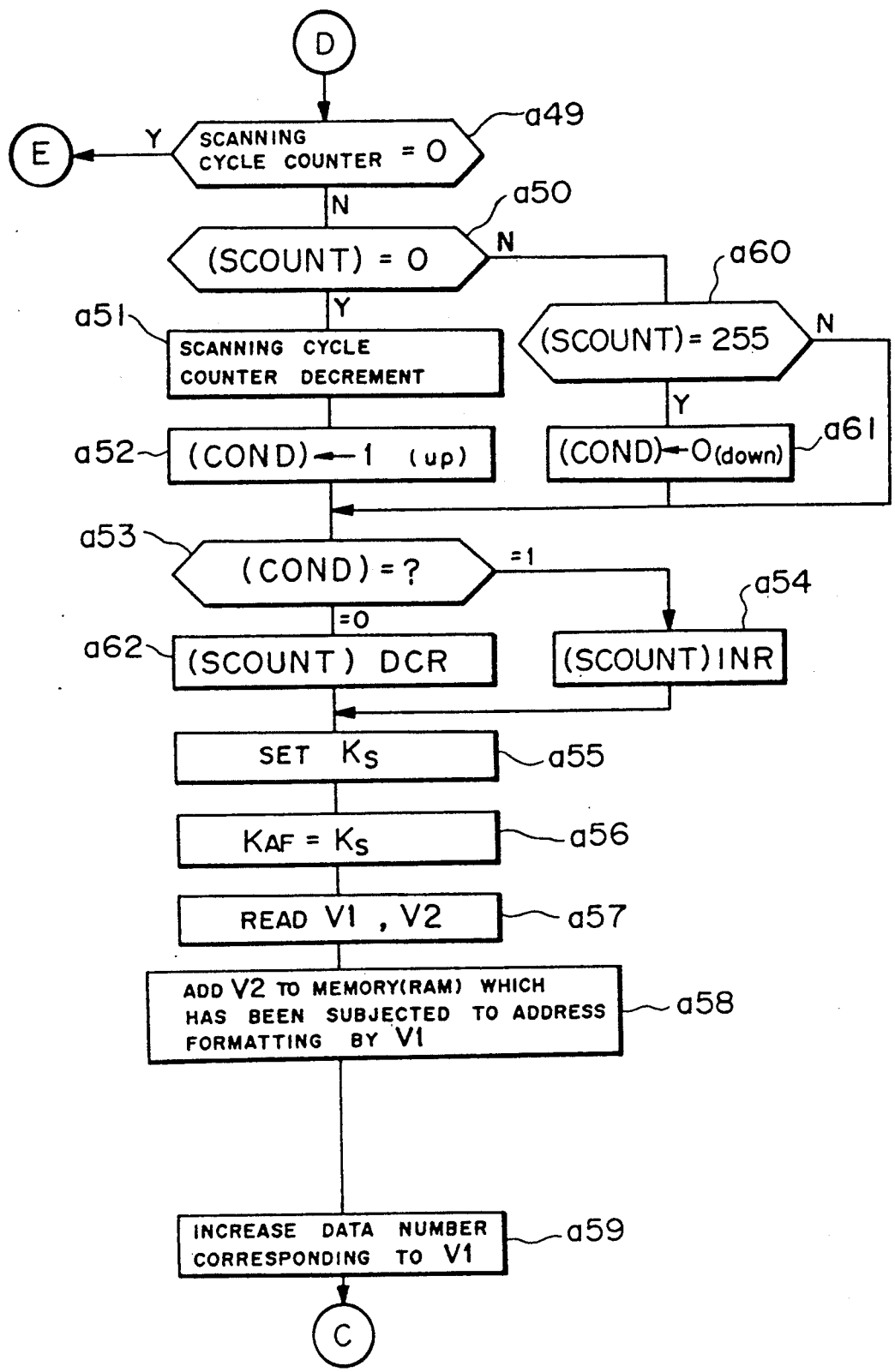
Figure 18E:
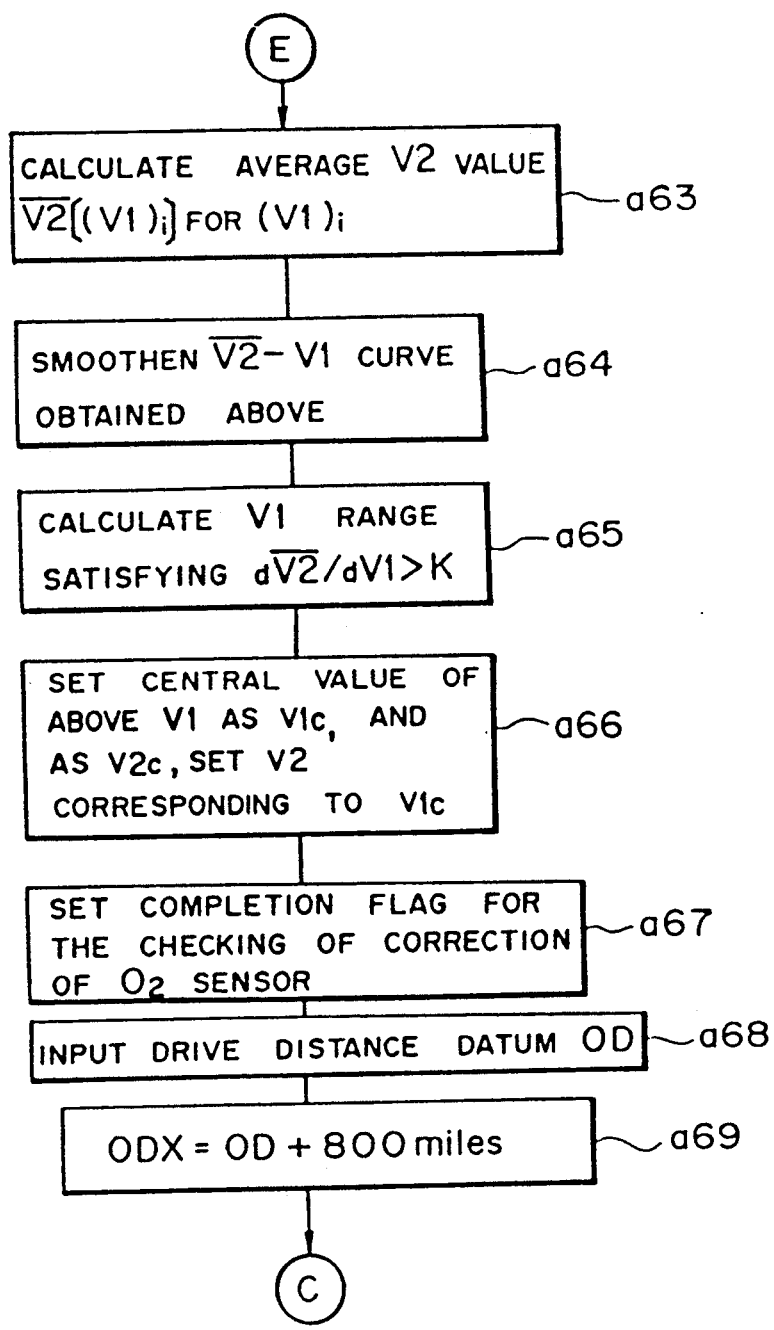

When all the above conditions are met and the prescribed period of time has lapsed (these conditions will hereinafter be called "standard value rewriting conditions"), WOFB flag is set in Step a39-2 and in Step a49 of FIG. 18(d), it is judged whether the scan cycle counter is 0 or not. Since the initial value other than 0 has been set at the beginning in Step a24 of FIG. 18(b), the NO route is taken and in Step a50, it is judged whether the cycle number SCOUNT is 0 or not. In this case, the cycle number has been set at 0 in Step a25 shown in FIG. 18(b). The routine therefore advances along the YES route to Step a51, where decrement (DCR) processing is applied so that the contents of the scan cycle counter are decreased by 1. Flag COND is changed to 1 in the next Step a52 to judge the state of Flag COND in Step a53. Since COND is 1 in this case, the cycle number SCOUNT is increased by 1 step in Step a54.

Thereafter, the air/fuel ratio factor $K_S$ is determined by $1 + (1 - SCOUNT/128) \times 0.05$ (since SCOUNT is 1 in this case, $K_S \approx 1.05$) in Step a55. In Step a56, the factor $K_{AF}$ is determined from $K_S$ to shift the air/fuel ratio to the rich side intentionally. Thereafter, the output V1 of the first sensing element 17A and the output V2 of the second sensing element 17B are read in Step a57. In Step a58, V2 is added to the memory (RAM) which has been address-formatted by V1. In Step a59, the number of data corresponding to the thus-added V1 is increased by 1. In this case, an address number sufficient to prepare the V1-V2 characteristic diagram shown in FIG. 27(b) is chosen as the address number of the memory. The inverse number of this address number is equivalent to the resolution. The V1 counters are provided as many as the address number (n) of the memory, and when V1 is stored at a corresponding address, the count number is increased by 1.

After the above-described Step a59, the routine returns to Step a5 of FIG. 18(a). When the routine advances through the NO route in Step a6, the NO route in Step a13 of FIG. 18(b) and the YES route in Step a39 and returns again to Step a49 shown in FIG. 18(c), the NO route is taken because the scan cycle counter is still not 0. In Step a50, a judgement is made to determine whether SCOUNT is 0 or not. Since SCOUNT has been set at 1 in Step a54 in this case, the NO route is taken in Step a50 and in Step a60, it is judged whether SCOUNT is 255 or not. Since the answer is "NO" in this case, Step a61 is jumped over and a judgement is made in Step a53 to determine the state of Flag COND. Since the state of COND which has been set at 1 in Step a52 has not been cancelled in this case, SCOUNT is again increased by 1 in Step a54. Accordingly, the factor $K_S$ is set by introducing 2/128 as the term SCOUNT/128 in Step a55. After the factor $K_{AF}$ is determined to shift the air/fuel ratio to the lean side a little, the individual outputs V1 and V2 of the first sensing element 17A and second sensing element 17B are read, and V2 is added to the memory which has been address-formatted by V1. After increment of a datum number corresponding to V1 thus added (Steps a56 and a59), the routine returns to Step a5 of FIG. 18(a) and as in the foregoing, again to Step a49 of FIG. 18(d).

Thereafter, the above-described processings are repeated until SCOUNT reaches 255 (SCOUNT=255). The air/fuel ratio is shifted successively from the rich side to the lean side (from about 1.05 to about 0.95 in terms of $K_S$ value) in the above-described manner. By reading the individual outputs V1,V2 of the first sensing element 17A and second sensing element 17B in the course of the shifting of the air/fuel ratio, it is possible to measure the V1-V2 characteristics upon shifting of the air/fuel ratio from the rich side to the lean side around the stoichiometric air/fuel ratio.

When SCOUNT reaches 255, the routine is switched to the YES route in Step a60 and Flag COND hence changes to 0 (Step a61).

Accordingly, the processing of Step a62 is then performed subsequent to Step a53. Namely, the cycle number SCOUNT is decreased by 1 step.

The air/fuel ratio factor $K_S$ is thereafter determined by $1+(1-SCOUNT/128)\times 0.05$ (since SCOUNT is 254 in this case, $K_S \approx 0.95$). After determining the factor $K_{AF}$ as $K_S$ in Step a56, the output V1 of the first sensing element 17A and the output V2 of the second sensing element 17B are read in Step a57. In Step a58, V2 is added to the memory (RAM) which has been address-formatted by V1. The datum number corresponding the thus-added V1 is increased by 1 in Step a59. Since this is the second performance of the routine, the count number of the corresponding counter is increased to 2.

After the Step a59, the routine returns to Step a5 of FIG. 18(a). When the routine advances through the NO route in Step a6, the NO route in Step a13 of FIG. 18(b) and the YES route in Step a39 and returns again to Step a49 shown in FIG. 18(d), the NO route is taken because the scan cycle counter is still not 0. In Step a50, a judgement is made to determine whether SCOUNT is 0 or not. Since SCOUNT has been set at 254 in Step a62 in this case, the NO route is taken in Step a50 and in Step a60, it is judged whether SCOUNT is 255 or not. Since the answer is "NO" in this case, Step a61 is jumped over and a judgement is made in Step a53 to determine the state of Flag COND. Since the state of COND which has been set at 0 in Step a61 has not been cancelled in this case, SCOUNT is again decreased by 1 in Step a62. Accordingly, the factor $K_S$ is set by introducing 253/128 as the term SCOUNT/128 in Step a55. After the factor $K_{AF}$ is determined, the individual outputs V1, V2 of the first sensing element 17A and second sensing element 17B are read, and V2 is added to the memory which has been address-formatted by V1. After increment of a datum number corresponding to V1 thus added (Steps a56 and a59), the routine returns to Step a5 of FIG. 18(a) and as in the foregoing, again to Step a49 of FIG. 18(d).

Thereafter, the above-described processings are repeated until SCOUNT reaches 0 (SCOUNT=0). The air/fuel ratio is thus shifted successively from the lean side to the rich side (from about 0.95 to about 1.05 in terms of $K_S$ value). By reading the individual outputs V1,V2 of the first sensing element 17A and second sensing element 17B in the course of the shifting of the air/fuel ratio, it is possible to perform the second measurement of the V1-V2 characteristics by shifting the air/fuel ratio from the lean side to the rich side around the stoichiometric air/fuel ratio. As a result, the range around the theoretical air/fuel ratio (the V1-V2 characteristics ranging approximately from 1.05 to 0.95 in terms of the value of $K_S$) has been measured back and forth.

When SCOUNT reaches 0, the routine is switched to the YES route in Step a50. After decreasing the scan cycle counter by 1, Flag COND is changed to 1 (Step a52).

Accordingly, the air/fuel ratio is shifted again from the rich side to the lean side and then in the opposite direction, thereby performing the third and fourth measurements of the V1-V2 characteristics.

When the above measurement of the V1-V2 characteristics has been performed back and forth several times (the number of these reciprocations being dependent on the initial value set in the scan cycle counter), the value of the scan cycle counter becomes 0 in Step a51. When the routine has thereafter returned again to Step a49, the YES route is taken to perform the processing of Step a63 shown in FIG. 18(e). Namely, in Step a63, an average value $\overline{V2[(V1)_i]}$ of V2 for $(V1)_i$ measured by that time is calculated. Upon calculation of the average value, the count number of the V1 counter is used.

After determination of the average value V2 in the above manner, the $\overline{V2}$-V1 curve is smoothened by a suitable interpolation method or the like in Step a64. The characteristics thus obtained [see FIG. 27(c)] are the V1-V2 characteristics shown in FIG. 27(b).

The routine then advances to Step a65. A V1 range satisfying $d\overline{V2}/dV1 > K$, namely, a V1 range where V2 rises abruptly is determined. In Step a66, the median of the V1 range is chosen as the rich/lean-judging standard value $V1_c$. A V2 corresponding to the standard value $V1_c$ is set as a new value $V2_c$. These new values $V1_c, V2_c$ are stored in the BURAM 33. Thus, the rewriting of the standard values $V1_c$, $V2_c$, namely, the renewal of the standard value $V1_c$, $V2_c$ have been completed. The completion flag for the checking of correction of the $O_2$ sensor is then set in Step a67. The drive distance datum OD is inputted in Step a68, and the next standard value rewriting distance ODX is set, for example, at ODX+800 (miles) in Step a69.

In the above-described manner, the standard value $V2_c$ of the output of the second sensing element 17B (said $V2_c$ being available form $V1_c$ as mentioned above) is also renewed for the prescribed drive distance or at every history of battery disconnection in the first embodiment, in addition to the rich/lean judging standard value $V1_c$ which is to be compared with the output V1 of the first sensing element 17A. Namely, these values $V1_c, V2_c$ are not set as fixed values but are set as variable values.

Figure 27D:
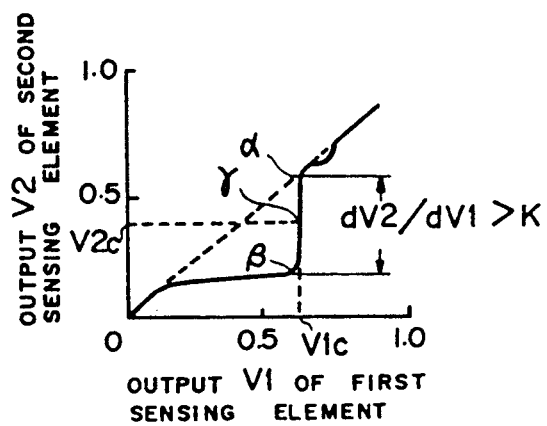

Here, the standard value $V2_c$ is determined in the following manner. As illustrated in FIG. 27(d), the output value of the second sensing element 17B corresponding substantially to the central point of a range in which dV2/dV1 is greater than a certain inclination [see FIG. 14(e), Step a65] is determined as the standard value $V2_c$. When $V1_c$ is about 0.6 volt by way of example, $V2_c$ is about 0.4 volt.

If $V2_c$ is set at a point $\alpha$ in FIG. 27(d), the cleaning efficiency of CO is deteriorated. If $V2_c$ is set at a point $\beta$ on the contrary, the cleaning efficiency of $NO_x$ is impaired. $V2_c$ is therefore set at the central point λ as described above.

After the next standard value rewriting distance ODX has been set, for example, at ODX+800 (miles) in the above-described manner, the routine returns to Step a5 of FIG. 18(a). If the operation is not in the fuel cut-off zone, the NO route is taken in Step a6 and Steps a7–a9 are then performed. If the answers of Steps a10-,a12 are all "YES", it is judged in Step a13 whether the completion flag for the checking of correction of the $O_2$ sensor has been set or not. Since this flag is in a set state in Step a67 of FIG. 18(d), the above-described routine work for normal driving, said routine work being defined by Step a14 and its subsequent steps, is performed.

Incidentally, when the battery has been found to have the history of disconnection in Step a2, initial values are inputted as the standard values $V1_c, V2_c$ {those to be corrected based on an output from the second sensing element 17B out of the values of $(DLYRL, DLYLR)$, $(I_{RL}, I_{LR})$ and $(P_{RL}, P_{LR})$} respectively in Step a70. Here, the standard value $V1_c$ may be set at about 0.6 volt by way of example while $V2_c$ may be set at about 0.4 volt by way of example.

A description will next be made of a method for correcting the response delay times DLYRL,DLYLR, proportional gains $P_{RL}, P_{LR}$, integral gains $I_{RL}, I_{LR}$ and rich/lean judgement voltage $V2_c$ on the basis of the output V2 of the second sensing element and the standard value $V2_c$.

Figure 21:
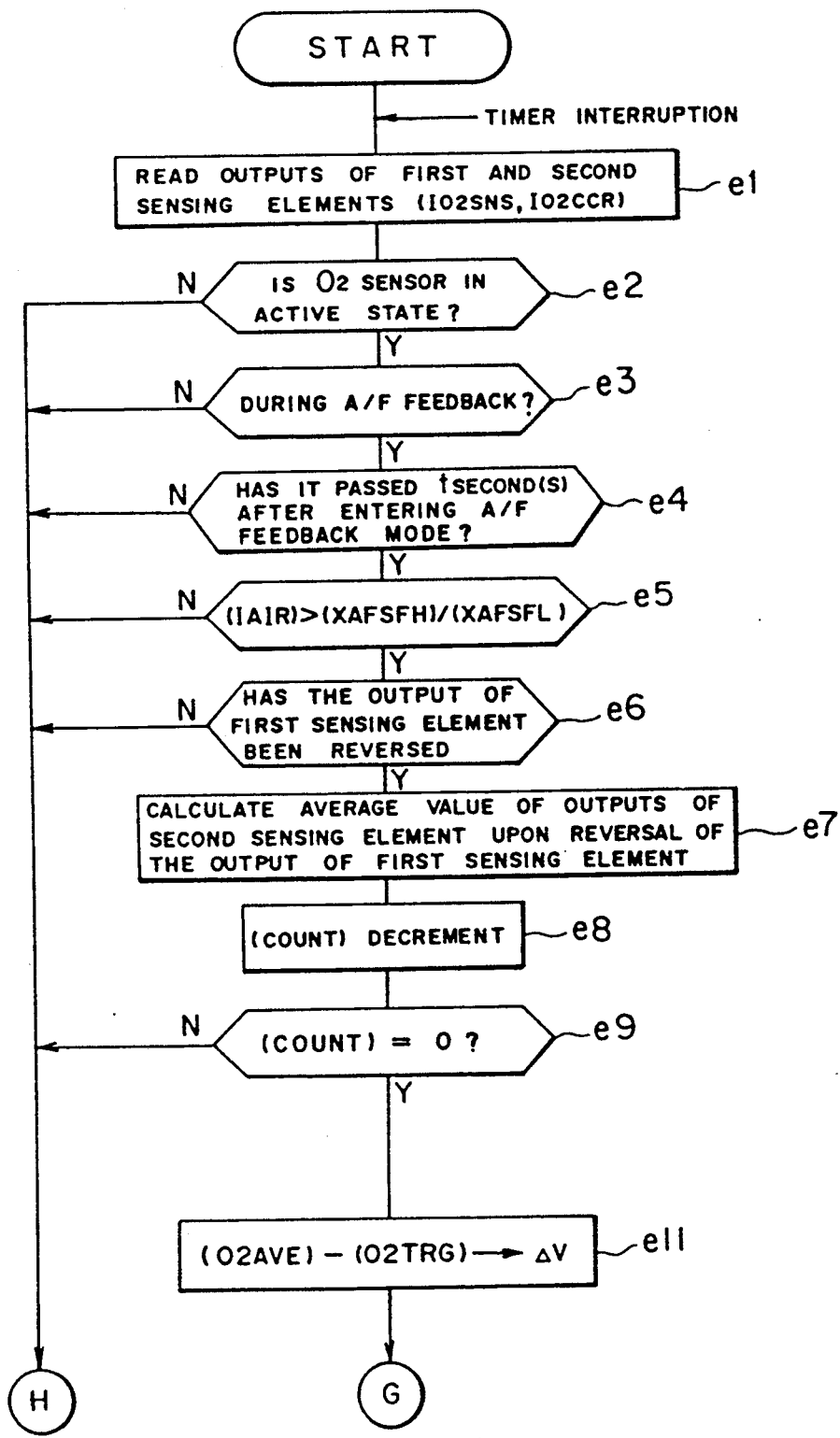

As shown in FIG. 21, the outputs IO2SNS (V1) and IO2CCR (V2) of the first and second sensing elements 17A,17B are read in first of all in Step e1. As the timing of their reading, they may be read in, for example, every 5 msec or every 10 msec. In Step e2, it is then judged from the output voltage values of the first and second sensing elements 17A,17B whether they are in an active state or not.

For the above judgement, it should be noted that separate standard voltage values can be set for the first and second sensing elements 17A,17B.

If both sensing elements 17A,17B are in the active state, it is judged in Step e3 whether the operation is in the air/fuel ratio feedback or not. If the answer is "YES", the routine advances to Step e4 where a judgement is made to determine whether a predetermined period of time has lapsed after the entering in the air/fuel ratio feedback mode. If the answer is "YES", it is judged in Step e5 whether the output frequency IAIR of the airflow sensor 11, namely, the intake air quantity is greater than a preset value.

As the preset value, two values are set, one being a first preset value (XAFSFH) and the other a second preset value (XAFSFL). A judgement is made by using these different preset values, one when the output of the airflow sensor increases and the other when it decreases. Namely, hysteresis has been set for the judgement in Step a5, thereby bringing about an advantage for the preventing of hunting.

In an operational state featuring a small intake air quantity (during idling or the like), the response of the $O_2$ sensors is slow and the output characteristics of the $O_2$ sensors are different. A judgement such as that performed in Step e5 is therefore carried out. It is also feasible to perform the following correction separately when the output frequency of the airflow sensor is lower than a preset value. In this case, learning is performed twice.

If the answer is "YES" in Step e5, it is judged in the next Step e6 whether the output of the first sensing element has been reversed or not. Incidentally, $V1_c$ determined and renewed in the above-described main routine [FIGS. 18(a) through 18(e)] is used as the rich/lean-judging standard value $V1_c$ for each output of the first sensing element 17A.

When the answer is "NO" in any one of Steps e2–e6, the routine returns.

When the answer is "YES" in Step e6, the average output value of the second sensing element 17B is renewed in Step e7 on the basis of the short-term output value IO2CCR of the second sensing element 17B at the time of reversal of the output of the first sensing element and the average output value of the second sensing element 17B already in storage. Namely, a new average output value O2AVE of the second sensing element 17B, which is expressed by the left-hand member of the following equation, is determined as follows.

$$O2AVE = K1(IO2CCR) + (1 - K1)(O2AVE)$$

Incidentally, O2AVE in the right-hand member of the above formula indicates the last datum of the average output value of the second sensing element 17B, which had replaced the previous one in Step e7 of the last performance of the time interruption routine and has been stored in the RAM.

Here, K1 is a factor set as a datum in the ROM.

In addition, the contents of the counter COUNT are reduced by 1 in Step e8. Here, the initial value of the counter is set by the data of the ROM and a desired value from 1 to 255 may be set by way of example. This initial value was set in the counter in Step a1 of the main routine shown in FIG. 18(a), when the key switch was turned on.

In the next Step e9, it is judged whether the number of the counter has been counted down to 0. If the answer is "NO", the routine returns. When the answer becomes "YES" (namely, the smoothening processing of output data of the second sensing element 17B has been performed fully), the routine advances to Step e11 where from a target output voltage value O2TRG (which corresponds to $V2_c$) of the second sensing element 17B and the average output value O2AVE of the second sensing element 17B at the time of rich/lean reversal of the first sensing element 17A, the deviation ΔV between these values is determined. By the way, the initial value upon turning on the key switch is set equal to the same value as the target output value, namely, O2TRG.

When the deviation ΔV has been determined as described above, the characteristic values for the air/fuel ratio feedback control, namely, the response delay times, integral gains, proportional gains and the standard value for the first sensing element are corrected by using ΔV.

Since variations of the output V2 of the second sensing element 17B are slow during the air/fuel ratio feedback control, it is not preferable to use the output V2 directly for the air/fuel ratio feedback control. The output V2 is however produced with substantially the same delay when the fuel/gas ratio changes from the lean side to the rich side and from the rich side to the lean side. It is hence useful for such corrections of characteristic values for the air/fuel ratio feedback control as described above.

Figure 22:
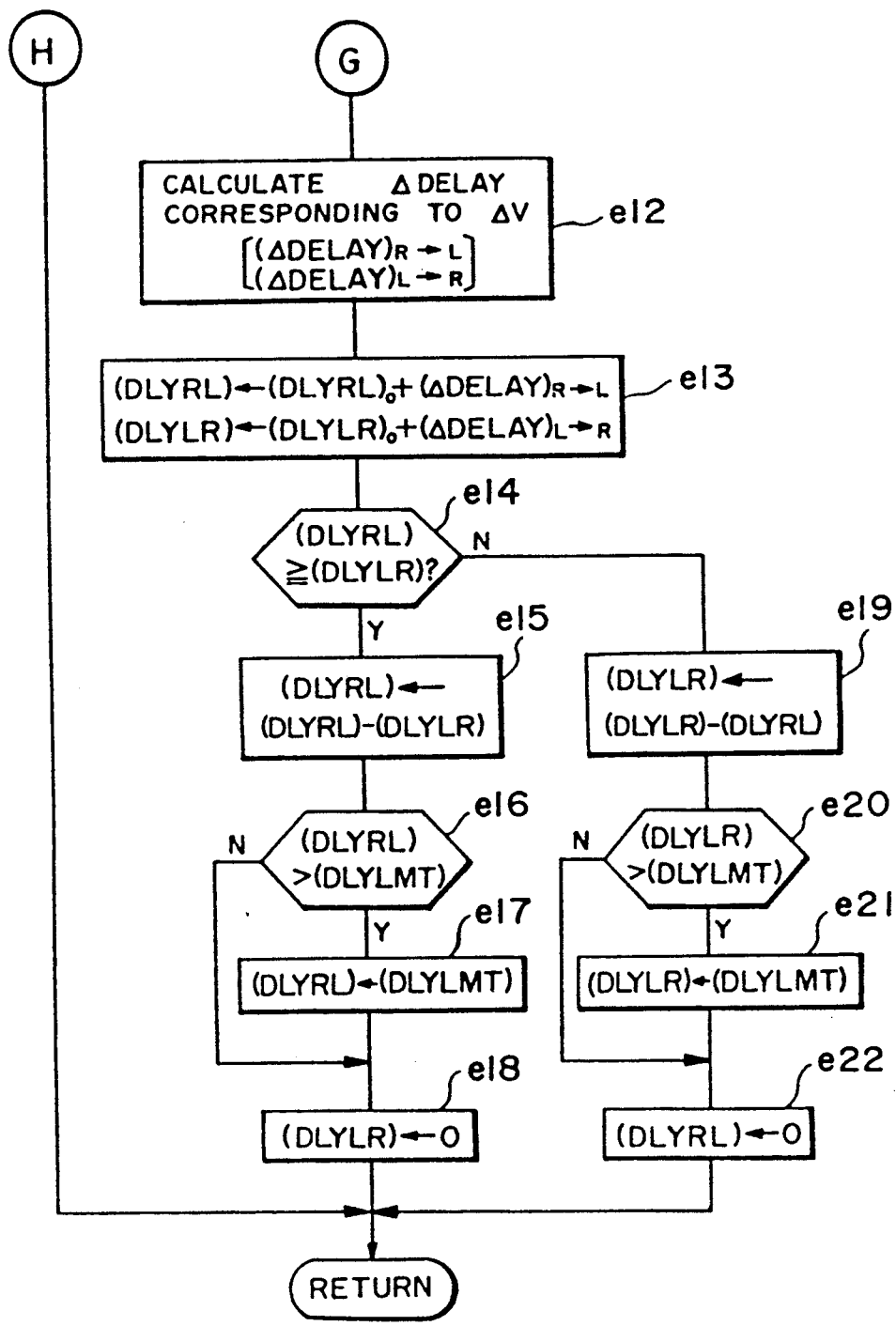

The corrections of the response delay times DLYRL,DLYLR are described first of all. As shown in FIG. 22, $\Delta$DELAY corresponding to $\Delta$V obtained in Step e11 of FIG. 21 is determined first of all in Step e12.

Figure 28A:
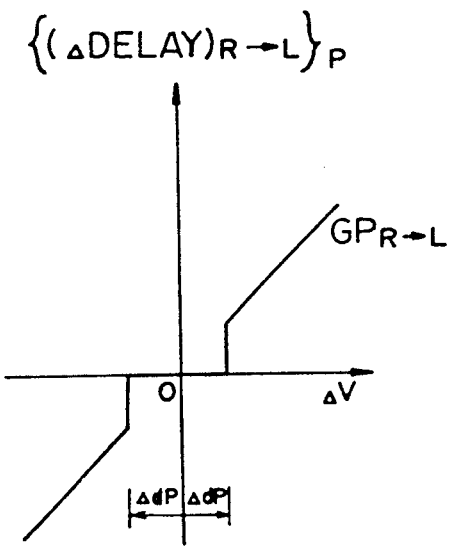
FIGS. 28(a) and 28(b) and FIGS. 29(a) and 29(b) are respectively graphs for describing a correction value for response delay time.
Figure 28B:
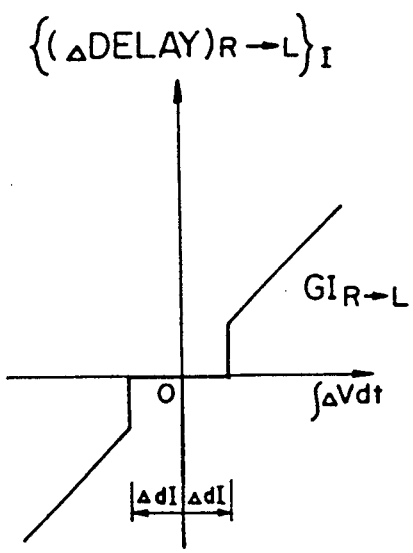
Figure 29A:
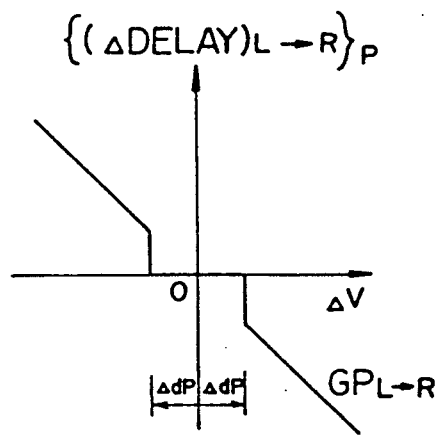
Figure 29B:
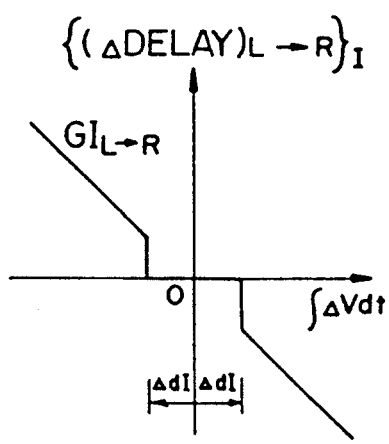

By the way, there are two kinds of delays as $\Delta$DELAY, one being a delay that takes place when the air/fuel ratio changes from the rich side to the lean side and the other being a delay that occurs when the air/fuel ratio changes from the lean side to the rich side. Correction characteristics for the former delay may be illustrated as shown in FIGS. 28(a) and 28(b), while those for the latter delay may be depicted as shown in FIGS. 29(a) and 29(b). Namely, $\Delta$DELAY is given as the sum of $\{\Delta DELAY\}_P$ based on a short-term value of $\Delta$V and $\{\Delta DELAY\}_I$ based on an integrated value of $\Delta$V. It may hence be expressed as follows.

$$(\Delta DELAY)_{R \to L} = \{(\Delta DELAY)_{R \to L}\}_I + \{(\Delta DELAY)_{R \to L}\}_P$$

$$(\Delta DELAY)_{L \to R} = \{(\Delta DELAY)_{L \to R}\}_I + \{(\Delta DELAY)_{L \to R}\}_P$$

Inclinations GP,GI shown in these FIGS. 28(a) and 28(b) and FIGS. 29(a) and 29(b) as well as dead zones $\Delta$dP,$\Delta$dI are set in the ROM data.

After determination of $\Delta$DELAYs in the above manner, these $\Delta$DELAYs are added respectively to standard values $(DLYRL)_o$ and $(DLYLR)_o$ of DLYRL and DLYLR in Step e13, thereby determining new DLYRL and DLYLR.

In the next Step e14, it is judged whether DLYRL is either equal to or greater than DLYLR (DLYRL$\geq$DLYLR). If the answer is "YES", results obtained by subtracting DLYLR from DLYRL are set as new DLYRL in Step e15. In the next Step e16, it is judged whether DLYRL is greater than DLYLMT (delay limiting value: set by the ROM data) or not. While DLYRL has not reached this limiting value, Step e17 is jumped over, DLYLR is changed to 0 in Step e18, and the routine returns. When DLYRL reaches the limiting value, the limiting value is set as DLYRL in Step e17 and the processing of Step e18 is then applied.

If DLYRL < DLYLR in Step e14, results obtained by subtracting DLYRL from DLYLR are set as new DLYLR in Step e19. In the next Step e20, it is judged whether DLYLR is greater than DLYLMT (delay limiting value: set by the ROM data) or not. While DLYLR has not reached this limiting value, Step e21 is jumped over, DLYRL is changed to 0 in Step e22, and the routine returns. When DLYLR reaches the limiting value, the limiting value is set as DLYLR in Step e21 and the processing of Step e22 is then applied.

The delay limiting values compared in Steps e16,e20 respectively may be the same or different.

Although DLYRL and DLYLR are both backed up by a battery, their initial values in Step a70" are set at 0 by way of example.

When DLYRL and DLYLR are corrected on the basis of the output of the second sensing element 17B and the air/fuel ratio is rendered richer, DLYLR is added as shown in FIGS. 35(a) through 35(c): For rendering the air/fuel ratio leaner, DLYRL is added as illustrated in FIGS. 36(a) through 36(c).

As has been described above, the output V2 of the second sensing element 17B is measured during the air/fuel ratio feedback control at constant time intervals (or whenever the output V1 of the first sensing element 17A crosses the standard value $V1_c$) and the correction of the response delay time is effected to make its moving average equal to $V2_c$.

Figure 23:
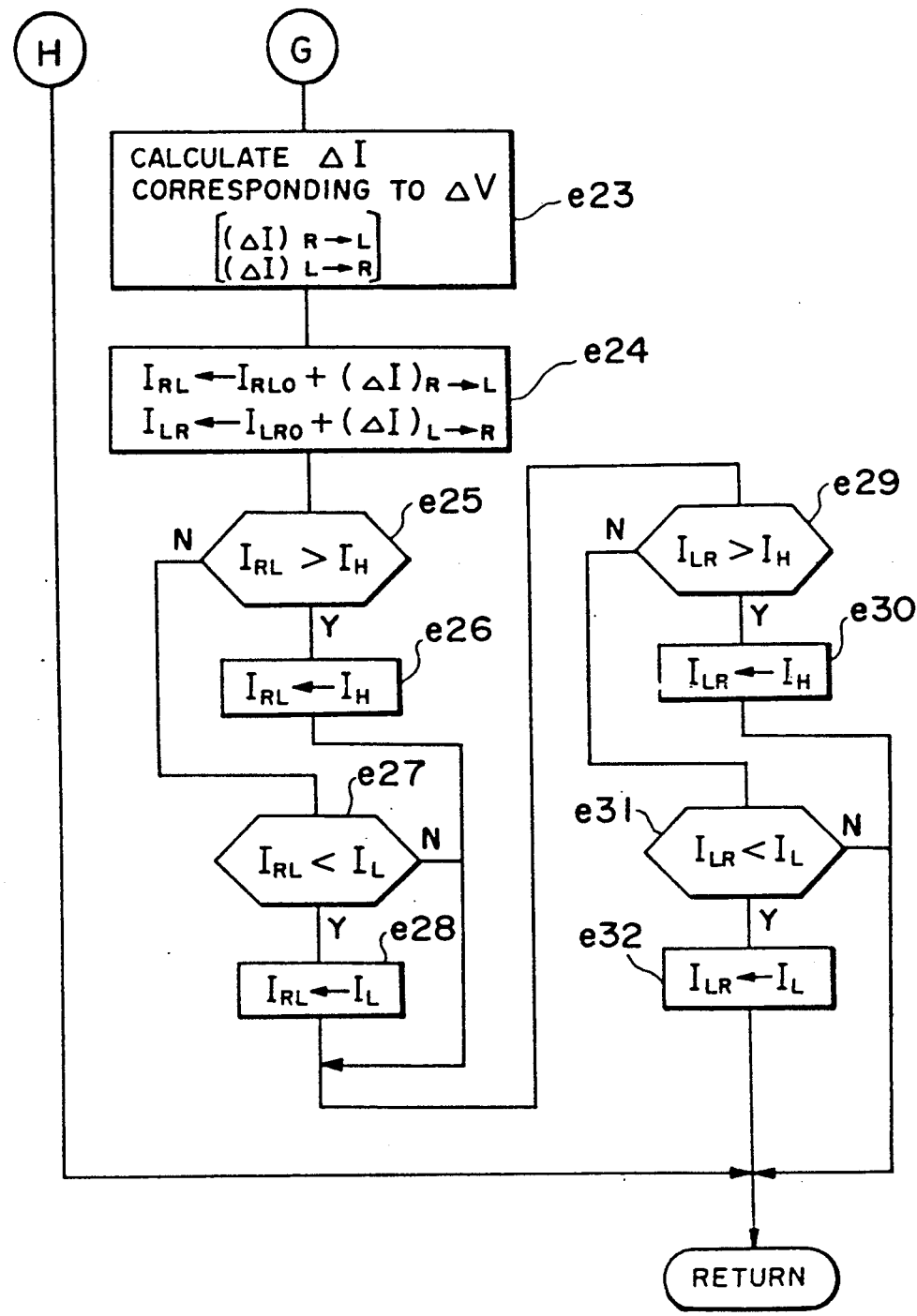

A description will next be made of the corrections of the integral gains $I_{RL}, I_{LR}$ for the air/fuel ratio feedback control. As illustrated in FIG. 23, $\Delta I$ corresponding to $\Delta V$ obtained in Step e11 of FIG. 21 is determined first of all in Step e23.

Figure 30A:
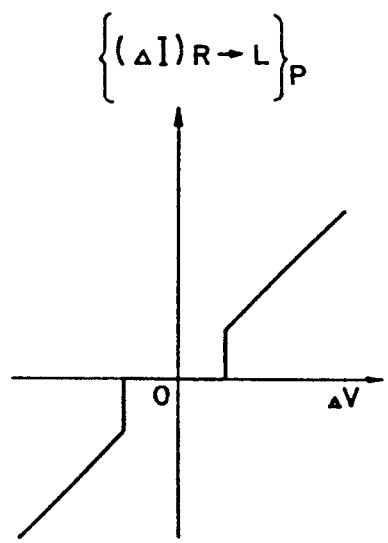
FIGS. 30(a) and 30(b) and FIGS. 31(a) and 31(b) are respectively graphs for illustrating a correction value for the integral gain which is for the air/fuel ratio feedback control.
Figure 30B:
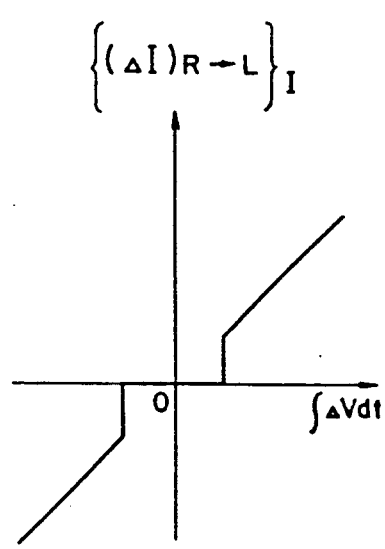
Figure 31A:
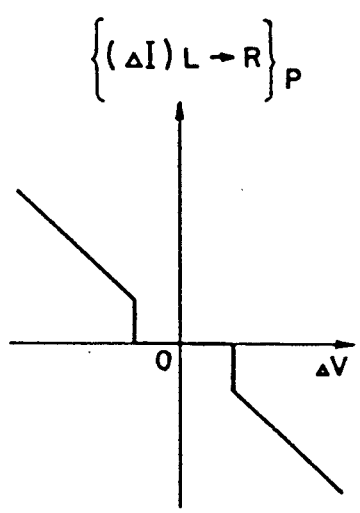
Figure 31B:
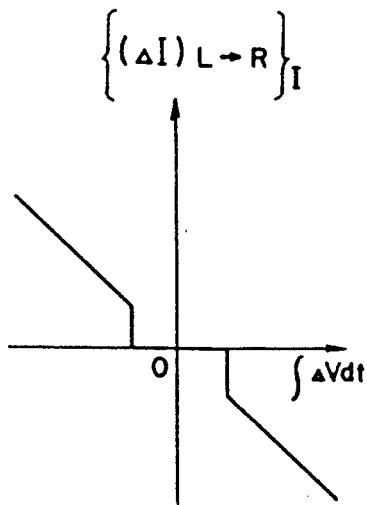

By the way, there are two kinds of integral gains as $\Delta I$, one being an integral gain for the change of the air/fuel ratio from the rich side to the lean side and the other being an integral gain for the change of the air/fuel ratio from the lean side to the rich side. Correction characteristics for the former integral gain may be illustrated as shown in FIGS. 30(a) and 30(b), while those for the latter integral gain may be depicted as shown in FIGS. 31(a) and 31(b). Namely, $\Delta I$ is given as the sum of $\{\Delta I\}_P$ based on a short-term value of $\Delta V$ and $\{\Delta I\}_I$ based on an integrated value of $\Delta V$. It may hence be expressed as follows.

$$(\Delta I)_{R \to L} = \{(\Delta I)_{R \to L}\}_I + \{(\Delta I)_{R \to L}\}_P$$

$$(\Delta I)_{L \to R} = \{(\Delta I)_{L \to R}\}_I + \{(\Delta I)_{L \to R}\}_P$$

Functional relations (inclinations and dead zones) shown in these FIGS. 30(a) and 30(b) and FIGS. 31(a) and 31(b) are set in the ROM data.

After determination of $\Delta I$s in the above manner, these $\Delta I$s are added respectively to standard values $I_{RLo}$ and $I_{LRo}$ of $I_{RL}$ and $I_{LR}$ in Step e24, thereby determining new $I_{RL}$ and $I_{LR}$.

In the next Step e25, it is judged whether $I_{RL}$ is greater than $I_H$ (upper limit: this value is set in the ROM data). If the answer is "NO", it is judged in Step e27 whether $I_{RL}$ is smaller than $I_L$ (lower limit: this value is set in the ROM data; $I_{RL} < I_L$).

If the answer is "YES" in Step e25, $I_H$ is set as $I_{RL}$ in Step e26. If the answer is "YES" in Step e27, $I_L$ is set as $I_{RL}$ in Step e28.

If the answer is "NO" in Step e27, after the processings of Steps e26,e28, it is judged in the next Step e29 whether $I_{LR}$ is greater than $I_H$ (upper limit: this value is set in the ROM data). If the answer is "NO", it is judged in Step e31 whether $I_{LR}$ is smaller than $I_L$ (lower limit: this value is set in the ROM data; $I_{LR} < I_L$).

If the answer is "YES" in Step e29, $I_H$ is set as $I_{LR}$ in Step e30. Further, if the answer is "YES" in Step e31, $I_L$ is set as $I_{LR}$ in Step e32 and the routine then returns.

Incidentally, the individual upper limits compared in Steps e25,e29 may be the same or different. Further, the lower limits compared in Steps e27,e31 may also be the same or different.

Further, the integral gains $I_{RL}$ and $I_{LR}$ are both backed up by the battery.

Figure 37A:
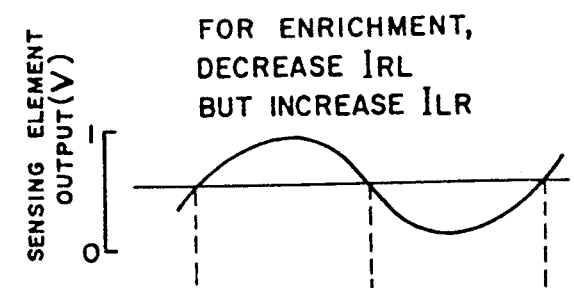
Figure 37C:
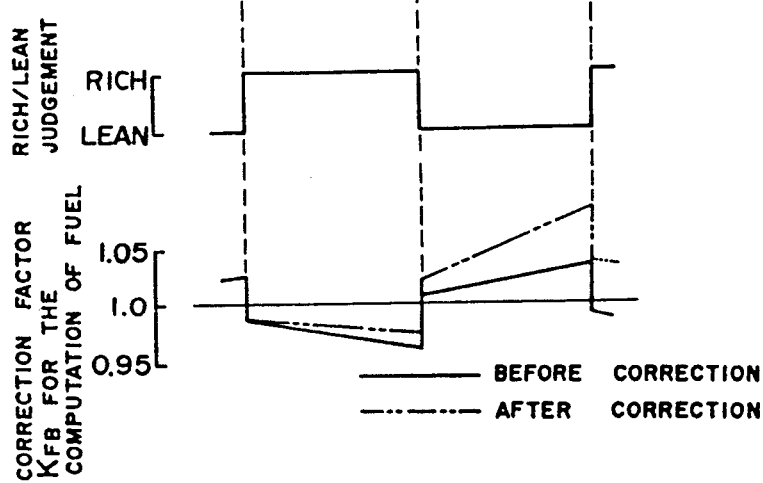
Figure 38A:
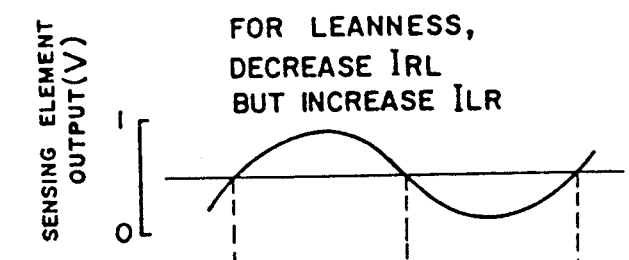
Figure 38C:
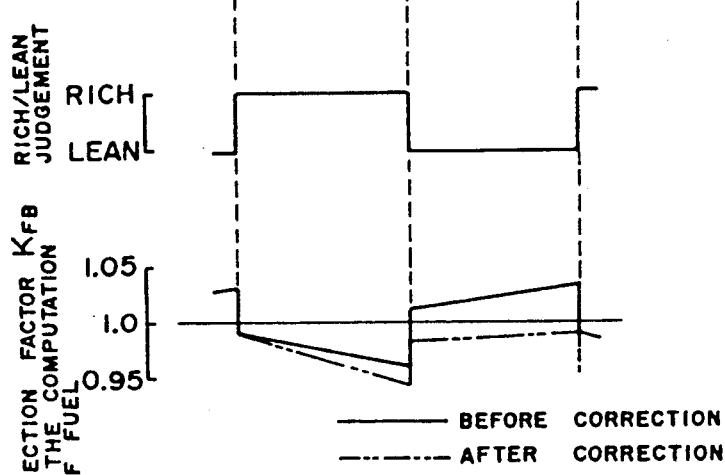

When $I_{RL}$ and $I_{LR}$ are corrected on the basis of the output V2 of the second sensing element 17B and the air/fuel ratio is rendered richer, $I_{RL}$ is rendered smaller and at the same time, $I_{LR}$ is rendered greater as illustrated in FIGS. 37(a) through 37(c). For rendering the air/fuel ratio leaner, $I_{RL}$ is rendered greater and at the same time, $I_{LR}$ is rendered smaller as illustrated in FIGS. 38(a) through 38(c).

As has been described above, the output V2 of the second sensing element 17B is measured during the air/fuel ratio feedback control at constant time intervals (or whenever the output V1 of the first sensing element 17A crosses the standard value $V1_c$) and the correction of the integral gain is effected to make its moving average equal to $V2_c$.

Figure 24:
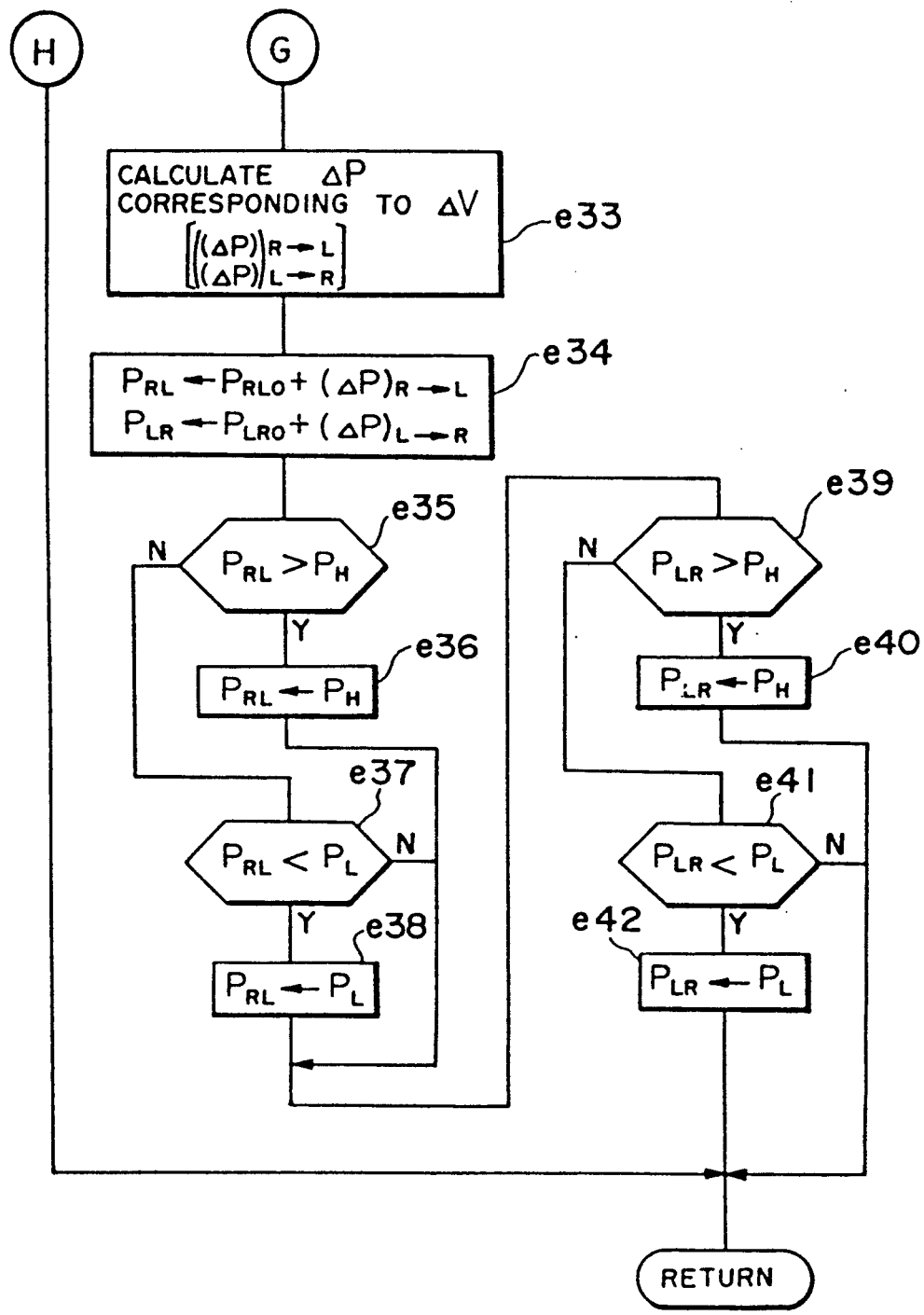

The corrections of the proportional gains $P_{RL}, P_{LR}$ for the air/fuel ratio feed back control will next be described. As illustrated in FIG. 24, $\Delta P$ corresponding to $\Delta V$ obtained in Step e11 of FIG. 21 is determined in Step e33.

Figure 32A:
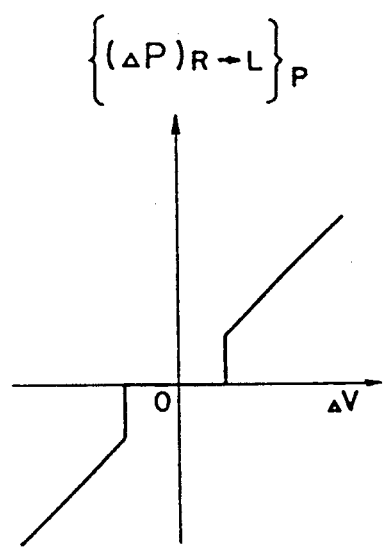
FIGS. 32(a) and 32(b) and FIGS. 33(a) and 33(b) are respectively graphs for illustrating a correction value for the proportional gain which is for the air/fuel ratio feedback control.
Figure 32B:
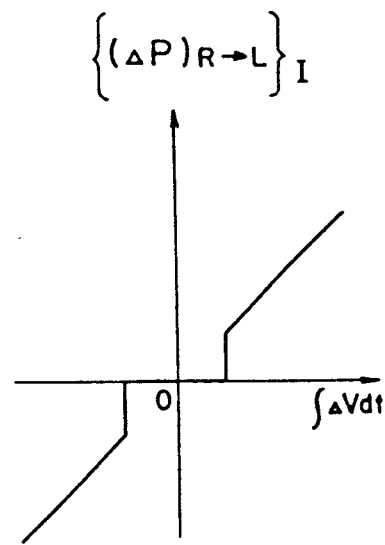
Figure 33A:
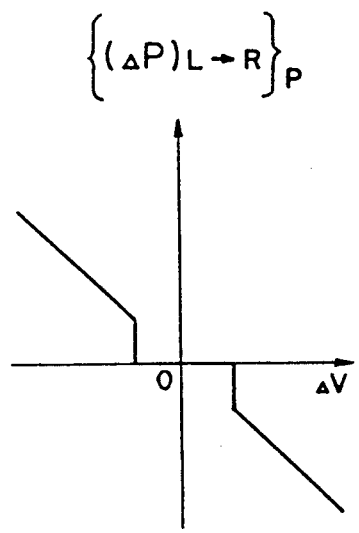
Figure 33B:
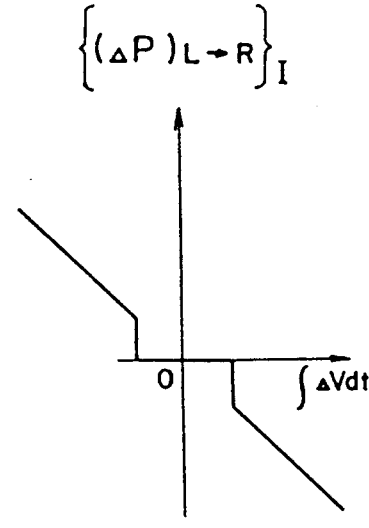

By the way, there are two kinds of proportional gains as $\Delta P$, one being a proportional gain for the change of the air/fuel ratio from the rich side to the lean side and the other being a proportional gain for the change of the air/fuel ratio from the lean side to the rich side. Correction characteristics for the former proportional gain may be illustrated as shown in FIGS. 32(a) and 32(b), while those for the latter proportional gain may be depicted as shown in FIGS. 33(a) and 33(b). Namely, $\Delta P$ is given as the sum of $\{\Delta P\}_P$ based on a short-term value of $\Delta V$ and $\{\Delta P\}_I$ based on an integrated value of $\Delta V$. It may hence be expressed as follows.

$$(\Delta P)_{R \rightarrow L} = \{(\Delta P)_{R \rightarrow L}\}_I + \{(\Delta P)_{R \rightarrow L}\}_P$$

$$(\Delta P)_{L \rightarrow R} = \{(\Delta P)_{L \rightarrow R}\}_I + \{(\Delta P)_{L \rightarrow R}\}_P$$

Functional relations (inclinations and dead zones) shown in these FIGS. 32(a) and 32(b) and FIGS. 33(a) and 33(b) are set in the ROM data.

After determination of $\Delta P$s in the above manner, these $\Delta P$s are added respectively to standard values $P_{RLo}$ and $P_{LRo}$ of $P_{RL}$ and $P_{LR}$ in Step e34, thereby determining new $P_{RL}$ and $P_{LR}$.

In the next Step e35, it is judged whether $P_{RL}$ is greater than $P_H$ (upper limit: this value is set in the ROM data). If the answer is "NO", it is judged in Step e37 whether $P_{RL}$ is smaller than $P_L$ (lower limit: this value is set in the ROM data; $P_{RL} < P_L$).

If the answer is "YES" in Step e35, $P_H$ is set as $P_{RL}$ in Step e36. If the answer is "YES" in Step e37, $P_L$ is set as $P_{RL}$ in Step e38.

If the answer is "NO" in Step e37, after the processings of Steps e36, e38, it is judged in the next Step e39 whether $P_{LR}$ is greater than $P_H$ (upper limit: this value is set in the ROM data $P_{LR} > P_H$). If the answer is "NO", it is judged in Step e41 whether $P_{LR}$ is smaller than $P_L$ (lower limit: this value is set in the ROM data; $P_{LR;} < P_L$).

If the answer is "YES" in Step e39, $P_H$ is set as $P_{LR}$ in Step e40. Further, if the answer is "YES" in Step e41, $P_L$ is set as $P_{LR}$ in Step e42 and the routine then returns.

Incidentally, the individual upper limits compared in Steps e35, e39 may be the same or different. Further, the lower limits compared in Steps e37, e41 may also be the same or different.

Further, the proportional gains $P_{RL}$ and $P_{LR}$ are both backed up by the battery.

When $P_{RL}$ and $P_{LR}$ are corrected on the basis of the output V2 of the second sensing element and the air/fuel ratio is rendered richer, $P_{RL}$ is rendered smaller and at the same time, $P_{LR}$ is rendered greater as illustrated in FIGS. 39(a) through 39(c). For rendering the air/fuel ratio leaner, $P_{RL}$ is rendered greater and at the same time, $P_{LR}$ is rendered smaller as illustrated in FIGS. 40(a) through 40(c).

As has been described above, the output V2 of the second sensing element 17B is measured during the air/fuel ratio feedback control at constant time intervals (or whenever the output V1 of the first sensing element 17A crosses the standard value $V1_c$) and the correction of the proportional gain is effected to make its moving average equal to $V2_c$.

Figure 25:
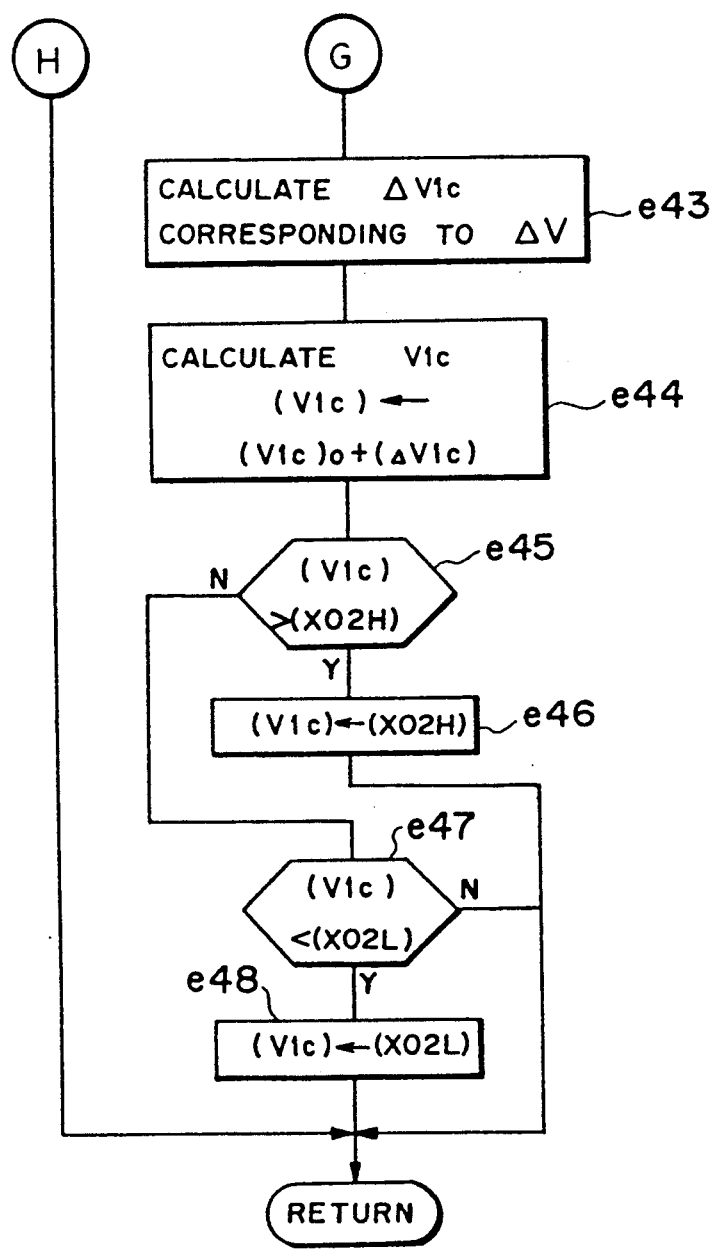

A description will next be made of the correction of the rich/lean-judging standard value $V1_c$. First of all, as illustrated in FIG. 25, $\Delta V1_c$ corresponding to $\Delta V$ obtained in Step e11 of FIG. 21 is calculated in Step e43.

Figure 34A:
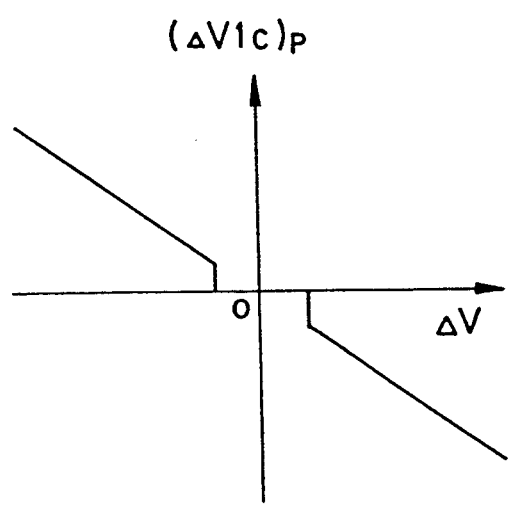
FIGS. 34(a) and 34(b) are respectively graphs for describing a correction value for the standard value for rich/lean judgement to be compared with an output from a forward O₂ sensor.
Figure 34B:
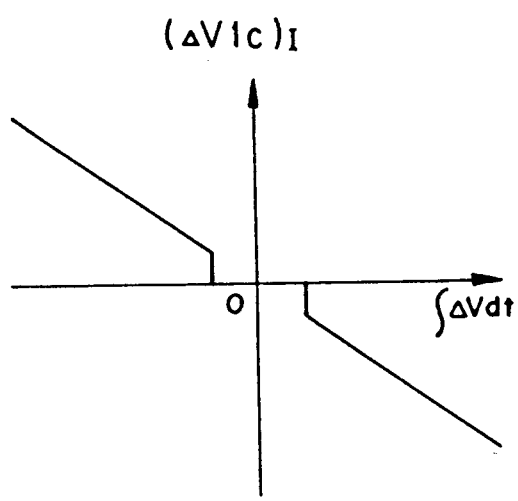

Correction characteristics for the $\Delta V1$ may be illustrated as shown in FIGS. 34(a) and 34(b).

Namely, $\Delta V1_c$ is given as the sum of $\{\Delta V1_c\}_P$ based on a short-term value of $\Delta V$ and $\{\Delta V1_c\}_I$ based on an integrated value of $\Delta V$. It may hence be expressed as follows.

$$\Delta V1_c = (\Delta V1_c)_I + (\Delta V1_c)_P$$

Functional relations (inclinations and dead zones) shown in these FIGS. 34(a) and 34(b) are also set in the ROM data.

After determination of the $\Delta V1_c$ in the above manner, the $\Delta V1_c$ is added to the standard value $(V1_c)_o$ of $V1_c$ in Step e44, thereby determining new $V1_c$.

In the next Step e45, it is judged whether $V1_c$ is greater than XO2H (upper limit: this value is set in the ROM data; $V1_c > XO2H$). If the answer is "NO", it is judged in Step e47 whether $V1_c$ is smaller than XO2L (lower limit: this value is set in the ROM data; $V1_c < XO2L$).

If the answer is "YES" in Step e45, XO2H is set as $V1_c$ in Step e46. If the answer is "YES" in Step e47, XO2L is set as $V1_c$ in Step e48.

If the answer is "NO" in Step e47, after the processings of Steps e46, e48, the routine returns.

When $V1_c$ is corrected on the basis of the output V2 of the second sensing element and the air/fuel ratio is rendered richer, $V1_c$ is rendered greater as illustrated in FIGS. 41(a) through 41(c). For rendering the air/fuel ratio leaner, $V1_c$ is rendered smaller as shown in FIGS. 42(a) through 42(c).

As has been described above, the output V2 of the second sensing element 17B is measured during the air/fuel ratio feedback control at constant time intervals (or whenever the output V1 of the first sensing element 17A crosses the standard value $V1_c$) and the correction of the rich/lean-judging standard value $V1_c$ is effected to make its moving average equal to $V2_c$ whereby the air/fuel ratio is corrected.

Accordingly, the accuracy of the control does not vary even by variations in characteristics from one $O_2$ sensor to another and variations of the characteristics of the $O_2$ sensor along the passage of time and more over, the cleaning efficiency of exhaust gas by the catalytic converter 9 is maintained high. High control reliability can thus be assured like the first embodiment described before.

Even when EGR is not performed or even when EGR is performed at a low rate, a good exhaust gas quality level is achieved. The EGR system can therefore be simplified and in addition, the power performance and drivability are not sacrificed by exhaust gas.

Further, the output V2 of the second sensing element 17B is measured during the air/fuel ratio feedback control at constant time intervals (or whenever the output V1 of the first sensing element 17A crosses the standard value $V1_c$) and the corrections of the response delay time, integral gain, proportional gain and rich/lean-judging standard value are effected to make its moving average equal to $V2_c$, whereby the air/fuel ratio is corrected. The air/fuel ratio control can therefore be performed with still higher reliability and accuracy.

Incidentally, in the first embodiment described above, only one or some of the response delay times, integral gains, proportional gains and rich/lean-judging standard value may be corrected in such a way that the moving average of the output V2 of the second sensing element 17B becomes equal to $V2_c$.c An air/fuel ratio control system according to a second embodiment of this invention will next be described. The output V2 of the second sensing element 17B is measured during the air/fuel ratio feedback control and one or more of the response delay times DLYRL,DLYLR, proportional gains $P_{RL},P_{LR}$ and the integral gains $I_{RL},I_{LR}$ are corrected on the basis of the output V2. Incidentally, the correction of the standard value $V1_c$ for the first sensing element based on the measured value V2 is not performed in the second embodiment.

In the air/fuel ratio feedback control making use of the $O_2$ sensors, the second embodiment also compares the output V1 from the first sensing element 17A with the predetermined standard value $V1_c$ (an intermediate value between the high-level output of the first sensing element 17A and the low-level output thereof being chosen as the standard value $V1_c$ and said standard value $V1_c$ serving as a so-called rich/lean judgement voltage) and renders the air-fuel mixture richer when $V1_c \geq V1$ but makes it leaner when $V1_c \geq V1$.

Figure 43:
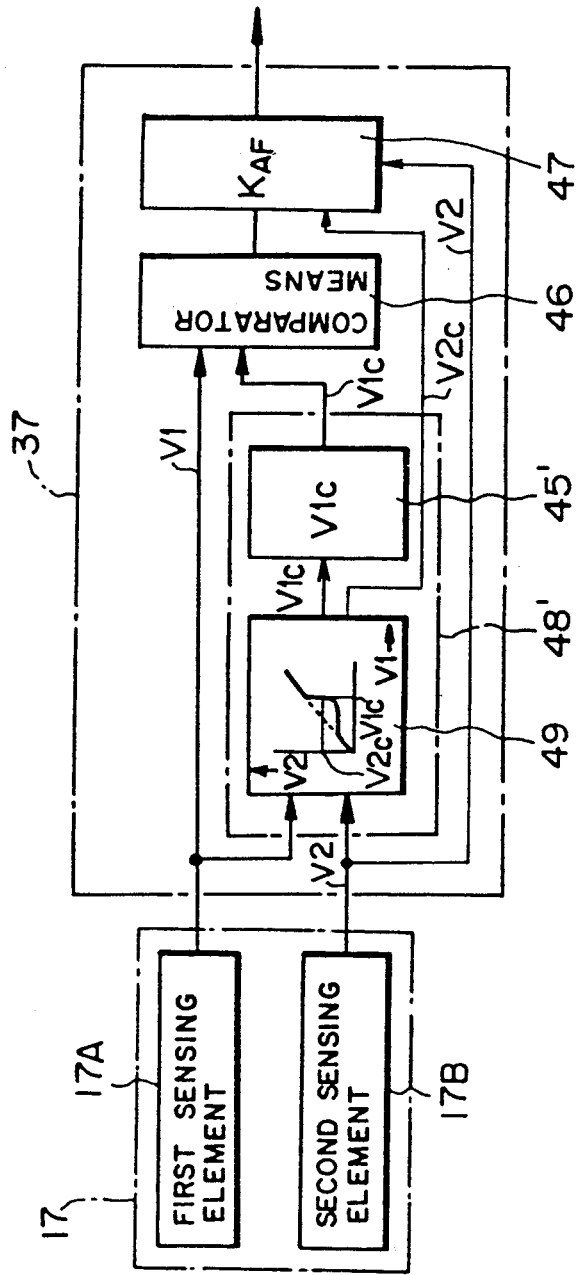
Figure 44A:
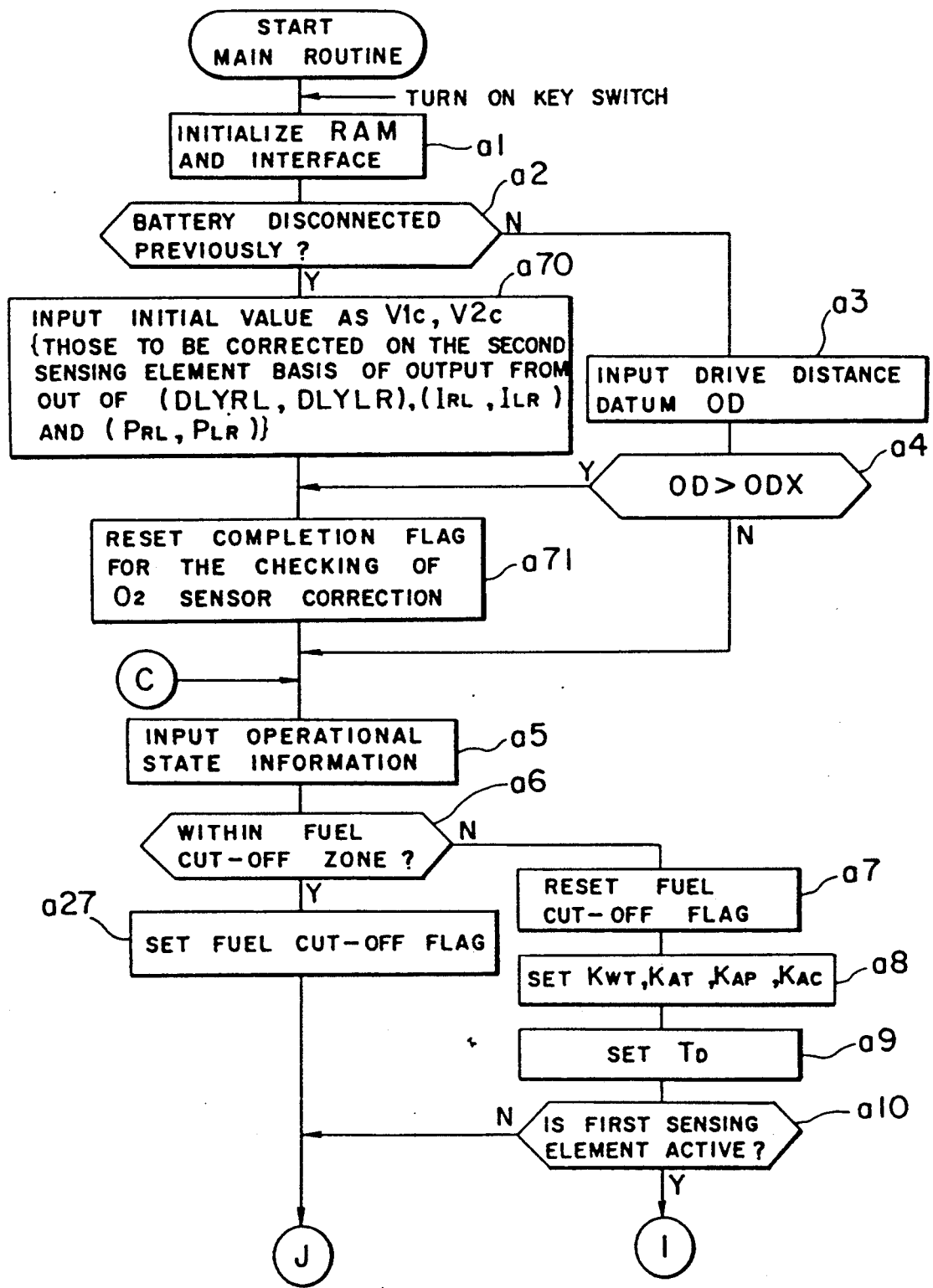
FIGS. 44(a) through 44(e) are respectively flow charts for describing a main routine of the control system.
Figure 44B:
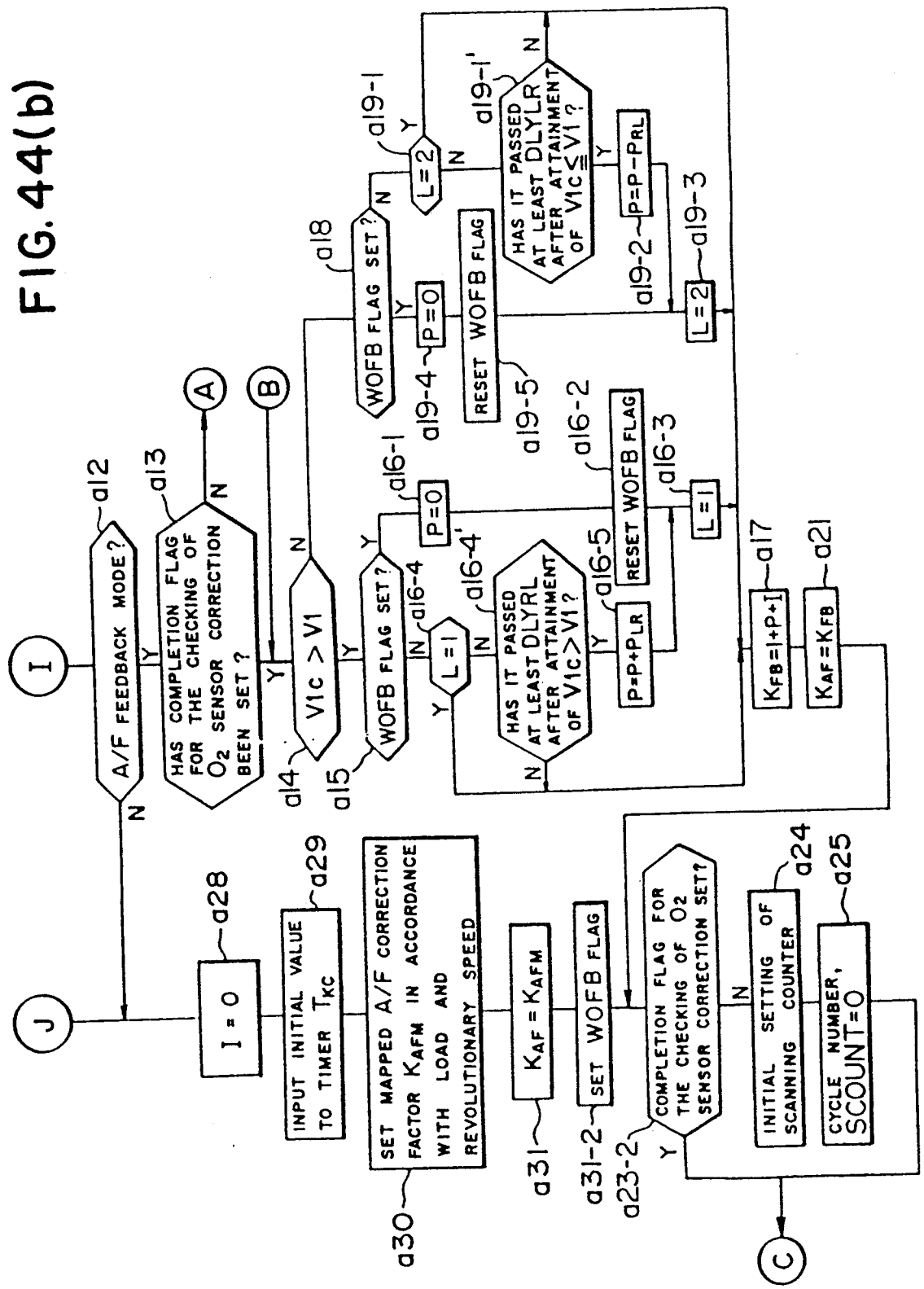
Figure 44C:
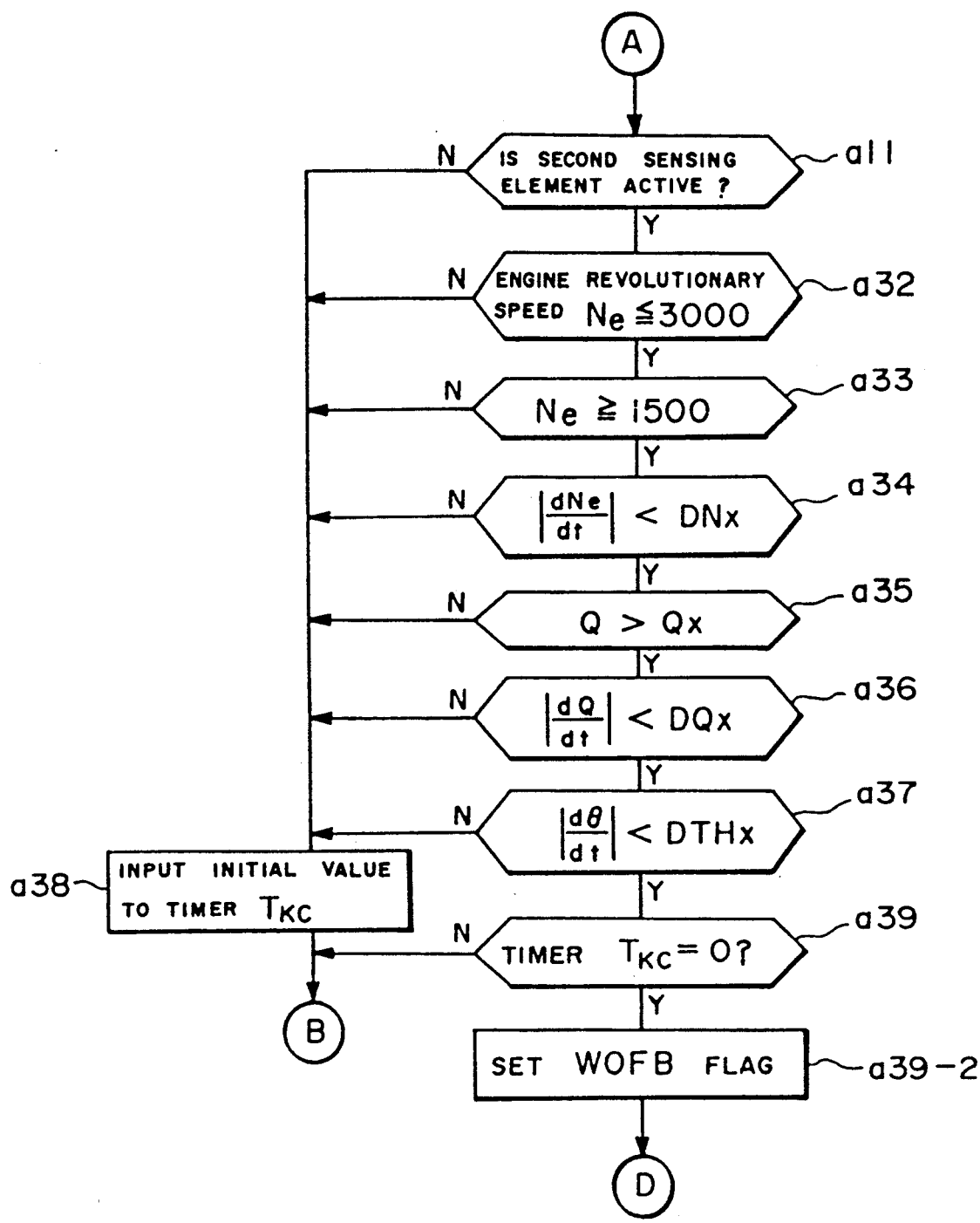
Figure 44D:
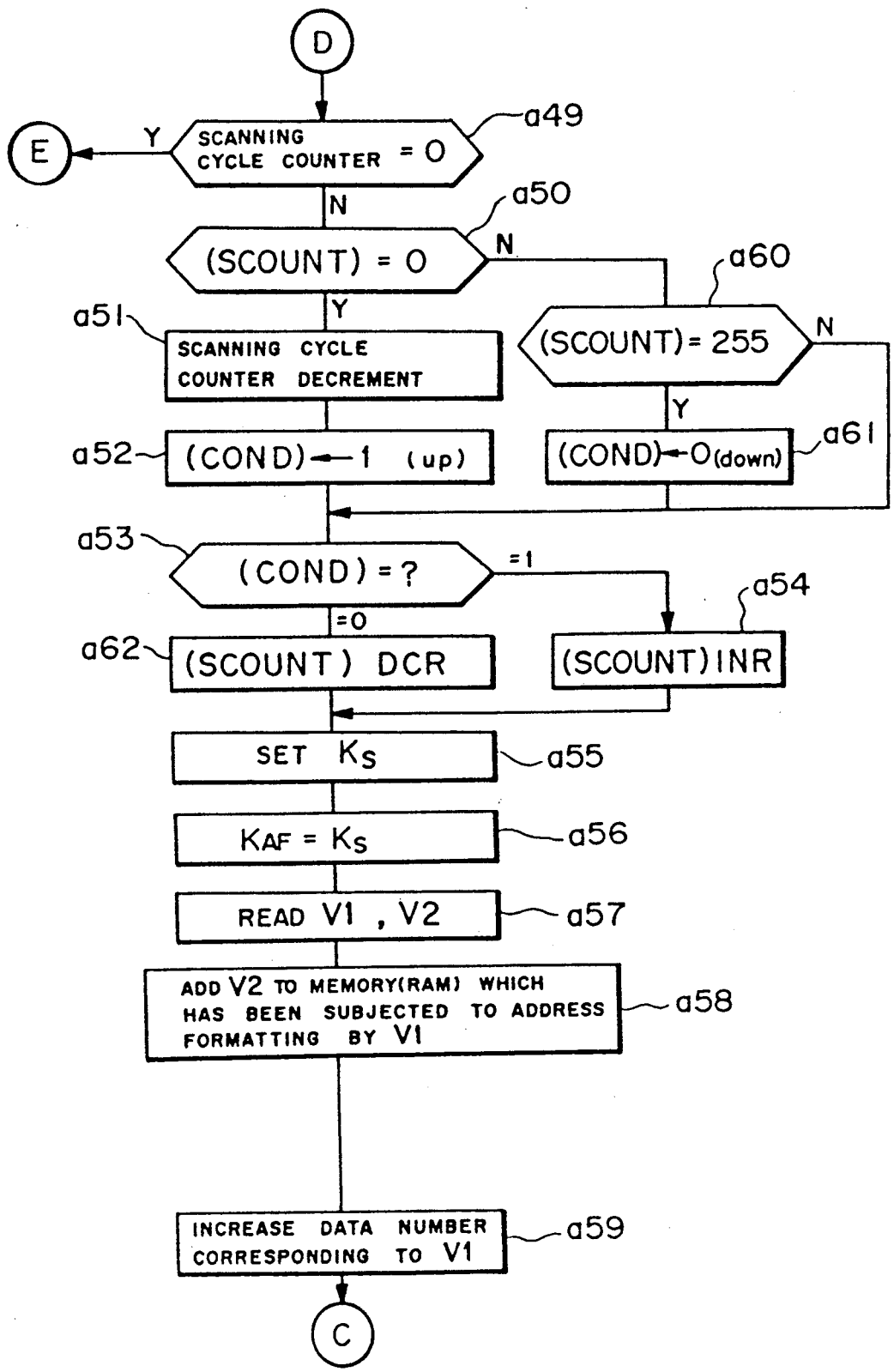
Figure 44E:
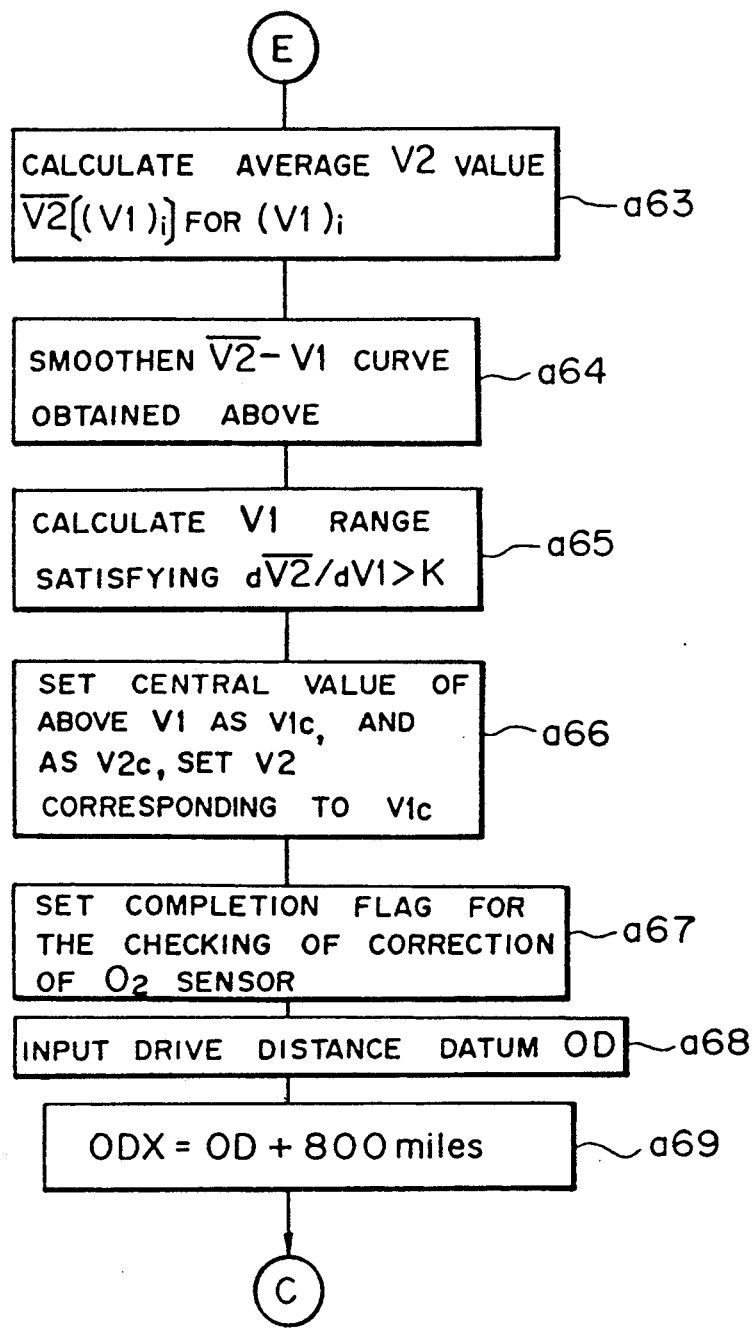

Accordingly, the $O_2$ sensor feedback correction means 37 has, as depicted in FIG. 43, the rich/lean judgement voltage setting means 45' for setting the standard value $V1_c$, the comparator means 46 for comparing the output V1 from the first sensing element 17A with the standard value $V1_c$ from the rich/lean judgement voltage setting means 45', and a correction factor determination means 47 for determining the air/fuel ratio correction factor $K_{AF}$ in accordance with comparison results from the comparator means 46. Different from conventional systems, the present air/fuel ratio control system is also equipped with the standard value changing means 48' for allowing to change the standard values $V1_c,V2_c$ on the basis of the outputs V1 and V2 from the first sensing element 17A and second sensing element 17B, for example, for every predetermined drive distance.

The correction factor determination means 47 includes a means 47A correcting any of the response delay times DLYRL,DLYLR, proportional gains $P_{RL},P_{LR}$ and integral gains $I_{RL},I_{LR}$ on the basis of the output V2 of the second sensing element 17B measured during the air/fuel ratio feedback control.

Incidentally, the above-described V2-V1 characteristics and the response delay times DLYRL, DLYLR, proportional gains $P_{RL},P_{LR}$ and integral gains $I_{RL},I_{LR}$ corrected in accordance with the standard values $V1_c,V2_c$ or the output V2 of the second sensing element 17B are stored in the BURAM 33.

The main routine for changing and renewing the above-described standard values $V1_c,V2_c$ for every predetermined drive distance or after every history of battery disconnection may be illustrated as shown in FIGS. 44(a) through 44(e). Since these flow charts are substantially the same as those depicted in FIGS. 18(a) through 18(e), the same processings as those in FIGS. 18(a) through 18(e) are identified by like step numbers and their description is omitted herein.

A description will next be made of a method for correcting the response delay times DLYRL,DLYLR, proportional gains $P_{RL},P_{LR}$ and integral gains $I_{RL},I_{LR}$ on the basis of the output V2 of the second sensing element and the standard value $V2_c$.

Figure 45:
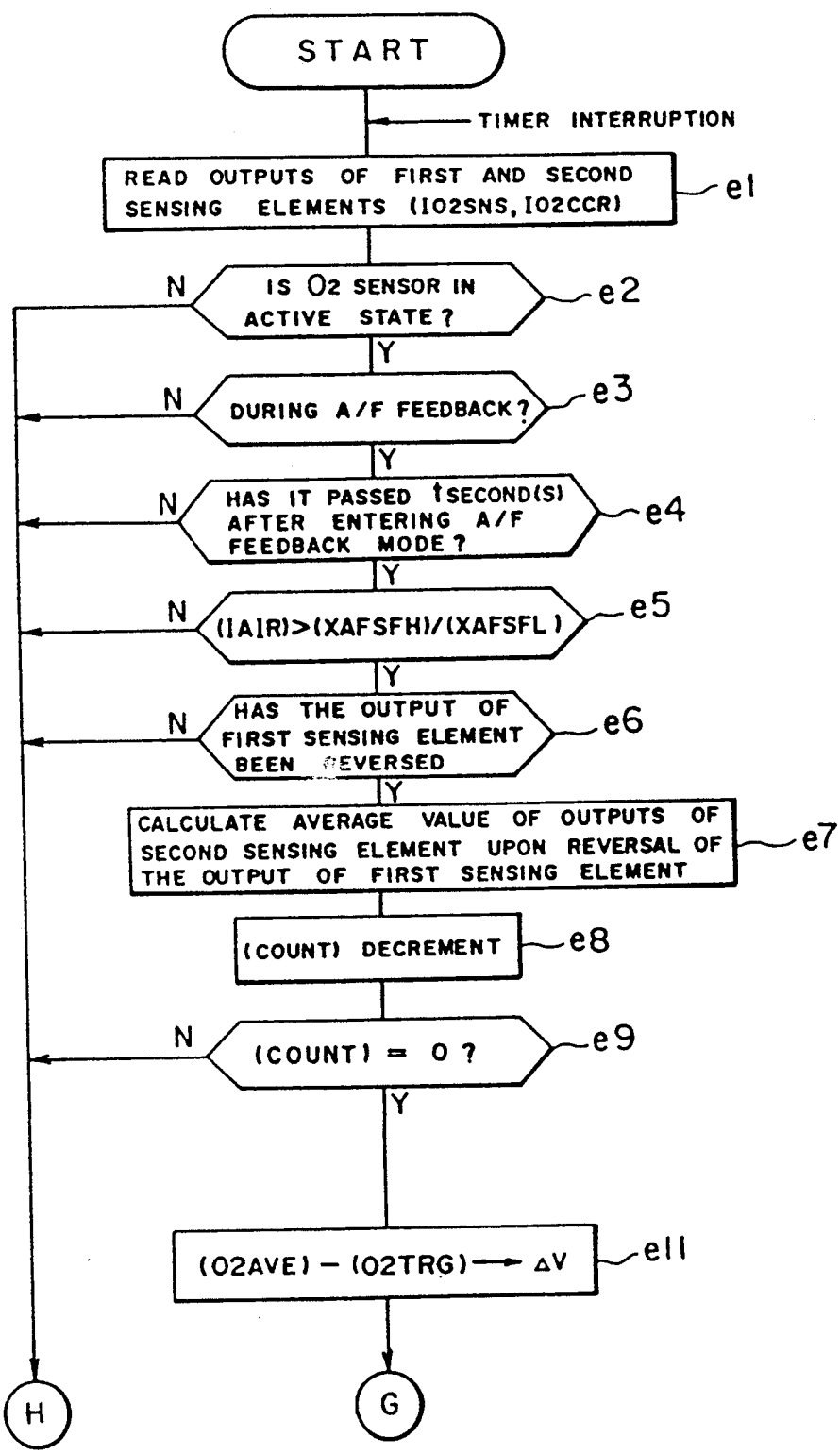

Firstly, from the target output voltage value O2TRG (which corresponds to $V2_c$) of the second sensing element 17B and the average output value O2AVE of the second sensing element 17B at the time of rich/lean reversal of the first sensing element 17A, namely, from the standard value $V2_c$ for the second sensing element and the output V2 of the second sensing element 17B, the deviation $\Delta V$ between these values is determined. A flow chart for determining the deviation $\Delta V$ is similar to that illustrated in FIG. 21 and may be shown as depicted in FIG. 45.

When the deviation $\Delta V$ has been determined as described above, the response delay times, integral gains and proportional gains are corrected by using $\Delta V$.

Figure 46:
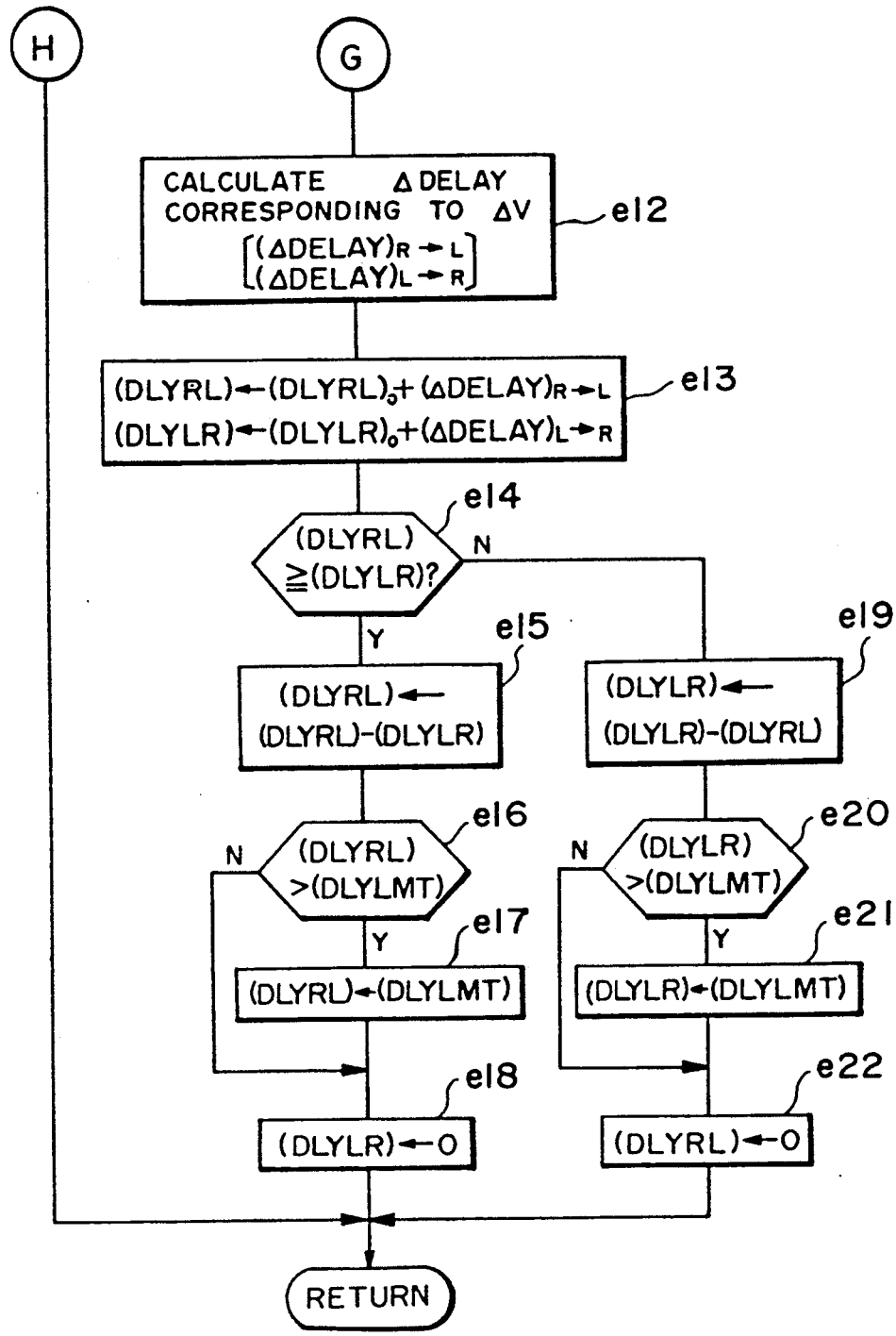

A flow chart for the correction of the response delay times DLYRL,DLYLR is similar to that described above with reference to FIG. 22 and may be illustrated as shown in FIG. 46.

Figure 49A:
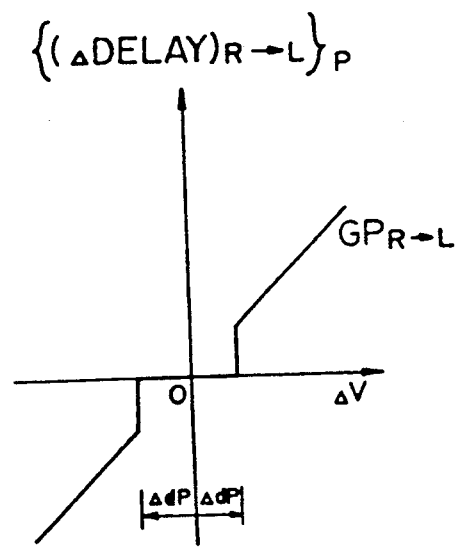
FIGS. 49(a) and 49(b) and FIGS. 50(a) and 50(b) are respectively graphs for describing a correction value for response delay time.
Figure 49B:
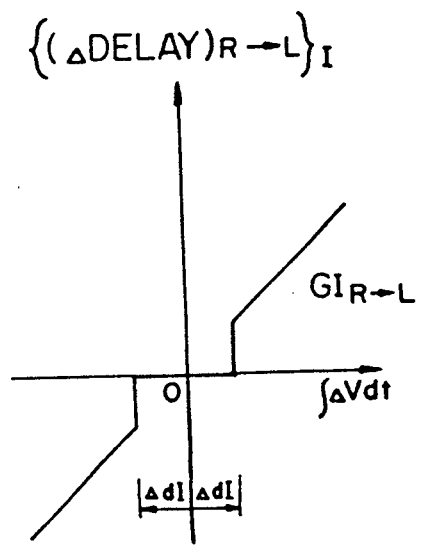
Figure 50A:
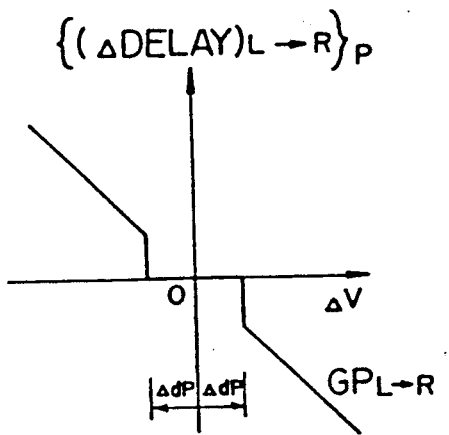
Figure 50B:
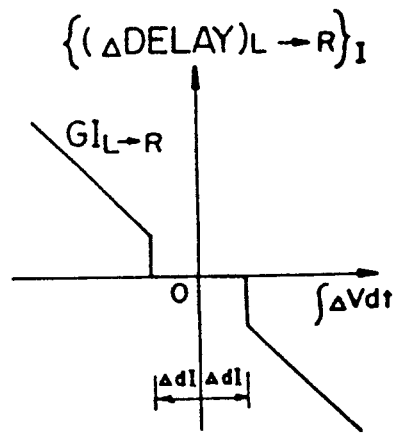

By the way, there are two kinds of delays as $\Delta$DELAY determined in accordance with $\Delta V$ in Step e12 of FIG. 46, one being a delay that takes place when the air/fuel ratio changes from the rich side to the lean side and the other being a delay that occurs when the air/fuel ratio changes from the lean side to the rich side. Correction characteristics for the former delay are similar to those shown in FIGS. 28(a) and 28(b) and may be illustrated as shown in FIGS. 49(a) and 49(b), while those for the latter delay are similar to those depicted in FIGS. 29(a) and 29(b) and may be illustrated as shown in FIGS. 50(a) and 50(b). Functional relations (inclinations and dead zones) shown in these FIGS. 49(a) and 49(b) and FIGS. 50(a) and 50(b) are set in the ROM data.

When DLYRL and DLYLR are corrected on the basis of the output of the second sensing element and the air/fuel ratio is rendered richer, DLYLR is added as shown in FIGS. 55(a) through 55(c) likewise FIGS. 35(a) through 35(c). For rendering the air/fuel ratio leaner, DLYRL is added as illustrated in FIGS. 56(a) through 56(c) likewise FIGS. 36(a) through 36(c).

As has been described above, the output V2 of the second sensing element 17B is measured during the air/fuel ratio feedback control at constant time intervals (or whenever the output V1 of the first sensing element 17A crosses the standard value $V1_c$) and the correction of the response delay time is effected to make its moving average equal to $V2_c$, whereby the air/fuel ratio control is corrected. It is therefore possible to obtain substantially the same effects and advantages as those obtained in each of the preceding embodiment.

Figure 47:
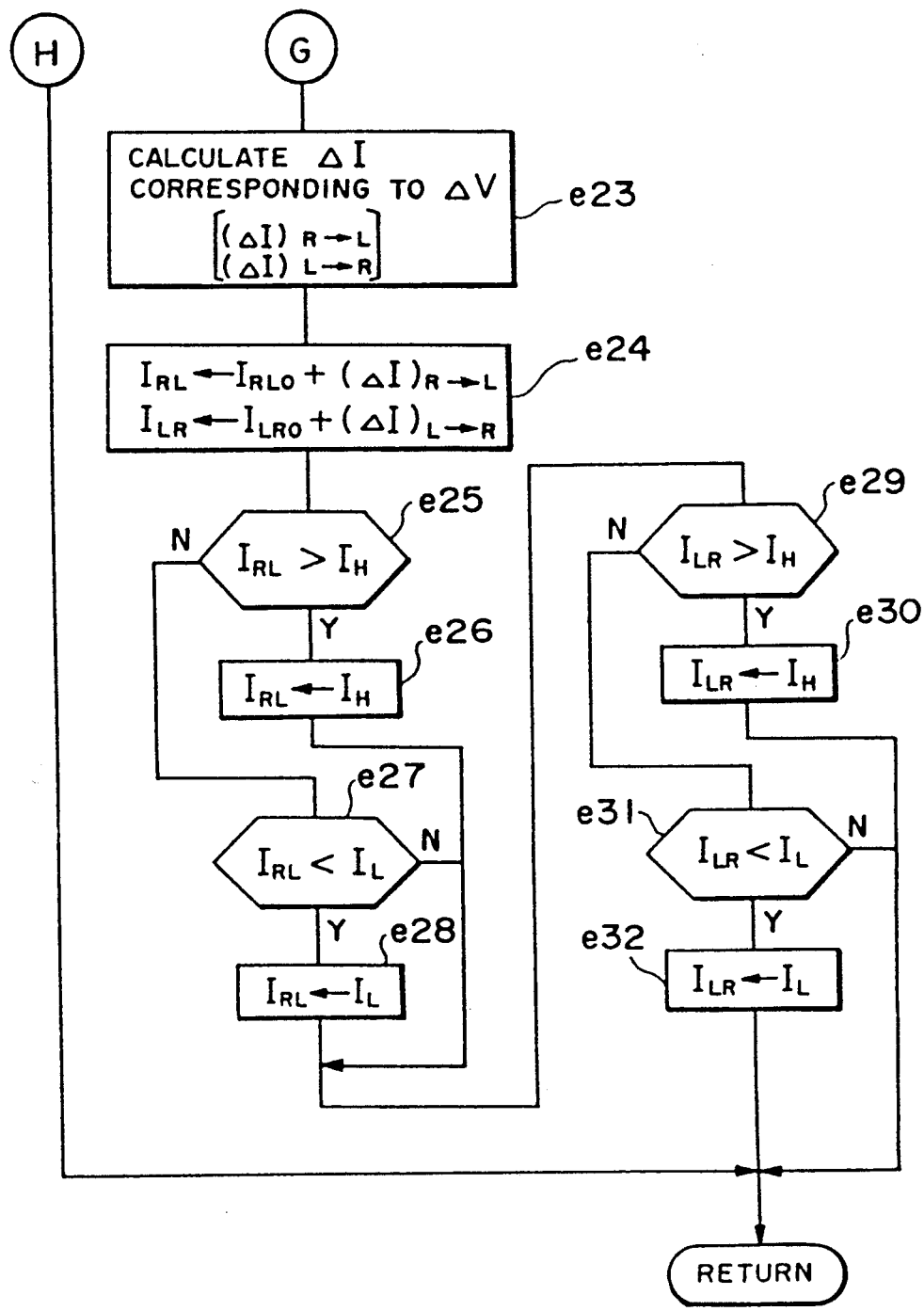

Next, a flow chart for the correction of the integral gains $I_{RL},I_{LR}$ for the air/fuel ratio feedback control is similar to that described before with reference to FIG. 23 and may be illustrated as shown in FIG. 47.

By the way, there are two kinds of integral gains as $\Delta I$ obtained in accordance with $\Delta V$ in Step e23 of FIG.

Figure 51A:
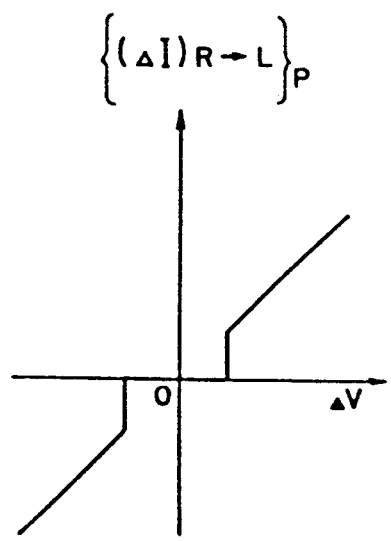
FIGS. 51(a) and 51(b) and FIGS. 52(a) and 52(b) are respectively graphs for illustrating a correction value for the integral gain which is for the air/fuel ratio feedback control.
Figure 51B:
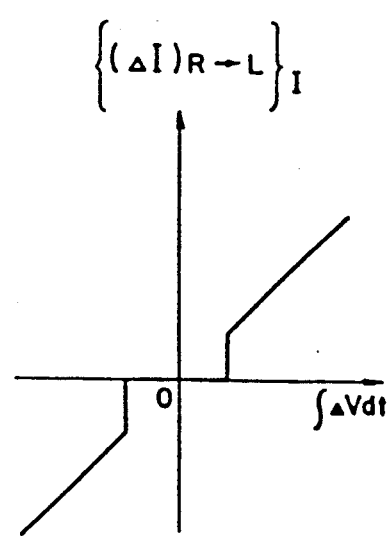
Figure 52A:
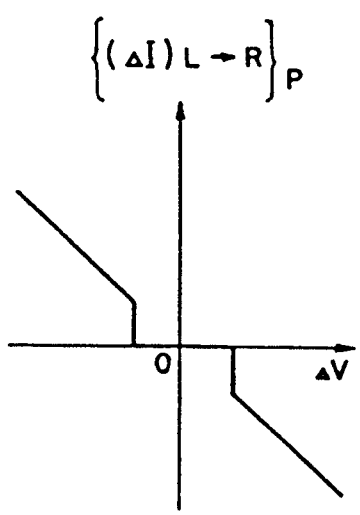
Figure 52B:
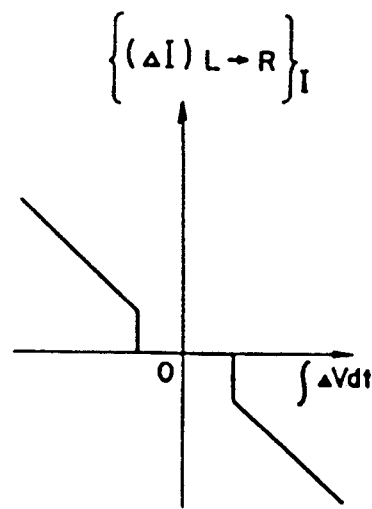

47, one being an integral gain for the change of the air/fuel ratio from the rich side to the lean side and the other being an integral gain for the change of the air/fuel ratio from the lean side to the rich side. Correction characteristics for the former delay are similar to those shown in FIGS. 30(a) and 30(b) and may be illustrated as shown in FIGS. 51(a) and 51(b), while those for the latter delay are similar to those depicted in FIGS. 31(a) and 31(b) and may be illustrated as shown in FIGS. 52(a) and 52(b). Functional relations (inclinations and dead zones) shown in these FIGS. 51(a) and 51(b) and FIGS. 52(a) and 52(b) are also set in the ROM data.

Figure 57A:
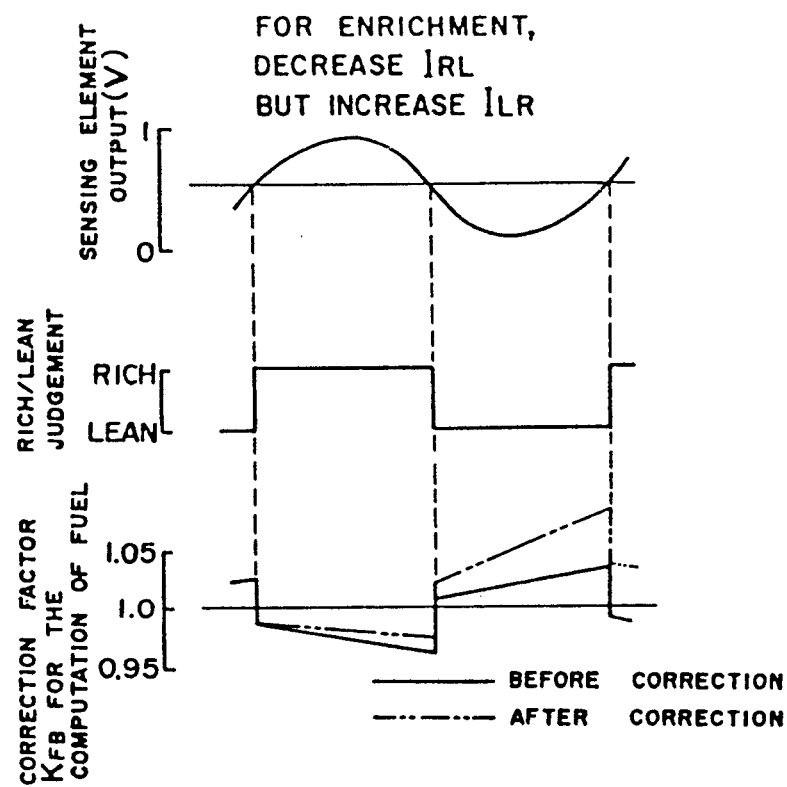
Figure 58A:
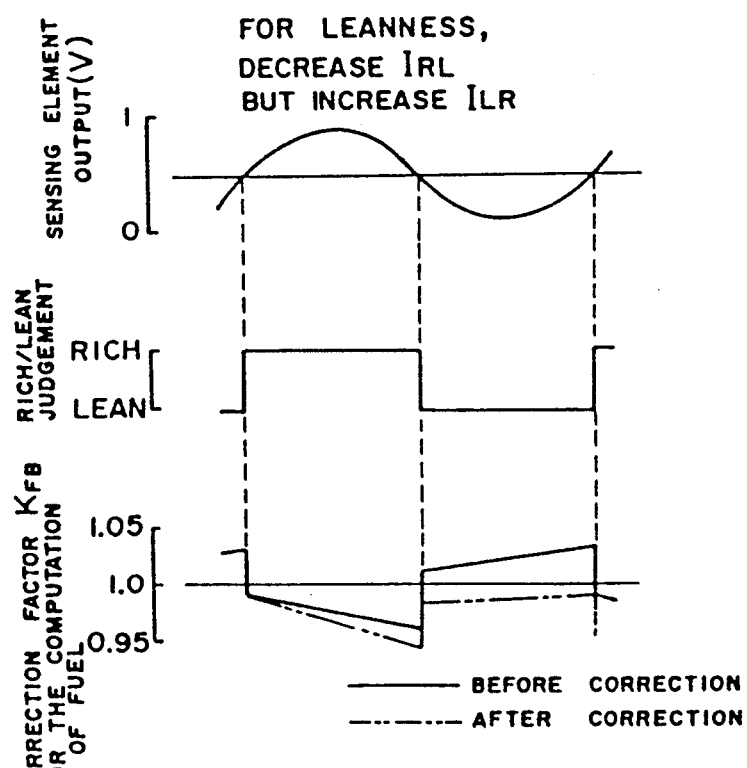

When $I_{RL}$ and $I_{LR}$ are corrected on the basis of the output of the second sensing element 17B and the air/fuel ratio is rendered richer, $I_{RL}$ is rendered smaller and at the same time, $I_{LR}$ is rendered greater as illustrated in FIGS. 57(a) through 57(c) likewise FIGS. 37(a) through 37(c). For rendering the air/fuel ratio leaner, $I_{RL}$ is rendered greater and at the same time, $I_{LR}$ is rendered smaller as illustrated in FIGS. 58(a) through 58(c) likewise FIGS. 38(a) through 38(c).

As has been described above, the output V2 of the second sensing element 17B is measured during the air/fuel ratio feedback control at constant time intervals (or whenever the output V1 of the first sensing element 17A crosses the standard value $V1_c$) and the correction of the integral gain is effected to make its moving average equal to $V2_c$, whereby the air/fuel ratio feedback control is corrected. Here again, it is possible to bring about substantially the same effects and advantages as the aforementioned correction of the response delay times.

Figure 48:
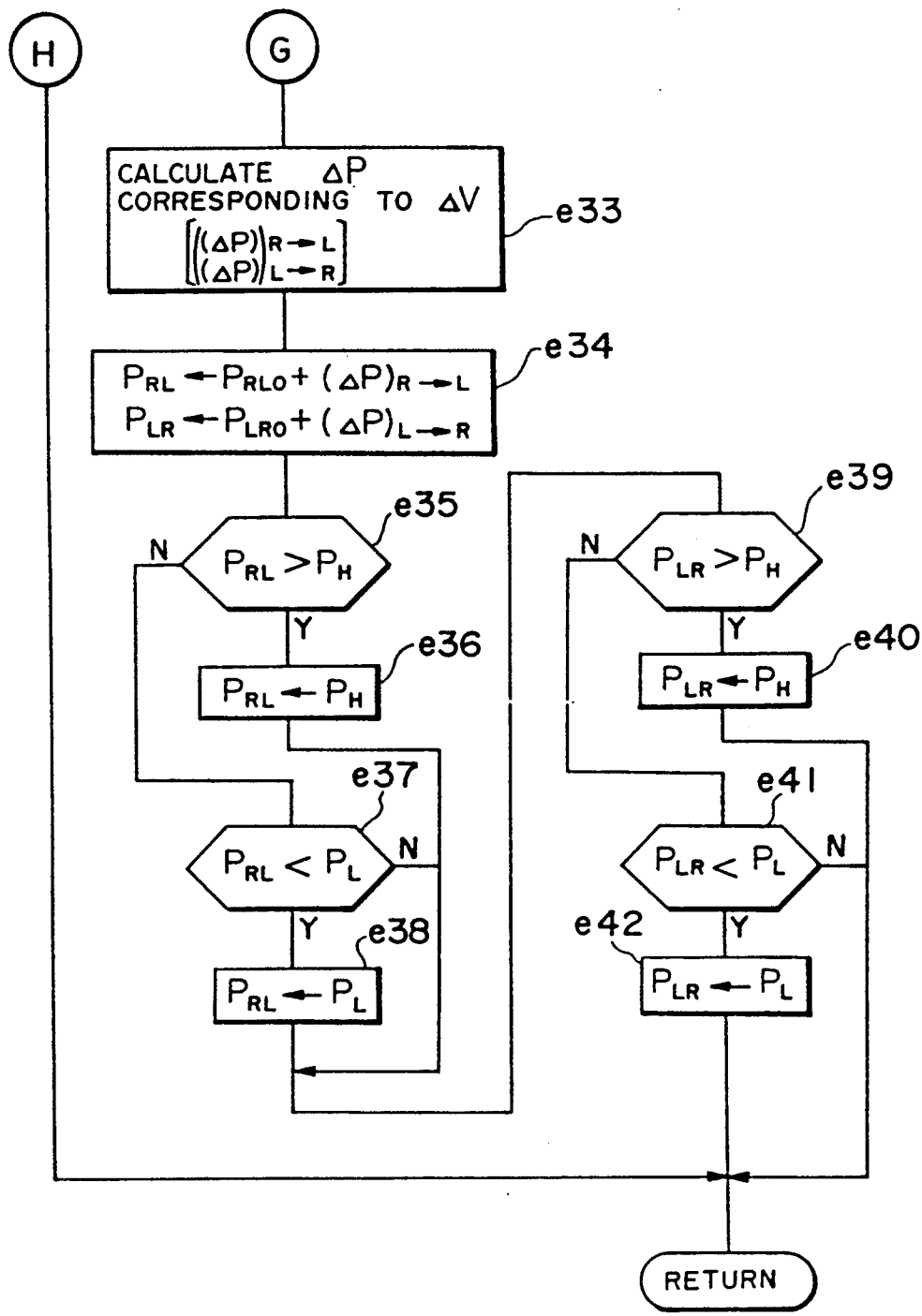

Next, a flow chart for the corrections of the proportional gains $P_{RL}, P_{LR}$ for the air/fuel ratio feed back control is similar to that described above with reference to FIG. 24 and may be illustrated as shown in FIG. 48.

Figure 53A:
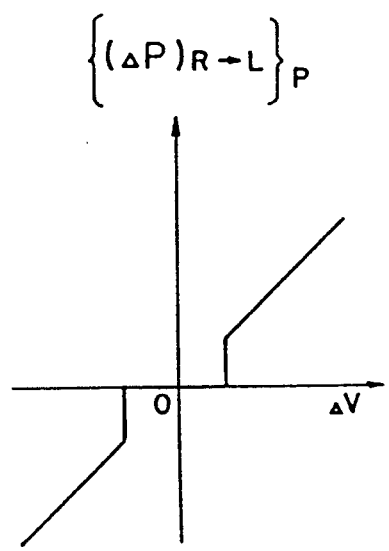
FIGS. 53(a) and 53(b) and FIGS. 54(a) and 54(b) are respectively graphs for illustrating a correction value for the proportional gain which is for the air/fuel ratio feedback control.
Figure 53B:
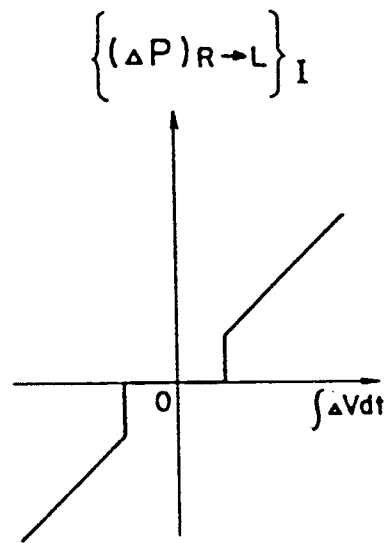
Figure 54A:
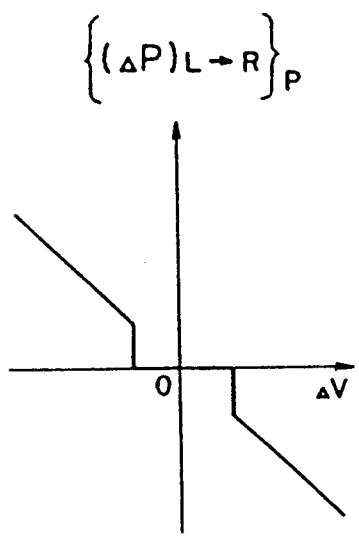
Figure 54B:
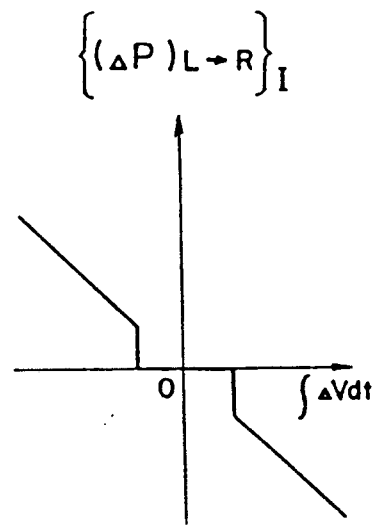

By the way, there are two kinds of proportional gains as $\Delta P$ obtained in accordance with $\Delta V$ in Step e33 of FIG. 48, one being a proportional gain for the change of the air/fuel ratio from the rich side to the lean side and the other being a proportional gain for the change of the air/fuel ratio from the lean side to the rich side. Correction characteristics for the former proportional gain are similar to those depicted in FIGS. 32(a) and 32(b) and may be illustrated as shown in FIGS. 53(a) and 53(b), while those for the latter proportional gain are similar to those depicted in FIGS. 33(a) and 33(b) and may be depicted as shown in FIGS. 54(a) and 54(b). Functional relations (inclinations and dead zones) shown in these FIGS. 53(a) and 53(b) and FIGS. 54(a) and 54(b) are also set in the ROM data.

When $P_{RL}$ and $P_{LR}$ are corrected on the basis of the output of the second sensing element 17B and the air/fuel ratio is rendered richer, $P_{RL}$ is rendered smaller and at the same time, $P_{LR}$ is rendered greater as illustrated in FIGS. 59(a) through 59(c) likewise FIGS. 39(a) through 39(c). For rendering the air/fuel ratio leaner, $P_{RL}$ is rendered greater and at the same time, $P_{LR}$ is rendered smaller as illustrated in FIGS. 60(a) through 60(c) likewise FIGS. 40(a) through 40(c).

As has been described above, the output V2 of the second sensing element 17B is measured during the air/fuel ratio feedback control at constant time intervals (or whenever the output V1 of the first sensing element 17A crosses the standard value $V1_c$) and the correction of the proportional gain is effected to make its moving average equal to $V2_c$, whereby the air/fuel ratio feedback control is corrected. Here again, it is possible to bring about substantially the same effects and advantages as the aforementioned correction of the response delay times or integral gains.

Incidentally, in the second embodiment described above, only one or some of the response delay times, integral gains and proportional gains may be corrected in such a way that the moving average of the output V2 of the second sensing element 17B becomes equal to $V2_c$.

Figure 61:
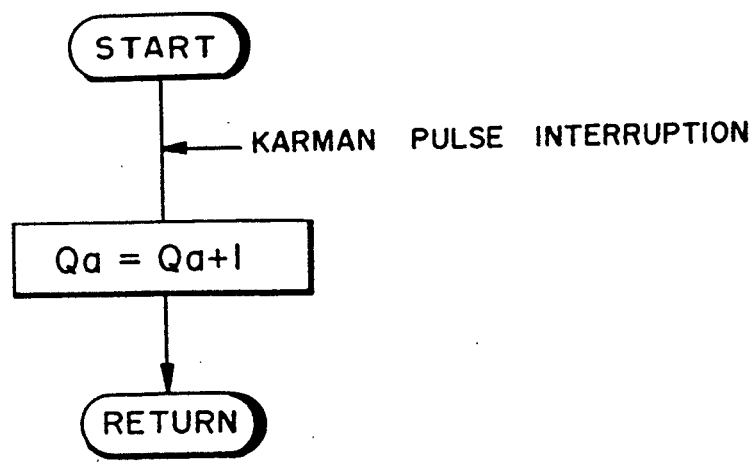

In the first and second embodiments described above, the average output value 02AVE of the second sensing element 17B was renewed in Step e6 and Step e7 of the flow charts of FIGS. 21 and 45 whenever the output of the first sensing element 17A was reversed. This renewal may however be performed whenever the quantity of intake air reaches a predetermined value (namely, the cumulative value of data on the quantity of intake air reaches the predetermined value).

Where discrete pulses of a frequency corresponding to an intake air quantity are inputted to the ECU 23 from the airflow sensor (Karman vortex flow meter) 11 as shown in FIG. 2, the flow chart of FIGS. 61 and 62 may be used instead of those shown in FIGS. 21 and 45. Namely, in a routine which is performed whenever a pulse synchronous with the production of a Karman vortex reaches as illustrated in FIG. 61, an additional step is provided to cumulate the number of such pulses. In Step e60 of the timer interruption routine shown in FIG. 62, it is also judged whether the cumulated value of the pulses has exceeded a predetermined value $Q_x$. If this is the case, after the cumulative value datum $Q_a$ is reset in Step e61, the average output value of the second sensing element is renewed in Step e7' like Step e7 described above.

If a judgement of "NO" is made in any one of Steps e2–e5 of FIG. 62, the cumulative value datum $Q_a$ is reset to 0 in Step e62.

Regarding the symbols for the steps and the like in FIG. 62, those identified by the same symbols as those employed in FIGS. 21 and 45 indicate the same steps and the like. Incidentally, Step e5 may be omitted in the flow chart of FIG. 62.

A third embodiment of this invention will now be described. The output V2 of the second sensing element 17B is measured during the air/fuel ratio feedback control and another feedback correction factor $K_{FB2}$ different from the above-described feedback correction factor $K_{FB}$ is obtained on the basis of the output V2. Namely, the correction factor $K_{FB2}$ is obtained by a map or computation in accordance with $\Delta V$ determined in FIG. 21, 45 or 62 (see FIG. 64).

Figure 63A:
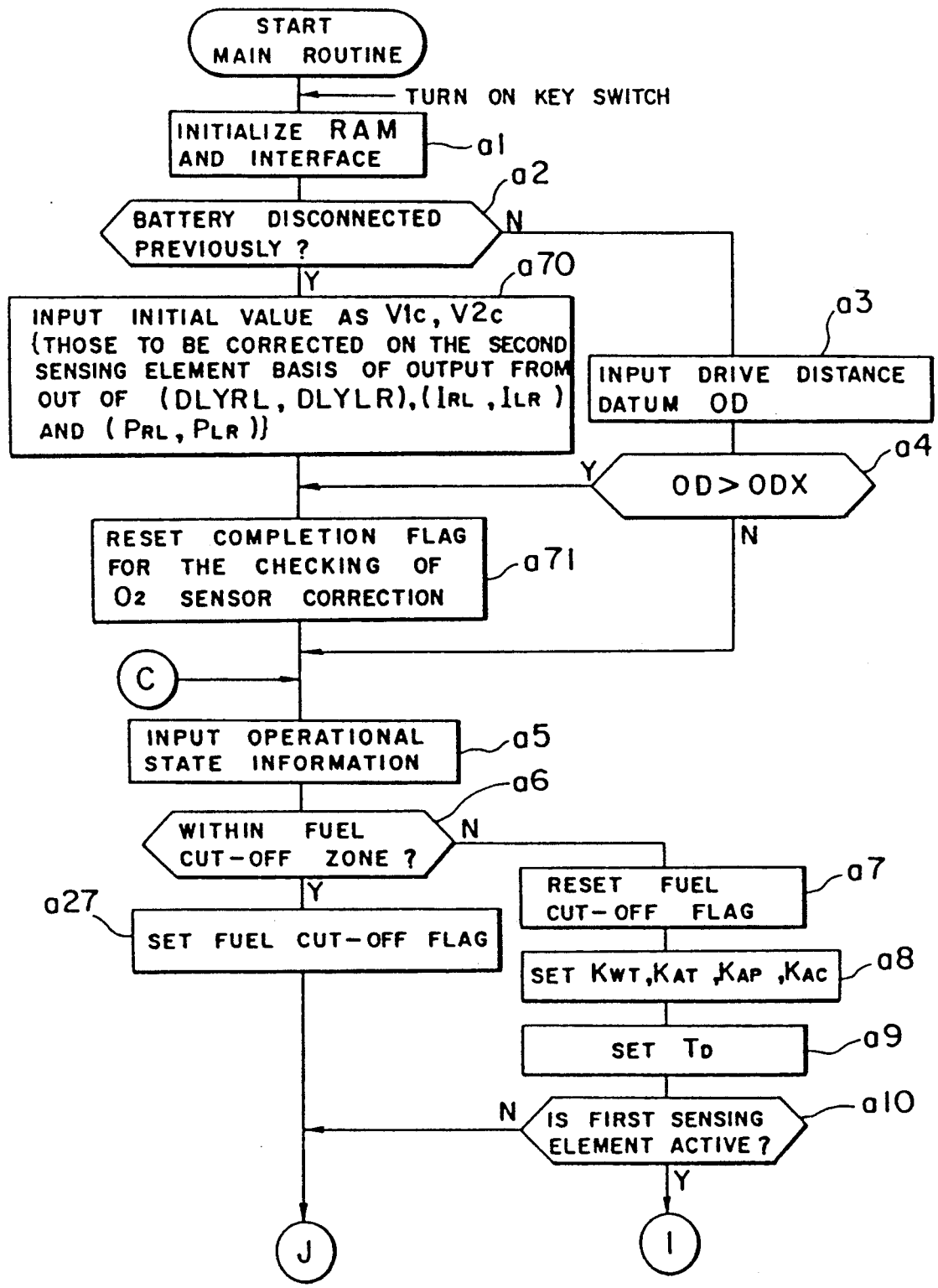
FIGS. 63(a) and 63(b) are flow charts for describing a part of a main routine of the control system.
Figure 63B:
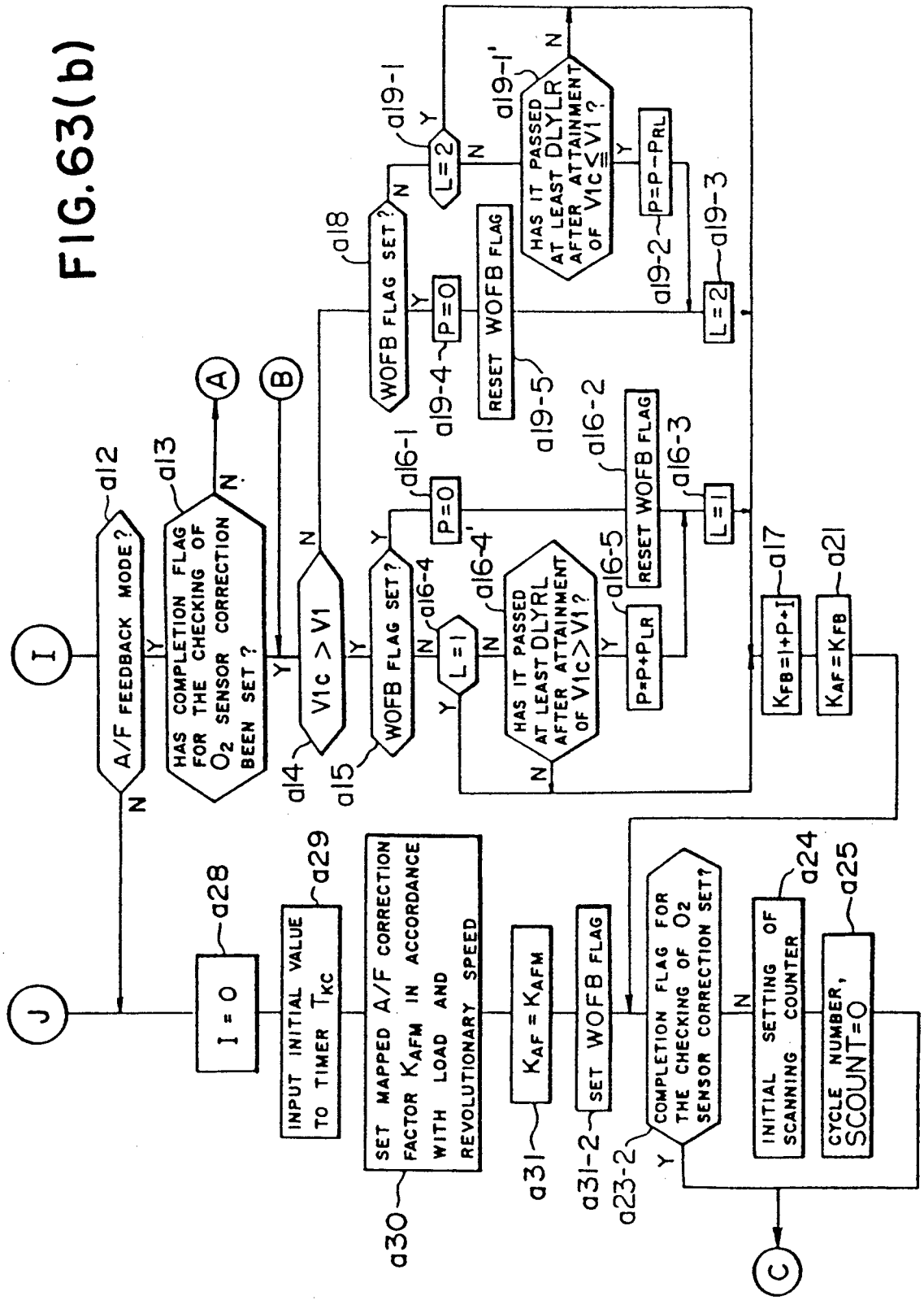
Figure 64:
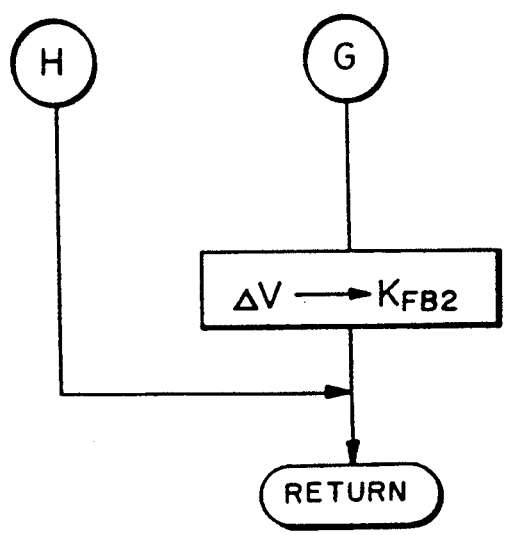

In this case, the correction factor $K_{FB}$ determined in Step a17 of FIG. 63 is multiplied with the correction factor $K_{FB2}$, which has been obtained in FIG. 64, in Step a21 of FIG. 63 so as to use the resulting product as $K_{FB}$.

The other parts of the main flow are identical to their corresponding parts illustrated in FIGS. 18(b) through 18(e) or FIGS. 44(b) through 44(e).

In this manner, it is also possible to obtain substantially the same effects and advantages as those obtained in each of the preceding embodiments.

A fourth embodiment of this invention will now be described. The standard values $V1_c, V2_c$ for the first and second sensing elements 17A, 17B are not changed for every predetermined drive distance on the basis of the outputs from both sensing elements 17A, 17B. A fragmentary block diagram for this control may be illustrated as shown in FIG. 65.

Figure 65:
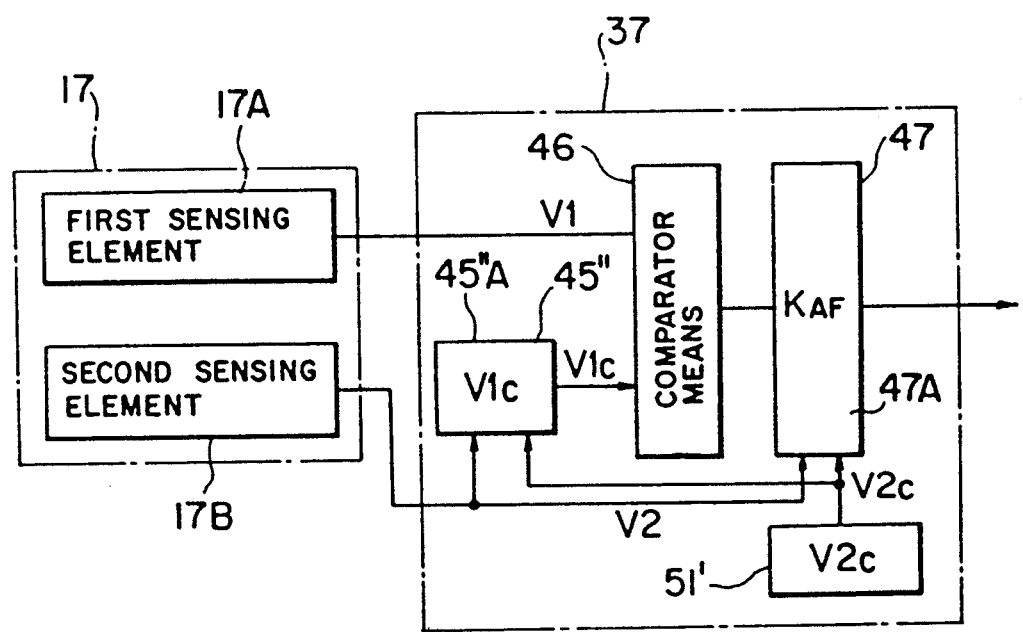

Accordingly, the $O_2$ sensor feedback correction means 37 has, as shown in FIG. 65, a rich/lean judgement voltage setting means 45" for setting the standard value $V1_c$ for the first sensing element, the comparator means 46 for comparing the output V1 from the first sensing element 17A with the standard value $V1_c$ from the rich/lean judgement voltage setting means 45" and the correction factor determination means 47 for determining the air/fuel ratio correction factor $K_{AF}$ in accordance with comparison results from the comparator means 46. The present air/fuel ratio control system is also equipped with the second standard value setting means 51' for setting the standard value $V2_c$ for the second sensing element.

Further, a standard value $V2_c$ signal for second sensing element from the standard value setting means 51 is inputted to the rich/lean judgement voltage setting means 45" and correction factor determination means 47. These rich/lean judgement voltage setting means 45" and correction factor determination means 47 also function respectively as air/fuel ratio control correction means 45"A,47A for effecting a correction to the air/fuel ratio control which is performed by the air/fuel control means on the basis of the results of a comparison between the standard value $V2_c$ for the second sensing element and the output V2 from the second sensing element 17B.

Namely, the air/fuel ratio control correction means 45"A in the rich/lean judgement voltage setting means 45" can correct the rich/lean-judging standard value $V1_c$ on the basis of the deviation ΔV between the standard value $V2_c$ for the second sensing element and an output V2 of the second sensing element 17B measured during the air/fuel feedback control. On the other hand, the air/fuel ratio control correction means 47A in the correction factor determination means 47 can correct any of the response delay times DLYRL,DLYLR, proportional gains $P_{RL},P_{LR}$ and integral gains $I_{RL},I_{LR}$ on the basis of the deviation ΔV between the standard value $V2_c$ for the second sensing element and an output V2 of the second sensing element 17B measured during the air/fuel feedback control.

Here, flow charts for determining the deviation ΔV between the standard value $V2_c$ for the second sensing element and an output V2 from the second sensing element 17B may be illustrated as shown in FIGS. 21, 45 and 62. A flow chart for correcting the rich/lean-judging standard value $V1_c$ on the basis of the deviation IV may be illustrated as depicted in FIG. 25. Further, flow charts for correcting the response delay times DLYRL,DLYLR, proportional gains $P_{RL},P_{LR}$ and integral gains $I_{RL},I_{LR}$ on the basis of the deviation ΔV described above may be illustrated as depicted in FIGS. 22 through 24 or FIGS. 46 through 48.

Incidentally, the rich/lean judgement voltage $V1_c$, response delay times DLYRL,DLYLR, proportional gains $P_{RL},P_{LR}$ and integral gains $I_{RL},I_{LR}$ corrected in accordance with the standard value $V2_c$ or the output V2 of the second sensing element 17B are stored in the BURAM 33.

Figure 66:
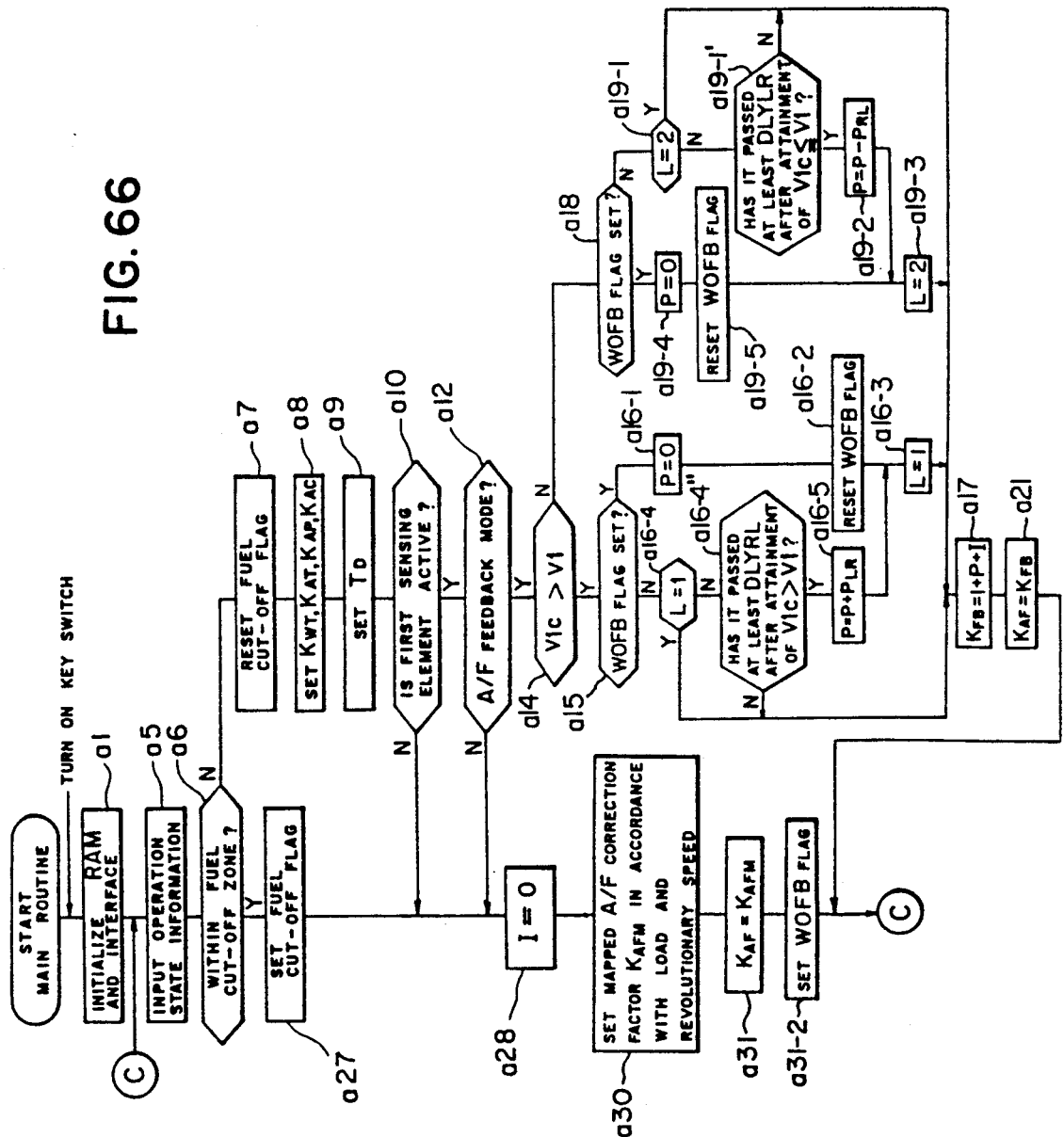

By the way, the main routine according to the fourth embodiment may be illustrated as shown in FIG. 66. This flow chart is equal to that shown in FIGS. 18(a) and 18(b) or FIGS. 44(a) and 44(b) except for the omission of the steps required to change the standard values $V1_c,V2_c$ for the first and second sensing elements 17A,17B at every predetermined drive distance on the basis of outputs from both the first and second sensing elements 17A,17B. Specifically, Steps a2, a3, a4, a13, a23-2, a24, a25, a29, a70 and a71 have been omitted.

In this manner, the accuracy of the control does not vary even by variations in characteristics from one $O_2$ sensor to another and variations of the characteristics of each $O_2$ sensor along the passage of time and moreover, the efficiency of exhaust gas cleaning by the catalytic converter can be maintained high. High control reliability can thus be assured.

In the above description, only one or some of the response delay time, integral gain, proportional gain and rich/lean-judging standard value $V1_c$ may be corrected in such a way that the moving average of the output V2 of the second sensing element 17B becomes equal to $V2_c$.

Figure 67:
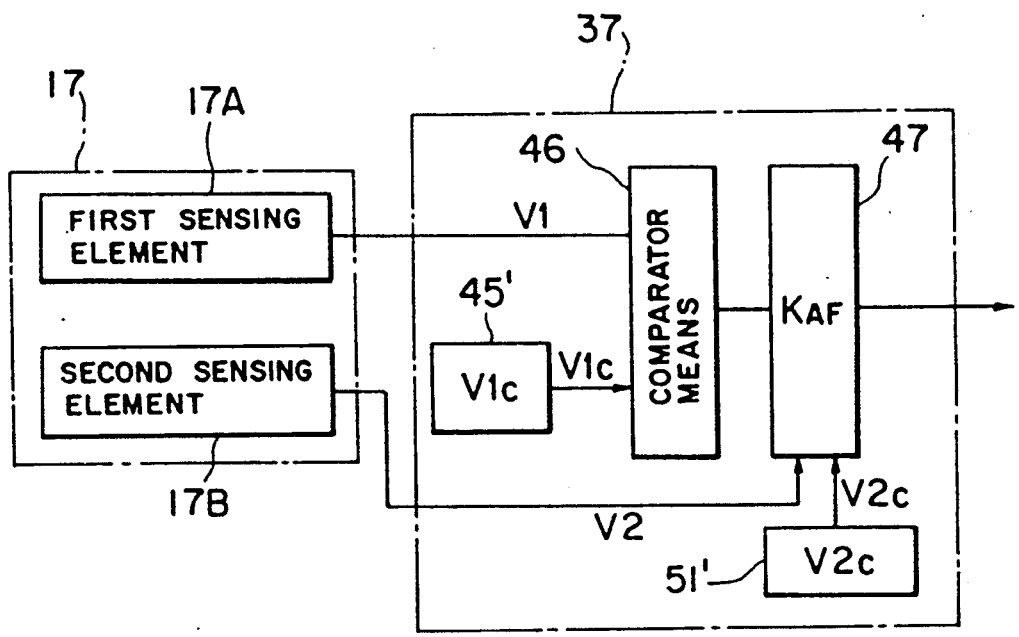
FIG. 67 is a fragmentary block diagram for showing an air/fuel ratio control system according to a fifth embodiment of this invention, which is suitable for use with an internal combustion engine.

Although the fourth embodiment corresponds to the first embodiment described above, the rich/lean judgement voltage setting means 45" is not provided with the air/fuel ratio control correction means 45'A, in other words, the rich/lean-judging standard value $V1_c$ is not corrected based on the deviation ΔV of an output V2, which has been produced by the second sensing element 17B and measured during the air/fuel feedback control, from the standard value $V2_c$ for the second sensing element. The standard value $V1_c$ may also be set as a fixed value similar to the standard value $V2_c$, and the air/fuel ratio control correction means 47A in the correction factor determination means 47 may correct any of the response delay times DLYRL,DLYLR, proportional gains $P_{RL},P_{LR}$ and integral gains $I_{RL},I_{LR}$ on the basis of the deviation ΔV of an output V2 which has been produced by the second sensing element 17B and measured during the air/fuel feedback control, from the standard value $V2_c$ for the second sensing element. In this case, the fragmentary block diagram for the control may be illustrated as shown in FIG. 67. Namely, the present embodiment can be considered to correspond to the second embodiment.

Accordingly, a flow chart for determining the deviation ΔV of an output V2, which has been produced by the second sensing element 17B and measured during the air/fuel feedback control, from the standard value $V2_c$ for the second sensing element may be illustrated as shown in FIG. 45. Further, flow charts for correcting the response delay times DLYRL,DLYLR, proportional gains $P_{RL},P_{LR}$ and integral gains $I_{RL},I_{LR}$ may be illustrated as shown in FIGS. 46 through 48, respectively.

In this case, the main routine may also be illustrated as shown in FIG. 66.

In this manner, the accuracy of the control does not vary even by variations in characteristics from one $O_2$ sensor to another and variations of the characteristics of each $O_2$ sensor along the passage of time and moreover, the efficiency of exhaust gas cleaning by the catalytic converter is maintained high. High control reliability can thus be assured.

Incidentally, in the above, one or some of the response delay times, integral gains and proportional gains may be corrected in such a way that the moving average of the output V2 of the second sensing element 17B becomes equal to $V2_c$.

In the first and second embodiments, only the standard value $V1_c$ or $V2_c$ may be renewed at every predetermined drive distance to perform learning.

It is possible to use, as O₂ sensors those of a type other than the stacked type. Instead of the first and second O₂ sensors integrated together, first and second O₂ sensors enclosed in separate casings may also be used.

Further, the present invention can be applied to any system which performs a feedback control by one or more O₂ sensors. Needless to say, this invention can be applied not only to engine systems of the MPI system but also to engine systems of the SPI (single point fuel injection) system.

In the above-described embodiments, the reference electrodes are provided on the side wall of the base member, said side wall being to be positioned on the side of the atmosphere. This side wall of the base member may however be exposed to reference conditions, for example, to a chamber isolated from the atmosphere and having an oxygen-containing atmosphere.

We claim:

1. An air/fuel ratio control system for an internal combustion engine, comprising:
   a first oxygen density sensor element for arrangement on the upstream side of a catalytic converter so as to detect the density of oxygen in exhaust gas, said catalytic converter being provided in an exhaust system of the internal combustion engine and adapted to clean the exhaust gas;
   a second oxygen density sensor element for arrangment on the upstream side of the catalytic converter, said second oxygen density having a slower detection response speed in comparison with the first oxygen density sensor element;
   an air/fuel ratio control means for controlling the air/fuel ratio of the internal combustion engine on the basis of results of a comparison between a detection value from the first oxygen density sensor element and a predetermined standard value; and
   an air/fuel ratio control correction means for effecting a correction to the air/fuel ratio control by the air/fuel ratio control means on the basis of results of comparison between a detection value from the second oxygen density sensor element and a second standard value for the second oxygen density sensor element;
   wherein the second standard value is set as a predetermined fixed value.

2. An air/fuel ratio control system for an internal combustion engine, comprising:
   an oxygen density sensor equipped integrally with a first oxygen density sensor element and a second oxygen density sensor element adapted to detect at different detection response speeds the density of oxygen in exhaust gas on the upstream side of a catalytic converter, said catalytic converter being provided in an exhaust system of the internal combustion engine and adapted to clean the exhaust gas;
   an air/fuel ratio control means for controlling the air/fuel ratio of the internal combustion engine on the basis of results of a comparison between a detection value from the first oxygen density sensor element having a faster detection response speed in the oxygen density sensor and a predetermined standard value; and
   an air/fuel ratio control correction means for effecting a correction to the air/fuel control by the air/fuel ratio control means on the basis of results of a comparison between a detection value from the second oxygen density sensor element having a slower detection response speed in the oxygen density sensor and a predetermined fixed value for the second oxygen density sensor element.

3. The air/fuel ratio control system as claimed in claim 2, wherein said first oxygen density sensor element and said second oxygen density sensor element are provided on a common base member.

4. The air/fuel ratio control system as claimed in claim 2, wherein said oxygen density sensor comprises a base member composed of a solid electrolyte, a first measuring electrode provided on a side wall of the base member, said side wall being exposed to the exhaust gas, a second measuring electrode covered with a catalytic component and provided on said side wall of the base member, and at least one reference electrode arranged on another side wall of the base member in an opposed relation to each of the first and second measuring electrodes, said another side wall being exposed to reference conditions.

5. The air/fuel ratio control system as claimed in claim 2, wherein said oxygen density sensor comprises a base member composed of a solid electrolyte, a first measuring electrode provided on a side wall of the base member exposed to the exhaust gas, a diffusion chamber formed in the base member to receive the exhaust gas through a small-diameter passage, a second measuring electrode arranged within the diffusion chamber, a catalyst provided in the diffusion chamber to cover the second measuring electrode and at least one reference electrode arranged on another side wall of the base member in an opposed relation to each of the first and second measuring electrodes, said another side wall being exposed to reference conditions.

6. The air/fuel ratio control system as claimed in claim 2, wherein said oxygen density sensor comprises a base member composed of a solid electrolyte, a first measuring electrode provided on a side wall of the base member exposed to the exhaust gas, a diffusion chamber formed in the base member to receive the exhaust gas through a small-diameter passage, a second measuring electrode having catalytic ability and arranged within the diffusion chamber, and at least one reference electrode arranged on another side wall of the base member in an opposed relation to each of the first and second measuring electrodes, said another side wall being exposed to reference conditions.

* * * * *